(12) United States Patent
Deem et al.

(10) Patent No.: US 7,503,922 B2
(45) Date of Patent: Mar. 17, 2009

(54) OBESITY TREATMENT TOOLS AND METHODS

(75) Inventors: Mark E. Deem, Mountain View, CA (US); Douglas S. Sutton, Pacifica, CA (US); Hanson S. Gifford, III, Woodside, CA (US); Bernard H. Andreas, Redwood City, CA (US); Ronald G. French, Santa Clara, CA (US)

(73) Assignee: Satiety, Inc., Palo Alto, CA (US)

( * ) Notice: Subject to any disclaimer, the term of this patent is extended or adjusted under 35 U.S.C. 154(b) by 1054 days.

(21) Appl. No.: 10/402,061

(22) Filed: Mar. 27, 2003

(65) Prior Publication Data

US 2004/0024386 A1    Feb. 5, 2004

Related U.S. Application Data

(63) Continuation of application No. 09/871,297, filed on May 30, 2001, now Pat. No. 6,558,400.

(51) Int. Cl.
*A61B 17/08* (2006.01)

(52) U.S. Cl. ........................................ 606/153; 125/898

(58) Field of Classification Search ................ 606/140, 606/141, 144; 128/898
See application file for complete search history.

(56) References Cited

U.S. PATENT DOCUMENTS

| | | | |
|---|---|---|---|
| 2,108,206 A | 2/1938 | Meeker | |
| 2,508,690 A | 5/1950 | Schmerl | |
| 3,372,443 A | 3/1968 | Daddona, Jr. | |
| 3,395,710 A | 8/1968 | Stratton et al. | |
| 3,986,493 A | 10/1976 | Hendren, III | |
| 4,057,065 A | 11/1977 | Thow | |

(Continued)

FOREIGN PATENT DOCUMENTS

EP        0 137 878 A1    4/1985

(Continued)

OTHER PUBLICATIONS

U.S. Appl. No. 60/234,260, filed Sep. 22, 2000, Schurr.

(Continued)

*Primary Examiner*—Kevin T Truong
*Assistant Examiner*—Victor X Nguyen
(74) *Attorney, Agent, or Firm*—Fulwider Patton LLP

(57) ABSTRACT

Various obesity treatment tools and methods are described herein, as well as treatments for other gastric-related diseases, e.g., GERD. Treatment includes reducing the size of the stomach pouch to limit the caloric intake as well as to provide an earlier feeling of satiety. This may be done by creating a smaller gastric pouch within the stomach directly from the interior of the stomach itself. The smaller pouches may be made through the use of individual anchoring devices, rotating probes, or volume reduction devices. A pyloroplasty procedure may also be performed to render the pyloric sphincter incompetent. A gastric bypass procedure may additionally be performed using a traumatic magnetic anastomoses devices so that sugars and fats are passed directly to the bowel while bypassing the stomach. Many of these procedures may be done in a variety of combinations. Treatment may create enforced behavioral modifications by discouraging the ingestion of high-caloric foods.

13 Claims, 37 Drawing Sheets

U.S. PATENT DOCUMENTS

| | | |
|---|---|---|
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A * | 8/1994 | Yoon ........................ 606/141 |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,408 A | 5/1995 | DiViesti et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A * | 10/1995 | Ahmed ....................... 606/140 |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A * | 6/1998 | Gangal et al. ................ 606/140 |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |

| | | | |
|---|---|---|---|
| 5,833,690 A | 11/1998 | Yates et al. | |
| 5,836,311 A | 11/1998 | Borst et al. | |
| 5,839,639 A | 11/1998 | Sauer et al. | |
| 5,860,581 A | 1/1999 | Robertson et al. | |
| 5,861,036 A | 1/1999 | Godin | |
| 5,868,141 A | 2/1999 | Ellias | |
| 5,868,760 A | 2/1999 | McGuckin, Jr. | |
| 5,876,448 A | 3/1999 | Thompson et al. | |
| 5,879,371 A | 3/1999 | Gardiner et al. | |
| 5,887,594 A * | 3/1999 | LoCicero, III | 128/898 |
| 5,888,196 A | 3/1999 | Bonutti | |
| 5,897,534 A | 4/1999 | Heim et al. | |
| 5,897,562 A | 4/1999 | Bolanos et al. | |
| 5,904,147 A | 5/1999 | Conlan et al. | |
| 5,906,625 A | 5/1999 | Bito et al. | |
| 5,910,105 A | 6/1999 | Swain et al. | |
| 5,910,149 A | 6/1999 | Kuzmak | |
| 5,921,993 A * | 7/1999 | Yoon | 606/140 |
| 5,927,284 A | 7/1999 | Borst et al. | |
| 5,928,264 A | 7/1999 | Sugarbaker et al. | |
| 5,935,107 A | 8/1999 | Taylor et al. | |
| 5,938,669 A | 8/1999 | Klaiber et al. | |
| 5,947,983 A | 9/1999 | Solar et al. | |
| 5,964,772 A | 10/1999 | Bolduc et al. | |
| 5,964,782 A | 10/1999 | Lafontaine et al. | |
| 5,972,001 A | 10/1999 | Yoon | |
| 5,972,002 A * | 10/1999 | Bark et al. | 606/140 |
| 5,976,161 A | 11/1999 | Kirsch et al. | |
| 5,980,537 A * | 11/1999 | Ouchi | 606/140 |
| 5,993,464 A | 11/1999 | Knodel | |
| 5,993,473 A | 11/1999 | Chan et al. | |
| 6,015,378 A | 1/2000 | Borst et al. | |
| 6,030,364 A | 2/2000 | Durgin et al. | |
| 6,030,392 A | 2/2000 | Dakov | |
| 6,042,538 A | 3/2000 | Puskas | |
| 6,044,847 A * | 4/2000 | Carter et al. | 128/898 |
| 6,067,991 A | 5/2000 | Forsell | |
| 6,074,343 A | 6/2000 | Nathanson et al. | |
| 6,083,241 A | 7/2000 | Longo et al. | |
| 6,086,600 A | 7/2000 | Kortenbach | |
| 6,113,609 A | 9/2000 | Adams | |
| 6,119,913 A | 9/2000 | Adams et al. | |
| 6,120,513 A * | 9/2000 | Bailey et al. | 606/141 |
| 6,136,006 A | 10/2000 | Johnson et al. | |
| 6,159,146 A | 12/2000 | El Gazayerli | |
| 6,159,195 A | 12/2000 | Ha et al. | |
| 6,165,183 A | 12/2000 | Kuehn et al. | |
| 6,179,195 B1 | 1/2001 | Adams et al. | |
| 6,186,942 B1 | 2/2001 | Sullivan et al. | |
| 6,186,985 B1 | 2/2001 | Snow | |
| 6,197,022 B1 | 3/2001 | Baker | |
| 6,200,318 B1 | 3/2001 | Har-Shai et al. | |
| 6,206,822 B1 | 3/2001 | Foley et al. | |
| 6,206,893 B1 | 3/2001 | Klein et al. | |
| 6,224,614 B1 | 5/2001 | Yoon | |
| 6,231,561 B1 | 5/2001 | Frazier et al. | |
| 6,248,058 B1 | 6/2001 | Silverman et al. | |
| 6,254,642 B1 | 7/2001 | Taylor | |
| 6,273,897 B1 | 8/2001 | Dalessandro et al. | |
| 6,279,809 B1 | 8/2001 | Nicolo | |
| 6,290,674 B1 | 9/2001 | Roue et al. | |
| 6,293,923 B1 | 9/2001 | Yachia et al. | |
| 6,302,917 B1 | 10/2001 | Dua et al. | |
| 6,312,437 B1 | 11/2001 | Kortenbach | |
| 6,328,689 B1 | 12/2001 | Gonzalez et al. | |
| 6,338,345 B1 | 1/2002 | Johnson et al. | |
| 6,352,543 B1 | 3/2002 | Cole | |
| 6,358,197 B1 | 3/2002 | Silverman et al. | |
| 6,379,366 B1 | 4/2002 | Fleischmann et al. | |
| 6,387,104 B1 | 5/2002 | Pugsley, Jr. et al. | |
| 6,398,795 B1 | 6/2002 | McAlister et al. | |
| 6,416,535 B1 | 7/2002 | Lazarus | |
| 6,423,087 B1 | 7/2002 | Sawada | |
| 6,432,040 B1 | 8/2002 | Meah | |
| 6,447,533 B1 | 9/2002 | Adams | |
| 6,460,543 B1 | 10/2002 | Forsell | |
| 6,475,136 B1 | 11/2002 | Forsell | |
| 6,491,707 B2 | 12/2002 | Makower et al. | |
| 6,494,888 B1 | 12/2002 | Laufer et al. | |
| 6,506,196 B1 | 1/2003 | Laufer | |
| 6,535,764 B2 | 3/2003 | Imran et al. | |
| 6,540,789 B1 | 4/2003 | Silverman et al. | |
| 6,551,310 B1 | 4/2003 | Ganz et al. | |
| 6,554,844 B2 | 4/2003 | Lee et al. | |
| 6,558,400 B2 | 5/2003 | Deem et al. | |
| 6,561,969 B2 | 5/2003 | Frazier et al. | |
| 6,572,629 B2 | 6/2003 | Kalloo et al. | |
| 6,579,301 B1 | 6/2003 | Bales et al. | |
| 6,592,596 B1 | 7/2003 | Geitz | |
| 6,605,037 B1 | 8/2003 | Gresl, Jr. et al. | |
| 6,626,899 B2 | 9/2003 | Houser et al. | |
| 6,632,227 B2 | 10/2003 | Adams | |
| 6,656,194 B1 | 12/2003 | Gannoe et al. | |
| 6,663,598 B1 | 12/2003 | Carrillo, Jr. et al. | |
| 6,663,639 B1 | 12/2003 | Laufer et al. | |
| 6,663,640 B2 | 12/2003 | Kortenbach | |
| 6,675,809 B2 | 1/2004 | Stack et al. | |
| 6,682,520 B2 | 1/2004 | Ingenito | |
| 6,689,062 B1 | 2/2004 | Mesallum | |
| 6,692,485 B1 | 2/2004 | Brock et al. | |
| 6,716,222 B2 | 4/2004 | McAlister et al. | |
| 6,733,512 B2 | 5/2004 | McGhan | |
| 6,736,822 B2 | 5/2004 | McClellan et al. | |
| 6,740,098 B2 | 5/2004 | Abrams et al. | |
| 6,740,121 B2 | 5/2004 | Geitz | |
| 6,746,460 B2 | 6/2004 | Gannoe et al. | |
| 6,746,489 B2 | 6/2004 | Dua et al. | |
| 6,754,536 B2 | 6/2004 | Swoyer et al. | |
| 6,755,849 B1 | 6/2004 | Gowda et al. | |
| 6,755,869 B2 | 6/2004 | Geitz | |
| 6,756,364 B2 | 6/2004 | Barbier et al. | |
| 6,764,518 B2 | 7/2004 | Godin | |
| 6,773,440 B2 | 8/2004 | Gannoe et al. | |
| 6,773,441 B1 * | 8/2004 | Laufer et al. | 606/153 |
| 6,786,898 B2 | 9/2004 | Guenst | |
| 6,790,214 B2 | 9/2004 | Kraemer et al. | |
| 6,802,868 B2 | 10/2004 | Silverman et al. | |
| 6,821,285 B2 | 11/2004 | Laufer et al. | |
| 6,830,546 B1 | 12/2004 | Chin et al. | |
| 6,835,199 B2 | 12/2004 | McGuckin, Jr. et al. | |
| 6,835,200 B2 | 12/2004 | Laufer et al. | |
| 6,837,848 B2 | 1/2005 | Bonner et al. | |
| 6,840,423 B2 | 1/2005 | Adams et al. | |
| 6,845,776 B2 | 1/2005 | Stack et al. | |
| 6,896,682 B1 * | 5/2005 | McClellan et al. | 606/140 |
| 6,916,332 B2 | 7/2005 | Adams | |
| 6,926,722 B2 | 8/2005 | Geitz | |
| 6,966,919 B2 | 11/2005 | Sixto, Jr. et al. | |
| 6,981,978 B2 | 1/2006 | Gannoe | |
| 6,991,643 B2 | 1/2006 | Saadat | |
| 6,994,715 B2 | 2/2006 | Gannoe et al. | |
| 7,020,531 B1 | 3/2006 | Colliou et al. | |
| 7,025,791 B2 | 4/2006 | Levine et al. | |
| 7,033,373 B2 | 4/2006 | de al Torre et al. | |
| 7,033,378 B2 | 4/2006 | Smith et al. | |
| 7,033,384 B2 | 4/2006 | Gannoe et al. | |
| 7,037,343 B2 | 5/2006 | Imran | |
| 7,037,344 B2 | 5/2006 | Kagan et al. | |
| 7,063,715 B2 | 6/2006 | Onuki et al. | |
| 7,083,629 B2 | 8/2006 | Weller et al. | |
| 7,083,630 B2 | 8/2006 | DeVries et al. | |
| 7,087,011 B2 | 8/2006 | Cabiri et al. | |
| 7,097,650 B2 | 8/2006 | Weller et al. | |
| 2001/0014800 A1 | 8/2001 | Frazier et al. | |
| 2001/0020190 A1 | 9/2001 | Taylor | |
| 2001/0037127 A1 | 11/2001 | De Hoyos Garza | |

| | | | | | | |
|---|---|---|---|---|---|---|
| 2002/0022851 A1 | 2/2002 | Kalloo et al. | | 2004/0225194 A1 | 11/2004 | Smith et al. |
| 2002/0035361 A1 | 3/2002 | Houser et al. | | 2004/0225305 A1* | 11/2004 | Ewers et al. ............... 606/153 |
| 2002/0040226 A1 | 4/2002 | Laufer et al. | | 2004/0236357 A1 | 11/2004 | Kraemer et al. |
| 2002/0047036 A1 | 4/2002 | Sullivan et al. | | 2004/0249362 A1 | 12/2004 | Levine et al. |
| 2002/0058967 A1 | 5/2002 | Jervis | | 2005/0010162 A1 | 1/2005 | Utley et al. |
| 2002/0072761 A1 | 6/2002 | Abrams et al. | | 2005/0033328 A1 | 2/2005 | Laufer et al. |
| 2002/0077661 A1 | 6/2002 | Saadat | | 2005/0038415 A1 | 2/2005 | Rohr et al. |
| 2002/0078967 A1 | 6/2002 | Sixto, Jr. et al. | | 2005/0049718 A1 | 3/2005 | Dann et al. |
| 2002/0082621 A1 | 6/2002 | Schurr et al. | | 2005/0055038 A1 | 3/2005 | Kelleher et al. |
| 2002/0143346 A1 | 10/2002 | McGuckin, Jr. et al. | | 2005/0055039 A1 | 3/2005 | Burnett et al. |
| 2002/0165589 A1 | 11/2002 | Imran et al. | | 2005/0075622 A1 | 4/2005 | Levine et al. |
| 2002/0183768 A1 | 12/2002 | Deem et al. | | 2005/0075653 A1 | 4/2005 | Saadat et al. |
| 2002/0193816 A1 | 12/2002 | Laufer et al. | | 2005/0080444 A1 | 4/2005 | Kraemer et al. |
| 2003/0040804 A1 | 2/2003 | Stack et al. | | 2005/0085787 A1 | 4/2005 | Laufer |
| 2003/0040808 A1 | 2/2003 | Stack et al. | | 2005/0096750 A1 | 5/2005 | Kagan et al. |
| 2003/0065340 A1 | 4/2003 | Geitz | | 2005/0119671 A1 | 6/2005 | Reydel et al. |
| 2003/0065359 A1 | 4/2003 | Weller et al. | | 2005/0143760 A1 | 6/2005 | Imran |
| 2003/0093117 A1 | 5/2003 | Saadat | | 2005/0148818 A1 | 7/2005 | Mesallum |
| 2003/0109892 A1 | 6/2003 | Deem et al. | | 2005/0149067 A1 | 7/2005 | Takemoto et al. |
| 2003/0109931 A1 | 6/2003 | Geitz | | 2005/0149114 A1 | 7/2005 | Cartledge et al. |
| 2003/0109935 A1 | 6/2003 | Geitz | | 2005/0177176 A1 | 8/2005 | Gerbi et al. |
| 2003/0120265 A1 | 6/2003 | Deem et al. | | 2005/0192599 A1 | 9/2005 | Demarais |
| 2003/0120285 A1 | 6/2003 | Kortenbach | | 2005/0192601 A1 | 9/2005 | Demarais |
| 2003/0120289 A1 | 6/2003 | McGuckin, Jr. et al. | | 2005/0194038 A1 | 9/2005 | Brabec et al. |
| 2003/0132267 A1 | 7/2003 | Adams et al. | | 2005/0194294 A1 | 9/2005 | Oexle et al. |
| 2003/0158563 A1 | 8/2003 | McClellan et al. | | 2005/0194312 A1 | 9/2005 | Niemeyer et al. |
| 2003/0158601 A1 | 8/2003 | Silverman et al. | | 2005/0195925 A1 | 9/2005 | Traber |
| 2003/0171760 A1 | 9/2003 | Gambale | | 2005/0195944 A1 | 9/2005 | Bartels et al. |
| 2003/0208209 A1 | 11/2003 | Gambale et al. | | 2005/0196356 A1 | 9/2005 | Leinen et al. |
| 2003/0208212 A1* | 11/2003 | Cigaina ...................... 606/151 | | 2005/0197540 A1 | 9/2005 | Liedtke |
| 2003/0225312 A1 | 12/2003 | Suzuki et al. | | 2005/0197622 A1 | 9/2005 | Blumenthal et al. |
| 2004/0006351 A1 | 1/2004 | Gannoe et al. | | 2005/0197684 A1 | 9/2005 | Koch |
| 2004/0009224 A1 | 1/2004 | Miller | | 2005/0198476 A1 | 9/2005 | Gazsi et al. |
| 2004/0010271 A1 | 1/2004 | Kortenbach | | 2005/0203547 A1 | 9/2005 | Weller et al. |
| 2004/0024386 A1 | 2/2004 | Deem et al. | | 2005/0203548 A1 | 9/2005 | Weller et al. |
| 2004/0037865 A1 | 2/2004 | Miller | | 2005/0228415 A1 | 10/2005 | Gertner |
| 2004/0039452 A1 | 2/2004 | Bessler | | 2005/0228504 A1 | 10/2005 | Demarais |
| 2004/0044354 A1 | 3/2004 | Gannoe et al. | | 2005/0256533 A1 | 11/2005 | Roth et al. |
| 2004/0049209 A1 | 3/2004 | Benchetrit | | 2005/0256587 A1 | 11/2005 | Egan |
| 2004/0059349 A1 | 3/2004 | Sixto, Jr. et al. | | 2006/0020247 A1 | 1/2006 | Kagan et al. |
| 2004/0059354 A1 | 3/2004 | Smith et al. | | 2006/0020254 A1 | 1/2006 | Hoffmann |
| 2004/0059358 A1 | 3/2004 | Kortenbach et al. | | 2006/0020276 A1 | 1/2006 | Saadat et al. |
| 2004/0082963 A1 | 4/2004 | Gannoe et al. | | 2006/0036267 A1 | 2/2006 | Saadat et al. |
| 2004/0087977 A1 | 5/2004 | Nolan et al. | | 2006/0106288 A1 | 5/2006 | Roth et al. |
| 2004/0088008 A1 | 5/2004 | Gannoe et al. | | 2006/0122462 A1 | 6/2006 | Roth et al. |
| 2004/0089313 A1 | 5/2004 | Utley et al. | | 2006/0142787 A1 | 6/2006 | Weller et al. |
| 2004/0092892 A1 | 5/2004 | Kagan et al. | | 2006/0151568 A1 | 7/2006 | Weller et al. |
| 2004/0092974 A1 | 5/2004 | Gannoe et al. | | | | |
| 2004/0097989 A1 | 5/2004 | Molina Trigueros | | FOREIGN PATENT DOCUMENTS | | |
| 2004/0107004 A1 | 6/2004 | Levine et al. | | | | |
| 2004/0116949 A1 | 6/2004 | Ewers et al. | | EP | 0 174 843 | 3/1986 |
| 2004/0122456 A1 | 6/2004 | Saadat et al. | | EP | 0 174 843 A1 | 3/1986 |
| 2004/0122473 A1 | 6/2004 | Ewers et al. | | EP | 0 246 999 A1 | 11/1987 |
| 2004/0122526 A1 | 6/2004 | Imran | | EP | 0 540 010 A2 | 5/1993 |
| 2004/0133147 A1 | 7/2004 | Woo | | JP | 63277063 A | 11/1988 |
| 2004/0133238 A1 | 7/2004 | Cerier | | JP | 63279854 | 11/1988 |
| 2004/0138525 A1 | 7/2004 | Saadat | | JP | 63302863 A | 12/1988 |
| 2004/0138526 A1 | 7/2004 | Guenst | | JP | 01049572 A | 2/1989 |
| 2004/0138529 A1 | 7/2004 | Wiltshire et al. | | JP | 04297219 | 10/1992 |
| 2004/0138531 A1 | 7/2004 | Bonner et al. | | WO | WO 94/18893 A1 | 9/1994 |
| 2004/0138682 A1 | 7/2004 | Onuki et al. | | WO | WO 99/17662 A1 | 4/1999 |
| 2004/0147958 A1 | 7/2004 | Lam et al. | | WO | WO 99/53827 | 10/1999 |
| 2004/0148021 A1 | 7/2004 | Cartledge et al. | | WO | WO 00/32137 A1 | 6/2000 |
| 2004/0148034 A1 | 7/2004 | Kagan et al. | | WO | WO 00/48656 A1 | 8/2000 |
| 2004/0158331 A1 | 8/2004 | Stack et al. | | WO | WO 00/78227 | 12/2000 |
| 2004/0162568 A1 | 8/2004 | Saadat et al. | | WO | WO 00/78229 | 12/2000 |
| 2004/0167546 A1 | 8/2004 | Saadat et al. | | WO | WO 01/66018 A1 | 9/2001 |
| 2004/0172141 A1 | 9/2004 | Stack et al. | | WO | WO 01/67964 A2 | 9/2001 |
| 2004/0181242 A1 | 9/2004 | Stack et al. | | WO | WO 01/85034 | 11/2001 |
| 2004/0193190 A1 | 9/2004 | Liddicoat et al. | | WO | WO 01/85034 A1 | 11/2001 |
| 2004/0210243 A1 | 10/2004 | Gannoe et al. | | WO | WO 02/24080 | 3/2002 |
| 2004/0215180 A1 | 10/2004 | Starkebaum et al. | | WO | WO 02/24080 A2 | 3/2002 |
| 2004/0225183 A1 | 11/2004 | Michlitsch et al. | | WO | WO 02/35980 A2 | 5/2002 |

| | | |
|---|---|---|
| WO | WO 02/39880 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 | 12/2003 |
| WO | WO 03/105563 A2 | 12/2003 |
| WO | WO 03/105671 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Cummings, D.E. et al. (2002). "Plasma Ghrelin Levels After Diet-Induced Weight Loss or Gastric Bypass Surgery," *N. Engl. J. Med.* 346(21):1623-1630.

Davenport, H.W. (1971). *Physiology of the Digestive Tract*, Third Edition, Year Book Medical Publishers, Inc.: Chicago, IL, pp. 9-10 (Table of Contents Only.).

DeMeester, T.R. (2002). "Evolving Concepts of Reflux: The Ups and Downs of the LES," *Can. J. Gastroenterol* 16(5):327-331.

Villar, H.V. et al. (1981). "Mechanisms of Satiety and Gastric Emptying After Gastric Partitioning and Bypass," *Surgery* 90(2):229-236.

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique For Gastroplasty As A Substitute For The Esophagus: Fundus Rotation Gastroplasty, *Journal Of The American College Of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D.[1], et al.. Gastro-Clip® Gastroplasty: A Very Long-Term Complication, *Obesity Surgery*, 14, © FD-Communications Inc.. 2004.

Clark, Charlene, R.N., The Gastric Bubble: Medicine, Magic or Mania? *SGA Journal*, vol. 9, No. 2, pp. 45-47, Fall 1986.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, Flexible Endoscopic Suturing For Treatment Of GERD: A Multicenter Trial, *Gastrointestinal Endoscopy*,. vol. 53, No. 4, pp. 416-422, 2001.

Gray, Henry, R.R.S., *Anatomy of the Human Body*, The Digestive System, Thirtieth American Edition, pp. 1466-1467 (Undated).

Guidant, Internet, AXIUS™ VACUUM 2 Stabilizer Systems, Internet Website—www.guidant.com/products/axius_vacuum.shtml, 8 pages, visited May 27, 2003.

Hepworth, Clive C. FRCS et al., Mechanical Endoscopic Methods Of Haemostasis For Bleeding Peptic Ulcers: A Review, *Bailliere's Clinical Gastroenterology*, vol. 14, No. 3 pp. 467-476, 2000.

Ikeda, Y. et al., New Suturing Device For Transanal Endoscopic Microsurgery, *Blackwell Science Ltd.* p. 1290, 1997.

Johnson & Johnson Gateway[SM] Endopath 3mm, 5mm and 10 mm Diameter Endoscopic Instruments, Internet Website—www.inigateway.com/home,ihtml?loc=USENG&page=viewContent&parentld-0900..., 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor, Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing And Stapling Machines, *Endoscopy* pp. 205-210, © Georg Thieme Verlag Stuttgart, New York, 1997.

Swain, C. Paul, M.D. et al., An Endoscopic Sewing Machine, *Gastrointestinal Endoscopy*, vol. 32, No. 1, pp. 36-38, 1986.

Swain, C. Paul, M.D. et al., An Endoscopic Stapling Device: The Development Of A New Flexible Endoscopically Controlled Device For Placing Multiple Transmural Staples In Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Wullstein, C., et al., Compression Anastomosis (AKA-2) in Colorectal Surgery: Results in 442 Consecutive Patients, *British Journal of Surgery 2000*, pp. 1071-1075.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print_pp. 1-20, Medscape General Medicine 4(1), 2003 © 2002 Medscape, downloaded Oct. 9, 2006.

* cited by examiner

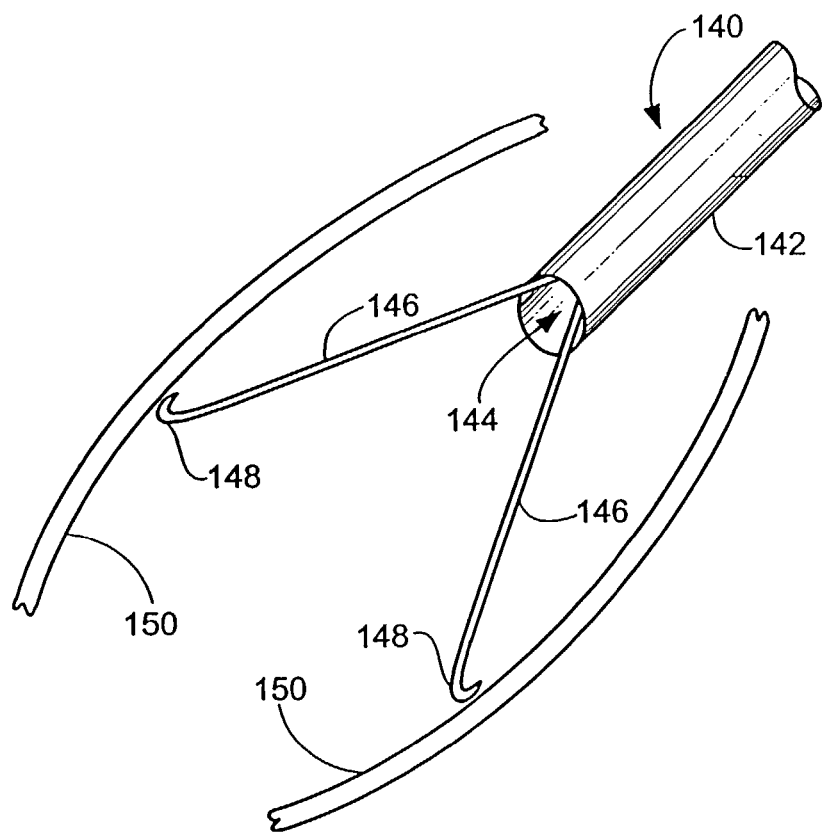
FIG. 7A
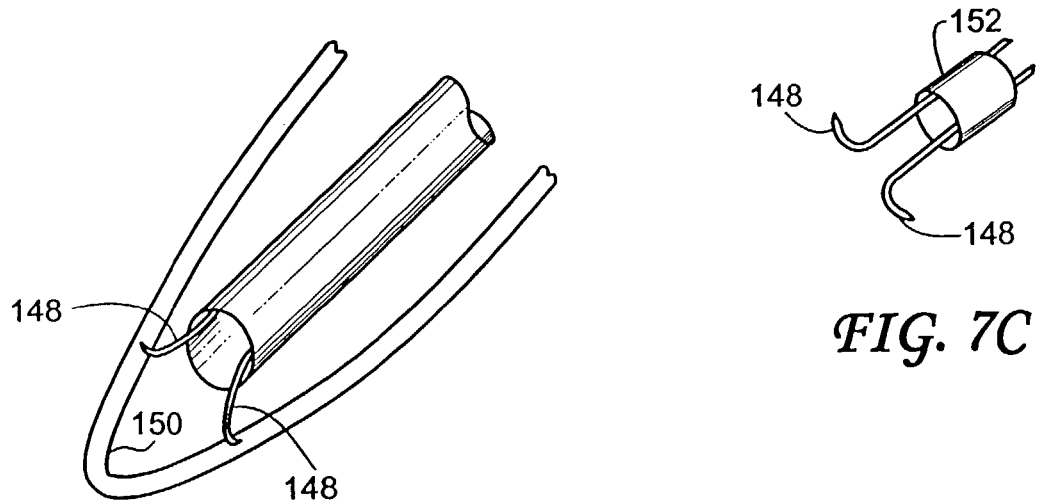
FIG. 7B
FIG. 7C

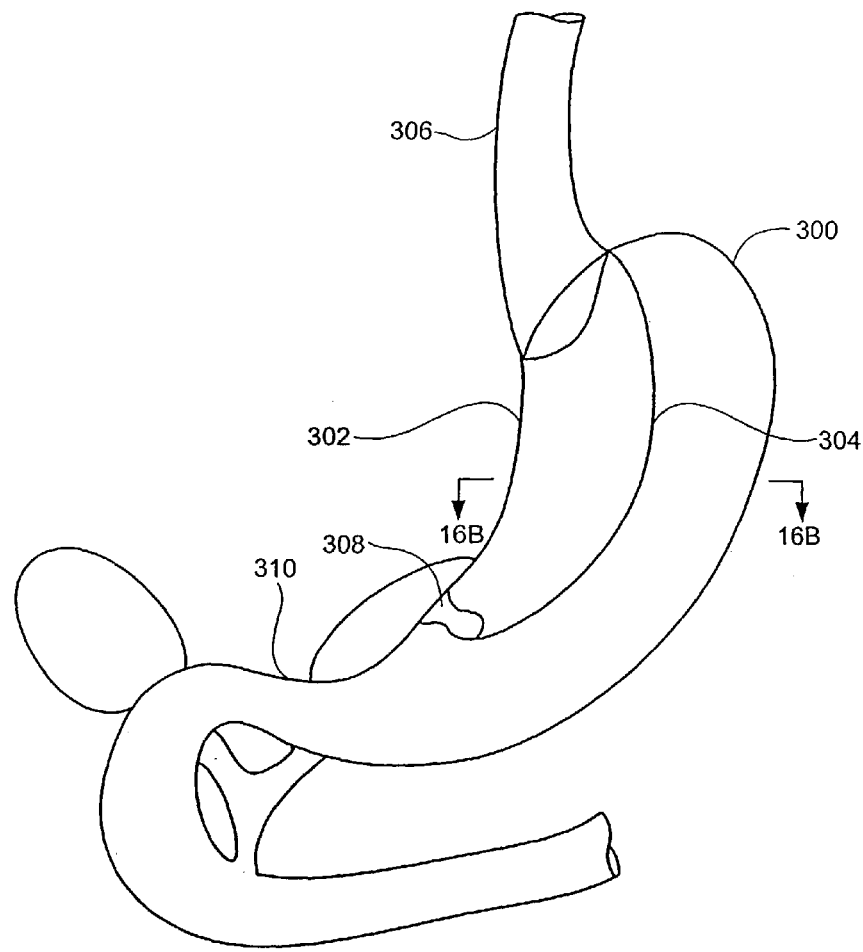
FIG. 16A
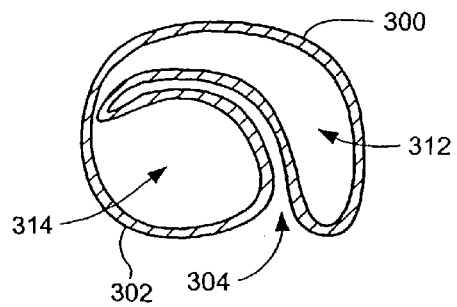
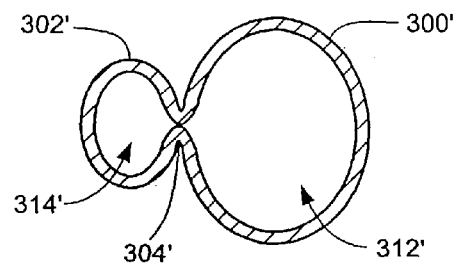
FIG. 16B        FIG. 16C

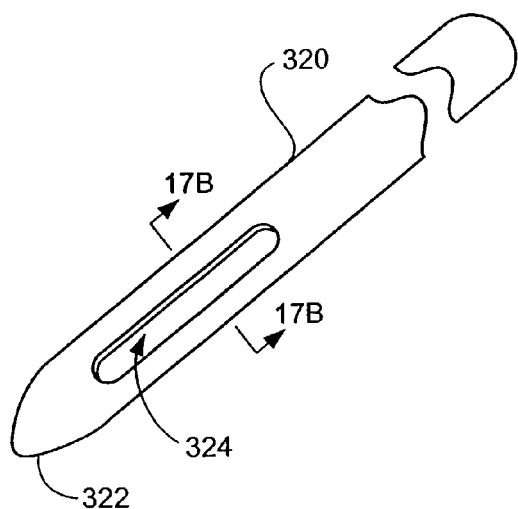
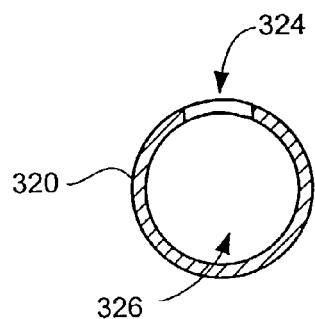
FIG. 17A
FIG. 17B
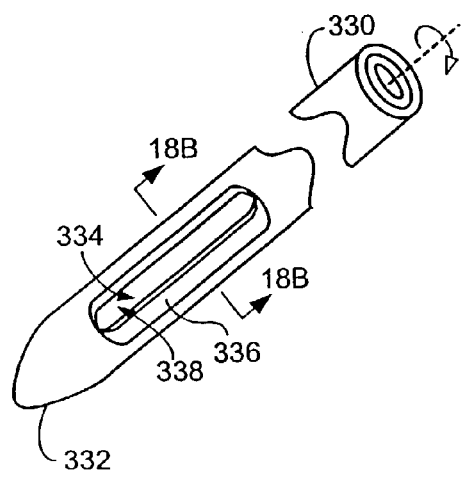
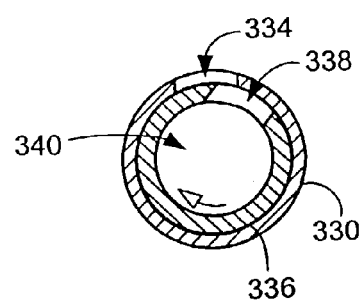
FIG. 18A
FIG. 18B

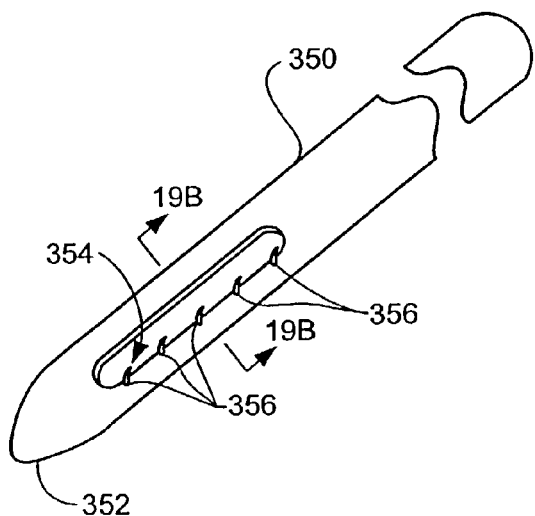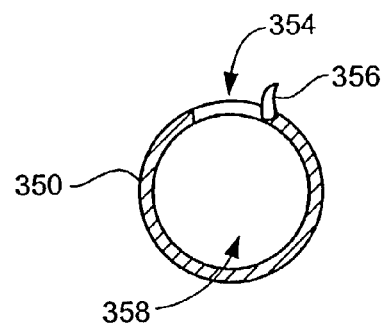
FIG. 19A  FIG. 19B
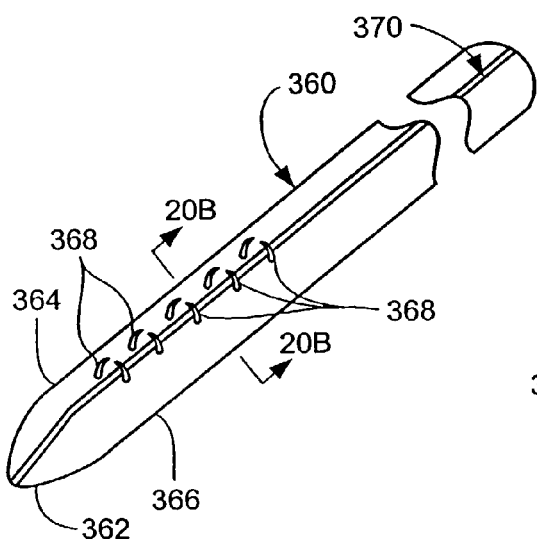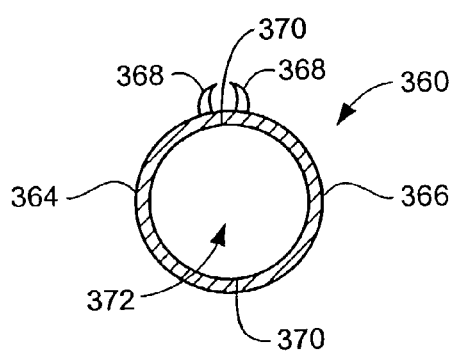
FIG. 20A  FIG. 20B

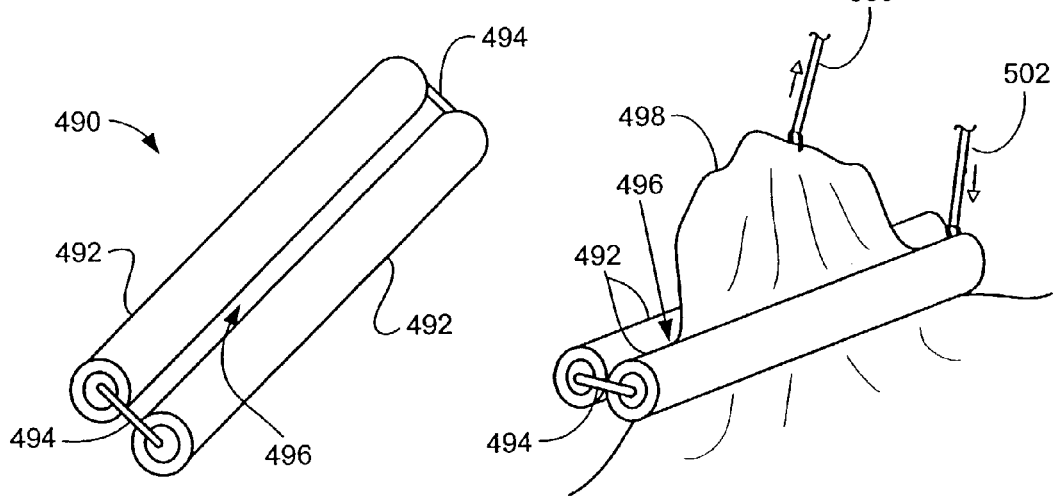
FIG. 29A
FIG. 29B
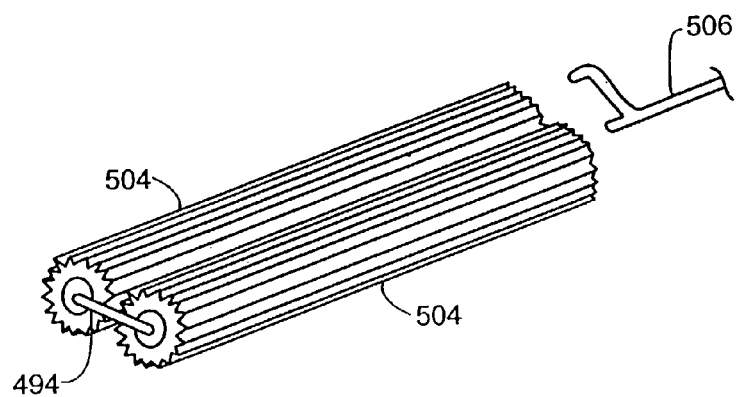
FIG. 29C

OBESITY TREATMENT TOOLS AND METHODS

CROSS-REFERENCE TO RELATED APPLICATIONS

This is a continuation of U.S. patent application Ser. No. 09/871,297, filed May 30, 2001, now U.S. Pat. No. 6,558,400, which is incorporated herein by reference in its entirety.

TECHNICAL FIELD OF THE INVENTION

The present invention relates generally to tools and methods for the treatment of obesity. More particularly, the present invention relates to tools and methods for performing less traumatic gastroplasty procedures.

BACKGROUND OF THE INVENTION

Obesity is considered a major health problem with annual associated costs reaching $100 billion in the U.S. alone. Morbid obesity is a condition of obesity with the presence of a secondary debilitating progressive disease and is generally associated with a body mass index (BMI) $\geqq 40$ kg/m$^2$. While the basic mechanism of obesity is simply an imbalance between caloric intake and burn rate, the underlying factors are varied and complex and conservative attempts at sustained weight loss with this population are almost always unsuccessful. Often, there are genetic and other biological influences that may override environmental causes. Consequently, obesity is a disease that eludes a simple treatment, with a recurrence rate above 90% for those who attempt to lose weight. Moreover, long-term results using conservative treatments for morbid obesity are generally unsuccessful and are typically associated with further loss of self-esteem with the regaining of weight. Hypertension, cardiovascular disease, diabetes, along with a host of other comorbidities all make morbid obesity second only to smoking as a preventable cause of death.

Surgical procedures for obesity date back to 1889 (Billroth) with the earliest peer reviewed procedure being the jejuno-ileal bypass in 1954 (Kreman). A successful procedure is commonly defined as one that results in at least 50% excess weight loss at 2 years. Today, the most commonly done operation is the Roux-en-Y gastric bypass (RYGB), with around 35,000 performed annually in the U.S. Other forms of bariatric surgery include Fobi pouch, bilio-pancreatic diversion, and gastroplasty or "stomach stapling". The single existing procedure that involves an implanted device is the Lap-Band, which is a laparoscopically installed inflatable cuff that is placed around the top of the stomach just below the lower esophageal sphincter (LES). This device affects satiety only (no reduced caloric absorption). Because there is more to obesity than simple overeating, it is unlikely that Lap-Band by itself will ever be as effective as a surgery that includes other physiologic feedback mechanisms.

The RYGB procedure is a procedure which has become very common in bariatric surgery. This procedure facilitates the movement of the jejunum to a high position by using a retrocolic Roux-en-Y loop. The procedure is generally performed through a 6-8 inch incision extending from the end of the breastbone to just above the navel. The stomach is completely divided into 2 unequal portions (a smaller upper and a larger lower gastric pouch) using an automatic stapling device with the raw surface reinforced with additional sutures. The upper pouch typically measures less than about 1 ounce or 20 cc, while the lower larger pouch remains generally intact and continues to secrete stomach juices flowing through the intestinal tract.

A segment of the small intestine (just distal of the duodenum or proximal of the jejunum) is then brought from the lower abdomen and joined with the upper pouch to form an end-to-end anastomosis created through a half-inch opening, also called the stoma. This segment of the small intestine is called the "Roux loop" and carries food from the upper pouch to the remainder of the intestines, where the food is digested. The remaining lower pouch and the attached segment of duodenum are then reconnected to form another anastomotic connection to the Roux loop at a location approximately 50-150 cm (1.6-4.9 ft) from the stoma, typically using a stapling instrument. It is at this connection that the digestive juices from the bypassed stomach, pancreas, and liver enter the jejunum or ileum to aid in the digesting of food. Due to the small size of the upper pouch, patients are forced to eat at a slower rate and are satiated much more quickly, thereby reducing the caloric intake (typically between about 1000-1200 Calories).

Because the food enters the intestines directly, conditions known as the "dumping syndrome" are created when certain types of "junk foods" are consumed (usually sweets and other simple carbohydrates). This creates unpleasant feelings of nausea, diarrhea, nervousness, and sweating, which in turn discourages patients from developing unhealthy eating patterns. With the RYGB procedure, a loss of at least 50% of excess body weight (EBW) is maintained in approximately 60% of patients at 5 years with a reduced complication rate than other procedures.

In creating the anastomoses in the RYGB procedure, several methods have previously been developed to maintain channel integrity. However, the conventional RYGB procedure requires a great deal of operative time and because of the degree of invasiveness, post-operative recovery time can be quite lengthy and painful.

Aside from the RYGB procedure, another gastrointestinal disease which relates to the stomach is gastroesophageal reflux disease (GERD). The lower esophageal sphincter is located in a distal portion of the esophagus adjacent to the junction between the esophagus and the stomach. When food is digested, a properly functioning lower esophageal sphincter would allow food to pass from the esophagus to the stomach while preventing reverse flow. However, GERD is a disorder where the esophageal sphincter allows the stomach contents, which includes gastric acid and bile, to flow back into the distal portion of the esophagus. Some complications associated with GERD include heartburn, pulmonary disorders, chest pain, esophageal ulcers, esophagitis, Barrett's esophagus, and esophageal carcinoma.

Common treatments for GERD include the administration of prescription acid blockers. But these drugs afford only short term relief; additionally, these drugs can be expensive and may have long-term side effects. Surgical procedures have included a procedure called the Nissen fundoplication, where a portion of the gastric fundus is wrapped around the esophagus. The wrapped fundus applies pressure to the esophagus to limit the reverse flow of the stomach contents. Effectively elongating the esophagus by fundoplication or by extending it via a staple line may be done to treat GERD. Conventional fundoplication procedures may be effective at treating GERD, but they also have disadvantages. For instance, many of these procedures require large incisions to be made in a patient. Laparoscopic procedures typically require several smaller incisions formed in the abdominal wall for the insertion of instruments into the patient's body.

However, such procedures can be expensive and they can increase the risks of post-operative hernias, accidental organ perforations, and other related drawbacks.

Examples related to the field of gastroplasty are described below.

U.S. Pat. No. 5,549,621 to Bessler et al., which is incorporated herein by reference in its entirety, pertains to an apparatus and method for performing vertical banded gastroplasty without the use of staples. The described device uses at least two clamping bars to create a tubular-shaped pouch. However, the device is deployed laparoscopically onto the external surface of the stomach.

U.S. Pat. No. 5,382,231 to Shlain, which is incorporated herein by reference in its entirety, describes a device for transesophageal stomach retraction by a device having vacuum ports utilized to draw the stomach over the device. However, this device is used for manipulating and retracting a patient's stomach from the inside during a variety of surgical procedures and is not a permanent procedure for creating an internal pouch within the stomach itself.

U.S. Pat. No. 5,345,949 to Shlain, which is incorporated herein by reference in its entirety, relates to laparoscopic methods and tools for inserting a banding device to bring the walls of the stomach adjacent to one another between the proximal pouch and the distal region of the stomach. But there is no procedure for the creation of an internal pouch internally created from the stomach.

Examples related to the field of GERD treatment are described below.

U.S. Pat. No. 6,159,146 to El Gazayerli, which is incorporated herein by reference in its entirety, relates to a device which is inserted transesophageally and engages the inside anterior wall of the fundus and secures it to the side of the esophagus.

U.S. Pat. No. 6,113,609 to Adams, which is incorporated herein by reference in its entirety, pertains to a system which includes placement of a distal anchor through a hole formed in the wall of the esophagus and through a hole formed in the gastric wall, which are then fastened together.

U.S. Pat. No. 5,571,116 to Bolanos et al., which is incorporated herein by reference in its entirety, pertains to an invagination device which approximates the lower esophagus and the fundus of the stomach.

However, all of these examples are limited to treatments for GERD which involves the attachment of the fundus, or upper portion of the stomach, to the esophagus.

SUMMARY OF THE INVENTION

Various tools and methods of treatment for obesity are described herein which are less traumatic and less invasive than procedures currently available. A variety of methods for the treatment of obesity, as well as other gastric-related diseases, e.g., gastroesophageal reflux disease (GERD), are disclosed. One method involves reducing the size of the stomach pouch to limit the caloric intake as well as to provide an earlier feeling of satiety. This may be done by creating a smaller gastric pouch within the stomach. This procedure optionally may be enhanced by performing a pyloroplasty prior to and/or in conjunction with the pouch size reduction, i.e., rendering the pyloric sphincter incompetent. This increases the rate of stomach emptying, allowing sugars and fats to pass directly into the bowel, thereby inducing dumping. Moreover, the food in the stomach may be made to also bypass a proximal portion of the bowel, i.e., a portion of the duodenum and jejunum, by creating a gastric anastomosis thereby creating a malabsorption of sugars and fats which are mostly absorbed in the bypassed portion of the duodenum and jejunum. Sugars and fats entering the bowel directly from the stomach rather than passing through the pylorus and proximal duodenum and jejunum may cause "dumping" syndrome and diarrhea. This in turn may create enforced behavioral modifications, thereby discouraging the patient from eating these types of high-caloric foods.

In forming a modified pouch, a marking device, such as a bougie, may be used at the beginning of the procedure, to create a dye marker "road map" on the interior surface of the stomach from the pylorus to the esophagus. This may enable visualization by, e.g., an endoscope, to give the physician a clear reference point for staple or fixation element placement. A distal balloon, which is preferably attached to an inflation tip at a distal end, may be inserted into the pylorus to stabilize the bougie during the procedure and may be inflated from the proximal end of the tubing by the physician.

In reducing the stomach size, one variation involves grasping the interior walls of the stomach, preferably via an endoscope advanced transesophageally, and placing one to several individual fixation elements on opposing interior walls and then bringing those fixation elements together. The stomach pouch may be modified and/or created by a variety of other device variations utilizing other methods, e.g., stapling opposing sides of a stomach together to form two separate lumens from within the interior surface of the stomach. An endoscopic stapling device may be used to accomplish such a task. Such an endoscopic stapler preferably brings two regions of tissue into apposition and may then apply a fastening element, e.g., staples, clips, tags, screws, etc., into the two regions of tissue to affix them together.

In addition to endoscopically applied stapling and clip devices, rotating and rotatable probes may also be used to form a modified smaller lumen within a main lumen. Such probes generally may be inserted into a stomach endoscopically and may engage a portion of the interior lining of the stomach and may then be rotated to roll the engaged portion of the stomach wall around the probe itself to bring the wall in apposition with another portion of the stomach wall. Such rotating probes may be used to create a blind-ended pouch of stomach within the main stomach lumen, or as with the other devices, may be used to create a smaller pouch exiting into the pylorus. Once the roll of stomach wall is brought into apposition, a row or a plurality of fasteners, e.g., staples, blind staples, clips, tags, adhesives, screws, etc., may be used to maintain the stomach. Moreover, other variations may include gastric volume reduction devices as part of the present invention. Such volume reduction devices generally may be inserted into a stomach trans-esophageally through the use of, e.g., an endoscope. The reduction device may be used to draw or engage a portion of the interior lining of the stomach; the drawn or engaged portion may then be eventually removed, either actively or through natural processes, e.g., pressure necrosis.

To aid in the overall effect, a pyloroplasty procedure may also be performed to enhance treatment. The pyloroplasty may be performed prior to (preferable), in conjunction with, or following the gastric reduction procedure. A pyloroplasty procedure typically results in the pyloric sphincter being rendered incompetent. Generally, a pyloroplasty device may be passed endoscopically through the esophagus, into the stomach, and preferably into position in or across the pylorus. Energy or a stimulus is then preferably applied to the pylorus to render it incompetent.

Moreover, an additional anastomosis gastric bypass procedure may also be performed to further enhance treatment. The anastomosis procedure may be performed preferably prior to, in conjunction with, or following the gastric reduction and pyloroplasty procedures (if performed at all). The procedure generally involves endoscopically or laparoscopically creating a side-to-side anastomosis preferably from within the stomach and bowel and within the digestive tract. This procedure may be similar to the Roux-en-Y gastric bypass procedure but with minimal trauma.

BRIEF DESCRIPTION OF THE DRAWINGS

FIGS. 7A and 7B show a superior view of an extendable double hook device attaching to a stomach wall.

FIG. 7C shows the device of FIG. 7A locked by a crimping variation.

FIG. 15E shows the assembly view of another variation of the device of FIG. 15A wherein the clip may be replaced by a screw.

FIG. 16A shows an example of a modified stomach created by a rotating device variation.

FIG. 16B shows a superior cross section view of the stomach of FIG. 16A where the modified lumen may be created by rotating the interior stomach lining upon itself.

FIG. 16C shows an alternate superior cross section view of the stomach of FIG. 16A where the modified lumen may be created by rotating apposed portions of the interior stomach lining upon itself.

FIGS. 17A and 17B show an isometric and cross section view, respectively, of a vacuum tube variation.

FIGS. 18A and 18B show an isometric and cross section view, respectively, of a counter-rotating vacuum tube variation.

FIGS. 19A and 19B show an isometric and cross section view, respectively, of a vacuum tube variation with attachment points.

FIGS. 20A and 20B show an isometric and cross section view, respectively, of a split tube variation.

FIGS. 29A and 29B show an isometric view on a variation of a gastric volume reduction device utilizing tractive rollers to draw tissue up between them.

FIG. 29C shows another variation of the device of FIGS. 29A and 29B with ratcheted rollers.

DETAILED DESCRIPTION OF THE INVENTION

With obesity becoming an increasing problem, various tools and methods of treatment are described herein which are less traumatic and less invasive than procedures currently available. As described in further detail below, a variety of methods for the treatment of obesity, as well as other gastric-related diseases, are disclosed. Generally, the size of the stomach pouch may be reduced to limit the caloric intake as well as to provide an earlier feeling of satiety. This may be accomplished by creating a smaller gastric pouch within the stomach by a variety of methods. This procedure optionally may be enhanced by performing a pyloroplasty prior to and/or in conjunction with the pouch size reduction, i.e., rendering the pyloric sphincter incompetent. Additionally, the food in the stomach may be made to also bypass a proximal portion of the bowel, i.e., a portion of the duodenum and jejunum, by creating a gastric anastomosis thereby creating a malabsorption of sugars and fats which are mostly absorbed in the bypassed portion of the duodenum and jejunum. Sugars and fats entering the bowel directly from the stomach rather than passing through the pylorus and proximal duodenum and jejunum may cause "dumping" syndrome and diarrhea. Moreover, rendering the pylorus incompetent may also lead to dumping syndrome partly because of the rapid gastric emptying which may occur. This in turn may create enforced behavioral modifications, thereby discouraging the patient from eating these types of high-caloric foods.

Figure 1A:
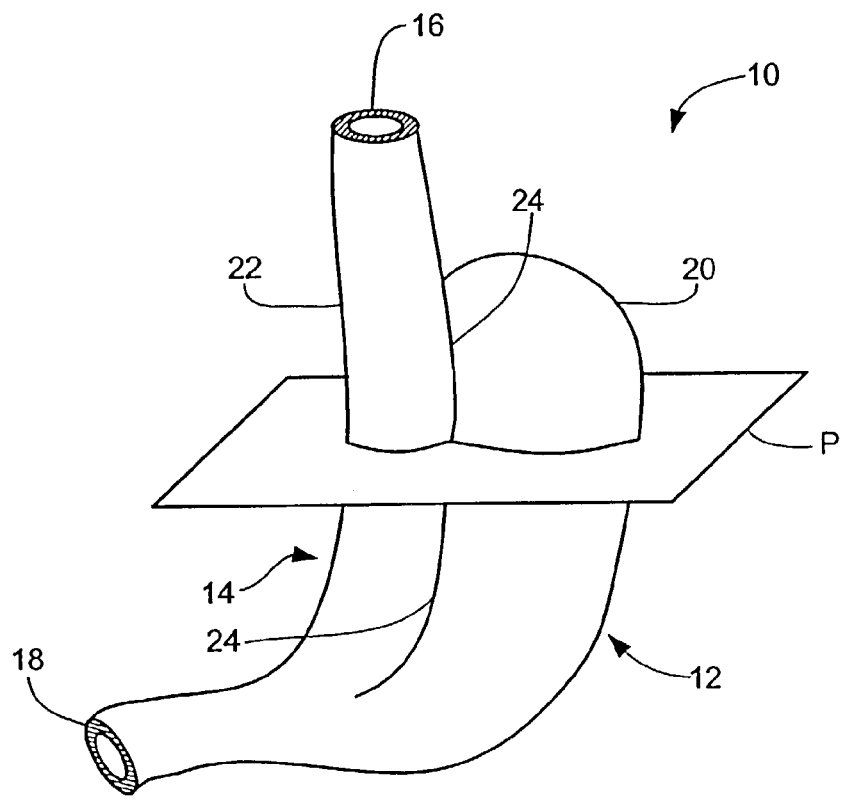
FIG. 1A shows an example of a modified stomach having a smaller pouch created from the interior surface lining.
Figure 1B:
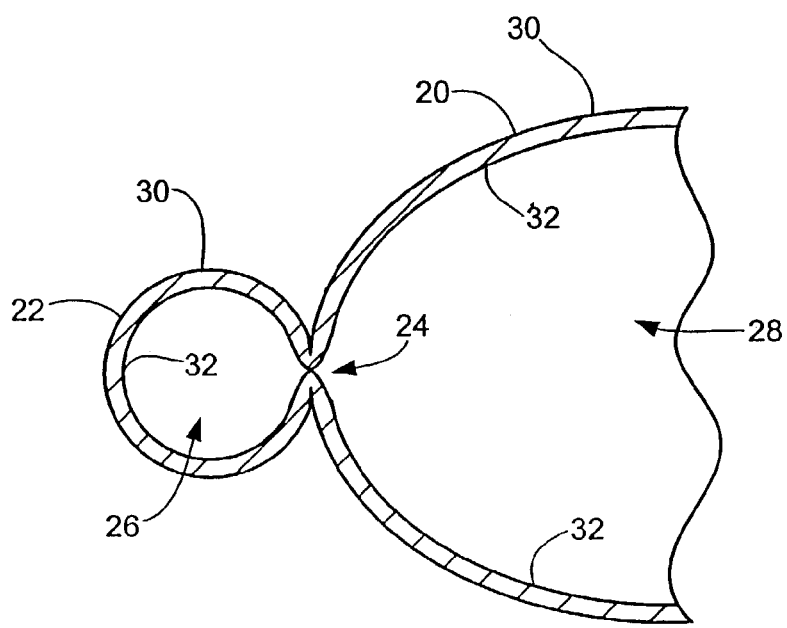
FIG. 1B shows a partial superior view of the cross section from FIG. 1A.

FIG. 1A shows an example of a modified stomach 10 which may be created, by any one of the methods described below, as part of the present invention. Greater curvature 12 and lesser curvature 14 is seen in modified stomach 10, as well as the distal end of esophagus 16 and pylorus 18. As part of the present invention, stomach 10 may be divided along junction 24 into modified pouch 22, which is preferably less than about 1 ounce in volume, and main pouch 20. FIG. 1B shows a partial superior view of the cross section of main pouch 20 and modified pouch 22 as viewed from cutting plane P from FIG. 1A. As seen, modified lumen 26 is preferably formed by junction 24 from main lumen 28 by joining a portion of stomach wall 30. During ingestion of food, modified pouch 22 accepts food from esophagus 16 and preferably passes it directly through modified lumen 26 into pylorus 18. Main pouch 20 may remain intact and function normally, but preferably sees little or no food. Acids and other fluids that may be generated in main lumen 28 may drain through the reduced outlet near pylorus 18 and may pass through the digestive system normally.

Marking Tools and Methods

Figure 2:
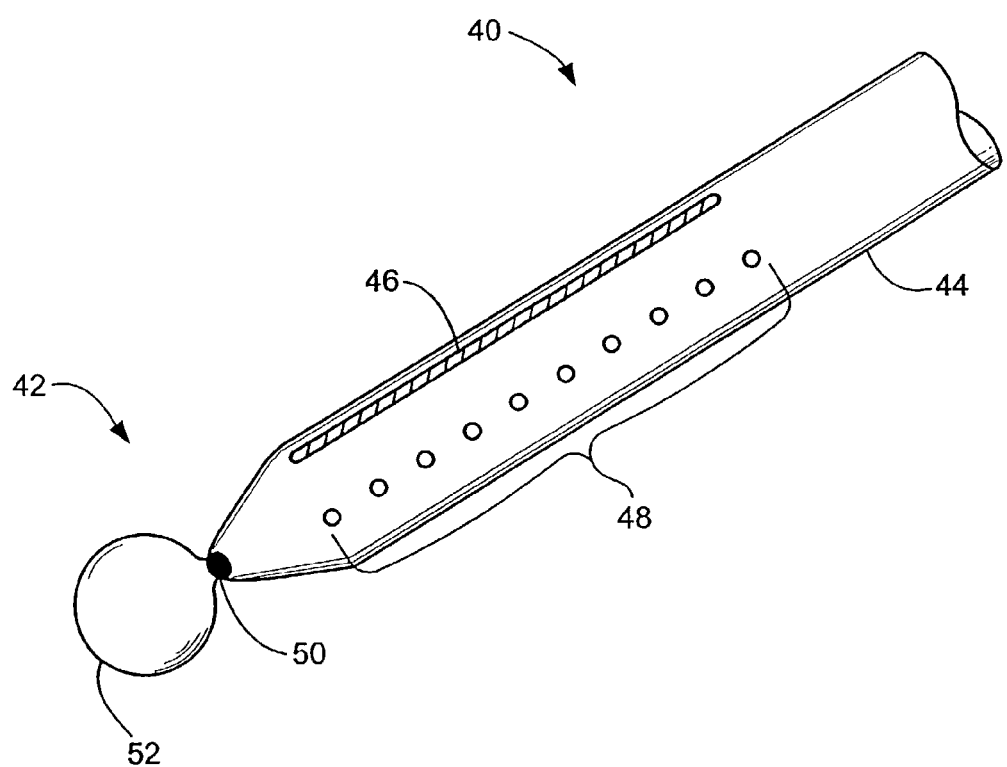
FIG. 2 shows a variation on a marking device or bougie for marking the interior surface of a stomach.

As part of forming a modified pouch, a marking device may be used, preferably at the beginning of the procedure, to create a dye marker "road map" on the interior surface of the stomach from the pylorus to the esophagus. Once such dye marks are placed, they may be visualized, e.g., endoscopically, thereby giving the physician a clear reference point for staple or fixation element placement. An example of such a marking device is shown in FIG. 2 as marking device or bougie 40. Bougie 40 is preferably an elongated device made from tubing member 44 which may have several channels defined within. Tubing 44 may be made from any variety of biocompatible materials, e.g., stainless steel, plastics, etc., and preferably has a diameter and cross section which is similar to that of the finished modified lesser pouch. Along the length may be defined a series of dye ports 46 through which the marking dye may be channeled through from the proximal end of bougie 40. Any variety of biocompatible dyes which preferably enhance visualization may be used, e.g., methylene blue, thionine, acridine orange, acridine yellow, acriflavine, quinacrine and its derivatives, brilliant green, gentian violet, crystal violet, triphenyl methane, bis naphthalene, trypan blue, and trypan red. Also along the length and on either side of dye ports 46 may be a series of vacuum ports 48, which are optional. A distal balloon 52, which may be inserted into the pylorus to stabilize bougie 40 during the procedure, is preferably attached to inflation tip 50 at distal end 42 and may be inflated from the proximal end of tubing 44 by the physician.

Figure 3A:
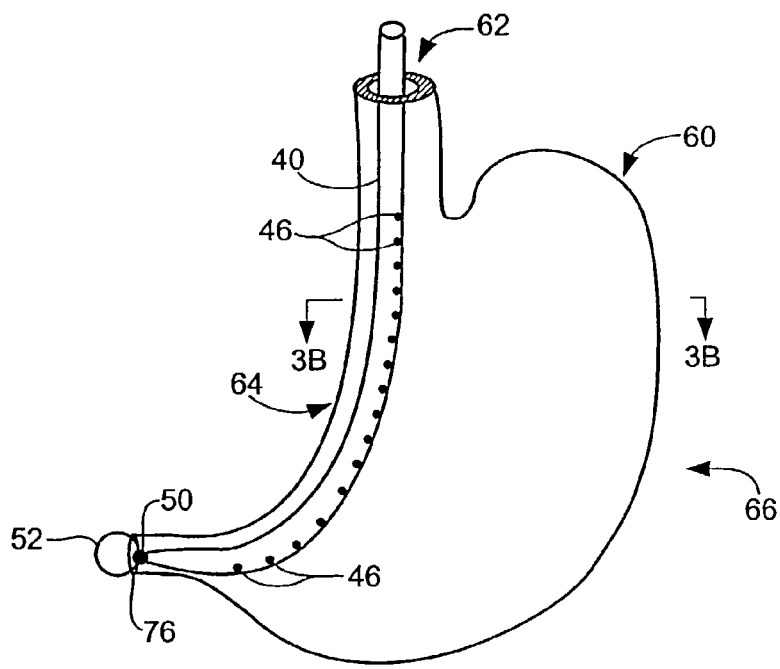
FIG. 3A shows a variation on positioning a marking device inserted into a stomach.
Figure 3B:
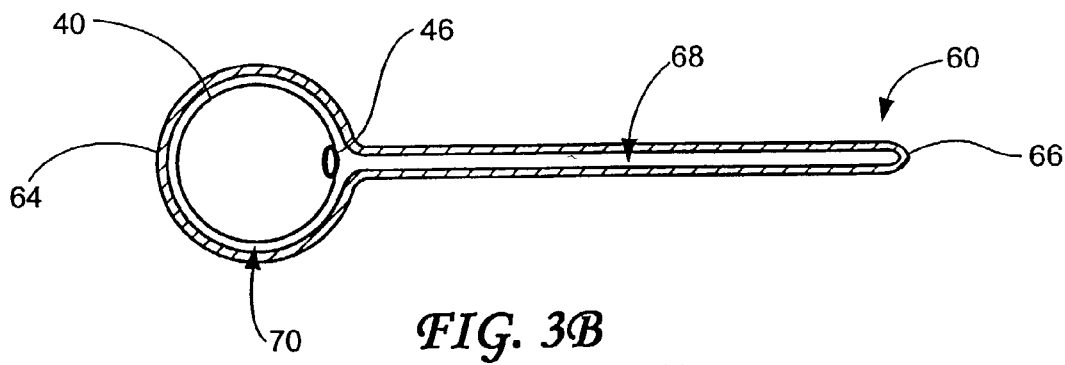
FIG. 3B shows a cross section view from FIG. 3A of a deflated stomach around the marking device.
Figure 3C:
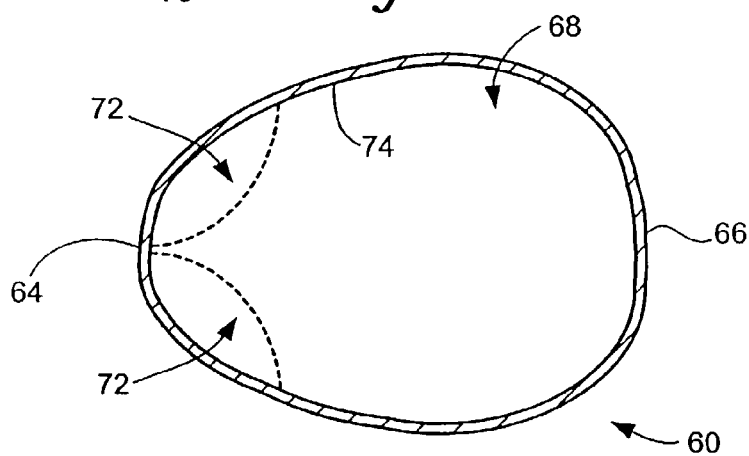
FIG. 3C shows the cross section view from FIG. 3B of an insufflated stomach with the resulting marks.

FIGS. 3A to 3C show bougie 40 during one method of use. FIG. 3A shows stomach 60 as bougie 40 is inserted down through esophagus 62. As bougie 40 is advanced down to pylorus 76, distal balloon 52 may be inflated through inflation tip 50, thus securing the device. Bougie 40 preferably follows lesser curvature 64 and may alternatively be shaped to approximate lesser curvature 64. Bougie 40 is also preferably rotated such that dye ports 46 face away from lesser curvature 64 and face towards greater curvature 66. Then the air and fluids contained within stomach 60 are preferably removed, either through vacuum ports 48, if they are included in bougie 40, or through another vacuum port which may be introduced endoscopically through esophagus 62. FIG. 3B shows cross section 3B-3B from FIG. 3A as deflated stomach 60. Once deflated, modified lumen 70 may take shape around bougie 40, separate from deflated main lumen 68. In this deflated state, the dye may be channeled through dye ports 46, thereby leaving dye marks 72 on interior lining 74. Once the staining has been performed, lumen 68 may be insufflated, as shown in FIG. 3C, and bougie 40 may then be removed. As seen in FIG. 3C, dye marks 72 mark or delineate the junction region where anchors or fasteners may be placed to draw interior lining 74 together to form the modified lumen.

Gastric Reduction Tools and Methods Using Fasteners

One variation of reducing the stomach size involves grasping the interior walls of the stomach, preferably via an endoscope advanced trans-esophageally, and placing one to several fixation elements on opposing interior walls and then bringing those fixation elements together.

Several examples of different possible variations on fasteners are shown and described below. These variations are not intended to be limiting but are merely given as illustrative examples.

Figure 4A:
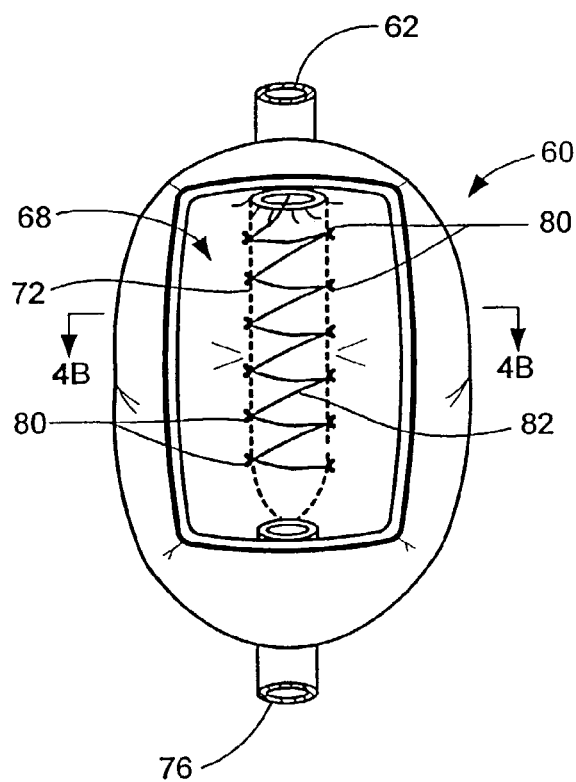
FIG. 4A shows a view of the interior of the lesser curvature of a stomach with anchors attached.
Figure 4B:
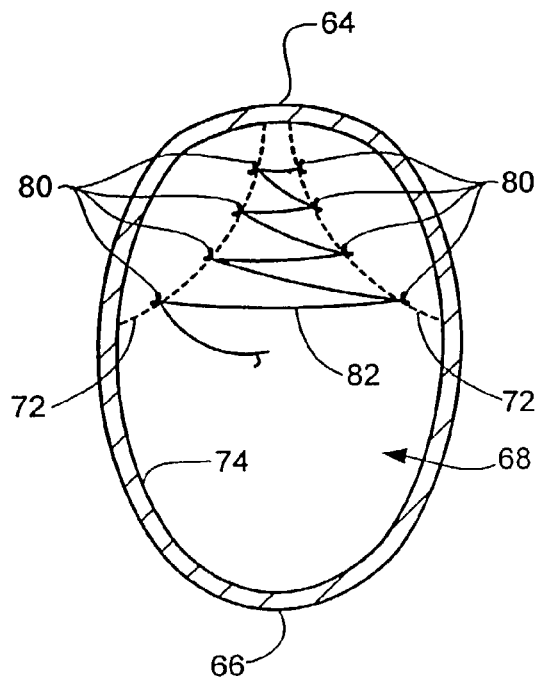
FIG. 4B shows a cross section view from FIG. 4A with the anchors attached.

FIG. 4A shows a view of the interior of the lesser curvature of stomach 60 with part of the greater curvature wall removed. As seen, individual anchors 80 may be secured to the interior surface along the junction 24 where modified pouch 22 from FIG. 1A would form. Anchors 80 may be of any biocompatible material, e.g., stainless steel, polymers, etc., which may be formed into a variety of fasteners, e.g., staples, ratcheted wires, zip ties, clips, tags, eyelets, crimps, and screws. Anchors 80 may be placed by estimating the junction boundary, but they are preferably located along dye mark 72, which may be formed by methods and tools described above, prior to anchor 80 placement, as shown in FIG. 4B, which is cross section 4B-4B from FIG. 4A. After anchors 80 have been fastened, suture 82 may be drawn through each of the anchors 80, preferably in a zig-zag manner, and then suture 82 may be drawn tight to bring the opposing surfaces of interior lining 74 together in apposition along dye marks 72 to form the modified lumen. Alternatively, individual anchors 80 may be preloaded or prefastened by suture 82, and anchors 80 may be fastened to interior lining 74 in this manner.

Figure 5A:
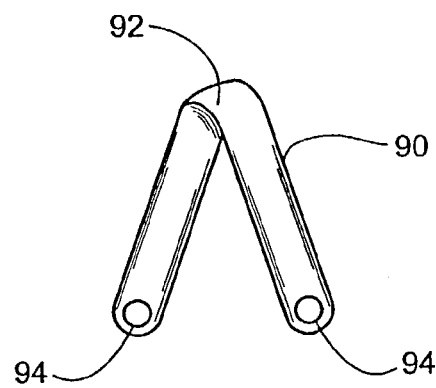
FIG. 5A shows a side view of a crimping variation on a fastening device.
Figure 5B:
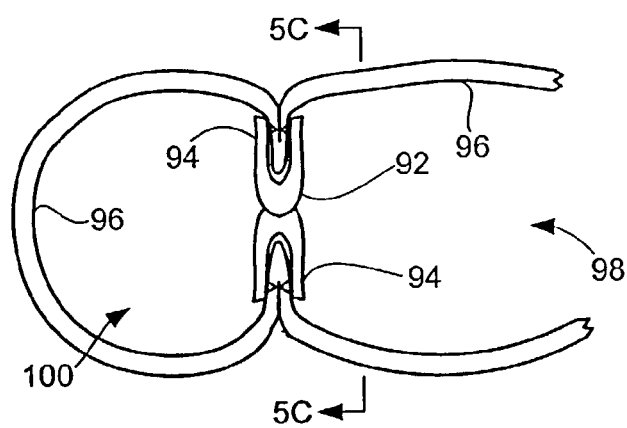
FIGS. 5B and 5C show a superior and side view, respectively, of several interlocked crimping devices from FIG. 5A.
Figure 5C:
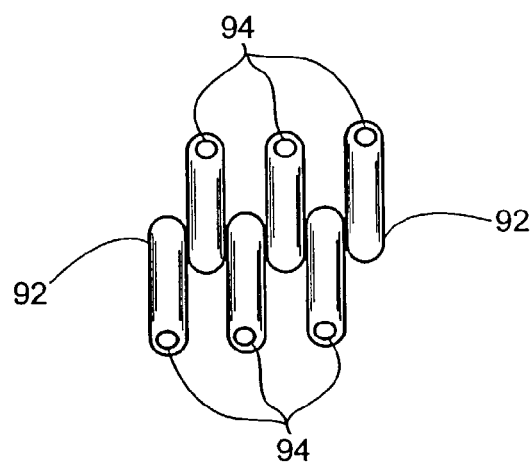

FIG. 5A shows a side view of a variation on a fastening device in crimping member 90. Crimping member 90 is preferably made from a biocompatible material, e.g., stainless steel, nitinol, etc., and may be formed to have elbow 92 extend into two opposing anchoring ends 94. FIG. 5B shows a superior view of a created modified lumen 100 formed from main lumen 98 by any of the methods described herein. In this variation, several crimping members 90 may be attached or fastened to interior lining 96 by anchoring ends 94. As they become attached, each of the members 90 are preferably configured to interlock with an adjacent crimping member 90, much like a zipper. FIG. 5B shows the interlocked members 90 from the top to form lumen 100 and FIG. 5C shows the view from 5C-5C from FIG. 5B where each of the crimping members 90 are shown interlocking at their elbows 92 like a zipper.

Figure 6A:
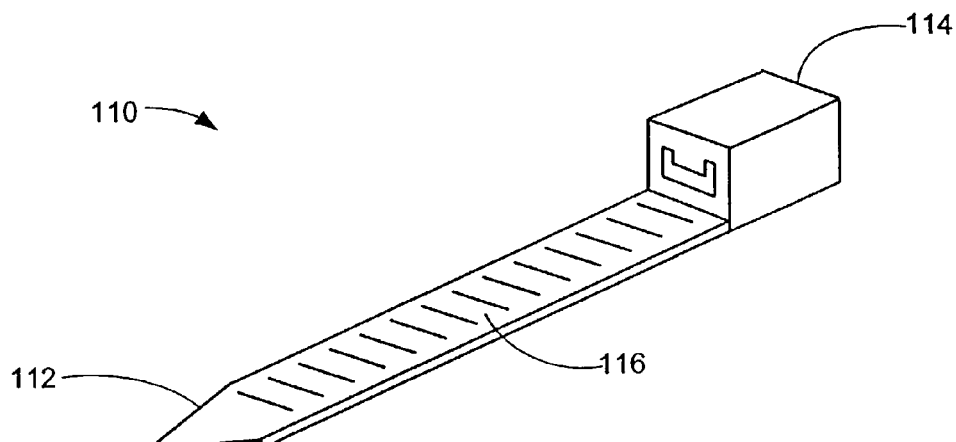
FIG. 6A shows an isometric view of a zip-tie or ratcheted variation on a fastening device.
Figure 6B:
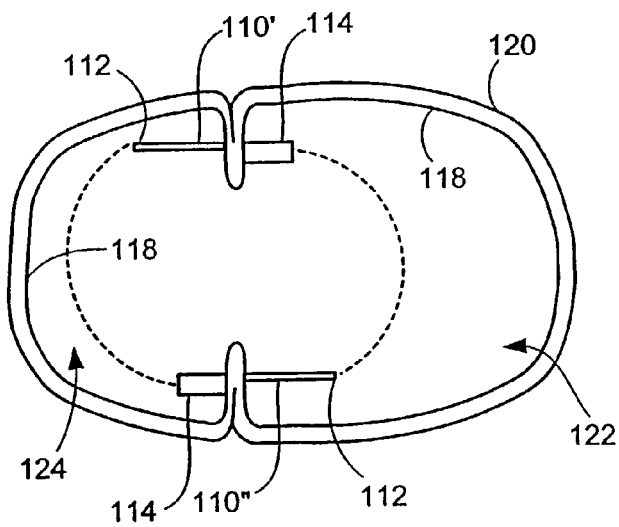
FIG. 6B shows a superior view of the device of FIG. 6A attached to the stomach wall.
Figure 6C:
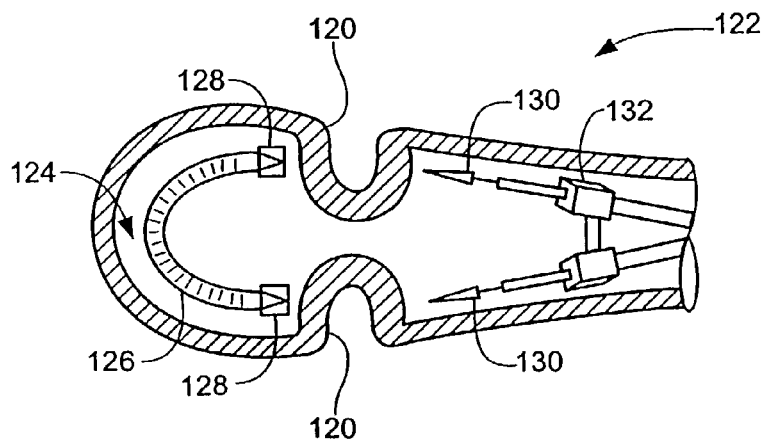
FIG. 6C shows a superior view of another double zip-tie variation on a fastening device.
Figure 6D:
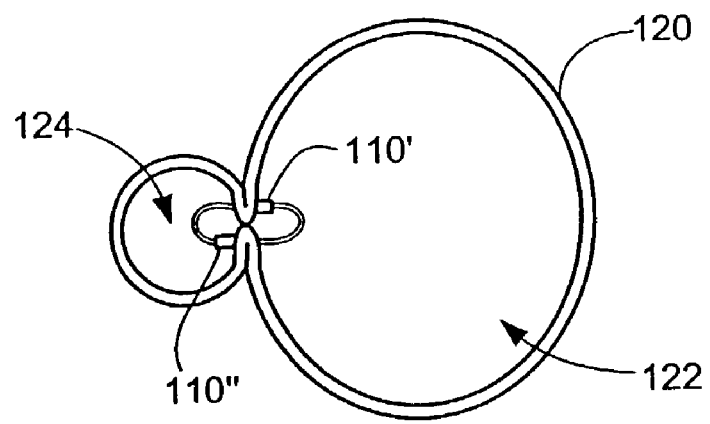
FIG. 6D shows the stomach of FIG. 6B with the fasteners cinched.

FIG. 6A shows an isometric view of another variation on a fastening device in ratcheted wire or zip tie 110. This particular variation shows a distal tip or male end 112 and a corresponding proximal end or female end 114, with ratcheted length 116 between those two ends. FIG. 6B shows a superior view of stomach wall 120 just prior to the formation of modified lumen 124 from main lumen 122. As seen, male end 112 of first zip tie 110' maybe pierced through one side of interior lining 118 and second zip tie 110" may be pierced through the opposing side of interior lining 118 such that the male ends 112 of each zip tie preferably correspond to the female ends 114 of the other zip tie. To then form the lumen 124, each zip tie 110', 110" may be drawn together and tightened accordingly, as shown in FIG. 6D. A plurality of zip ties 110 are preferably used to form modified lumen 124 by aligning them by any of the methods described above.

Figure 6E:
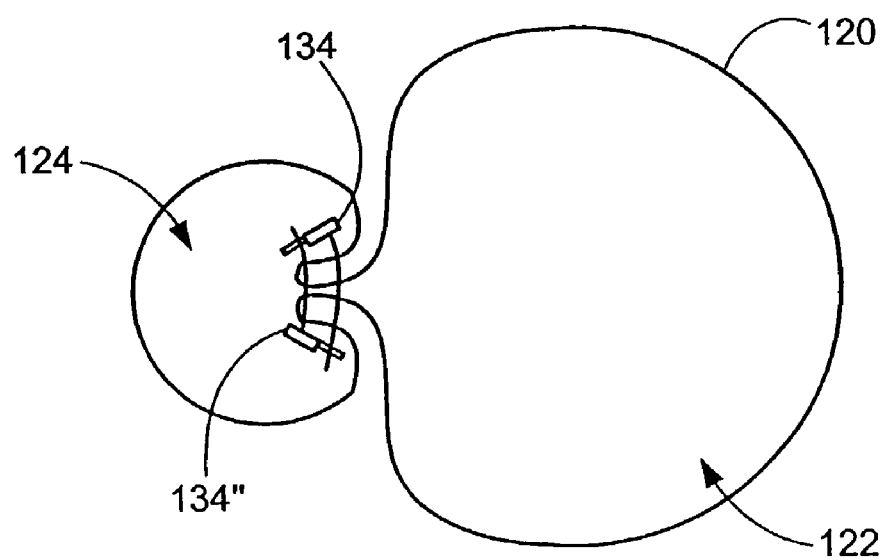
FIG. 6E shows a superior view of another perpendicular zip-tie variation on a fastening device.

An alternative zip tie device which may be used is a perpendicular type version of zip tie 110. As shown in FIG. 6E, first perpendicular zip tie 134' and second perpendicular zip tie 134" may be used in place of zip tie 110 and lumen 124 may be formed in much the same manner as described above to result in the modified stomach as shown in FIG. 6E. A further alternative is shown in FIG. 6C where male zip tie 126 preferably has dual piercing male ends with catcher tubes 128. In this variation, a vacuum-type device, as described below in detail, or forceps may be used to draw portions of stomach wall 120 in apposition. As the apposed stomach walls 120 are positioned, needles 130, which are preferably passed through a double female zip tip 132, may be used to pierce through tissue 120 and lock into catcher tubes 128. Needles 130 may then be drawn back through tissue 120, while simultaneously pulling male ends/catcher tubes 128 back through tissue 120 and into the corresponding double female zip tie 132. The locked zip tie 126 may then be drawn tight against female zip tie 132, trimmed, and then released. This procedure may be repeated for any number of zip ties which may be used to draw the stomach lining together to form the smaller pouch and may also be used with the dye marking device 40 and procedure as described above.

A further variation on the individual anchoring fasteners is shown in FIG. 7A. This variation shows gasping device 140 with retaining tube 142 and extendable members 146 which may extend from distal opening 144. Extendable members 146 are preferably made from a biocompatible material, e.g., superelastic or shape memory alloy such as nitinol, which may be biased to urge away from a longitudinal axis defined by tube 142 once extended beyond distal opening 144. As members 146 extend, they may reach out to grasp apposed portions of interior lining 150 by hooks 148. As above, the locations where hooks 148 grasp may be defined by the marking device as described above and viewed by the physician through, e.g., an endoscope. Once hooks 148 have grasped the appropriate portion of lining 150, members 146 may then be drawn back through distal opening 144, as shown in FIG. 7B, and a retaining device, such as crimp 152, may be slid over a distal section of members 146, as shown in FIG. 7C, to maintain the position of hooks 148 and apposed lining 150 to create the desired lumen.

Gastric Reduction Tools and Methods Using Stapling Devices

Figure 8A:
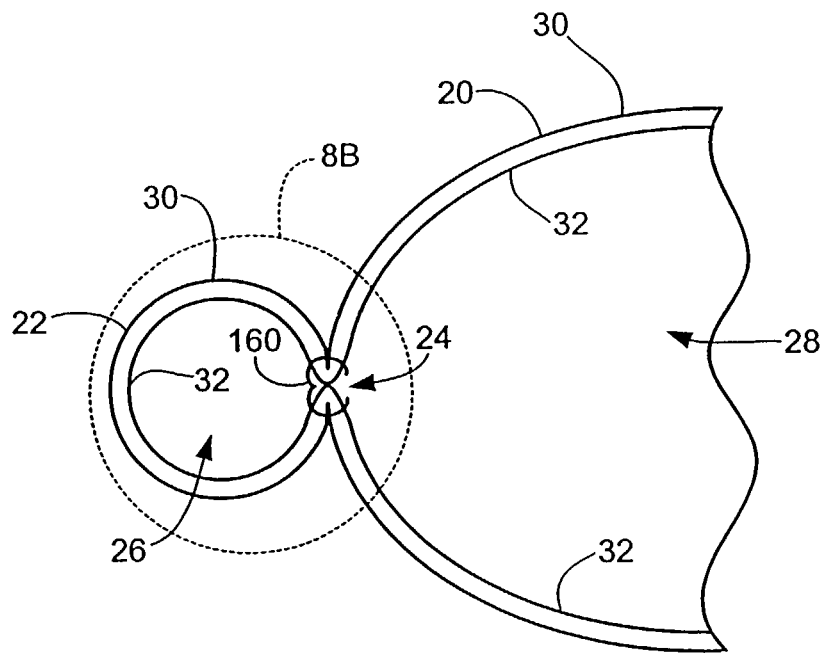
FIGS. 8A and 8B show a superior view of a modified stomach maintained by a fastening staple.
Figure 8B:
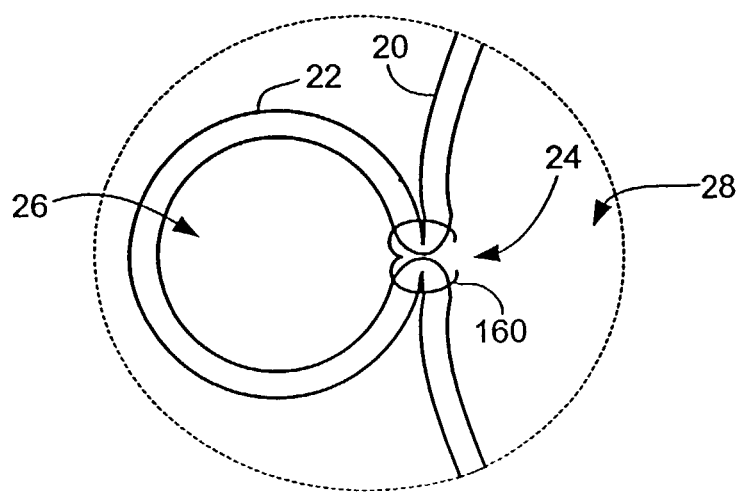

Aside from individual anchoring and fastening devices, the stomach pouch may be modified and/or created by a variety of other device variations utilizing other methods. FIG. 8A shows the cross sectioned superior view of FIG. 1B with the addition of staple 160 maintaining junction 24. The figure shows an example of how, e.g., an endoscopically applied stapler, may be used to retain and hold junction 24 to form modified lumen 26. FIG. 8B shows a close-up view of the junction 24 and staple 160 which was applied from within lumen 26.

To staple opposing sides of a stomach together to form two separate lumens from within the interior surface of the stomach, an endoscopic stapling device may be used to accomplish such a task. Such an endoscopic stapler preferably brings two regions of tissue into apposition and may then apply a fastening element, e.g., staples, clips, tags, etc., into the two regions of tissue to affix them together. These stapling devices may optionally incorporate the use of the marking device or bougie 40, as described above, as a preliminary step as a guide to vacuum placement and/or stapling to form the desired modified lumen. The fastening elements, e.g., staples, are preferably made of a biocompatible material such as stainless steel, titanium, polymers, sutures, nitinol, or any other similar metals and alloys, etc. and may be in any conventional shape such as C-shaped and U-shaped staples or any of the other shapes as described herein. The two regions of tissue may be adhered to the stapling device by a variety of attachment methods, e.g., tines, barbs, hooks, vacuum, or any combinations thereof. In an adhering device utilizing a vacuum to hold the apposing regions of tissue together, such a device may be a tubular or wand-shaped member and preferably has at least two windows which may be spaced about the circumference of the tube or wand. These windows may be separated by an arc in a range of about 20° to 180° about the longitudinal axis defined by the length of the tube or wand, and are preferably separated by an arc in a range of about 90° to 180°.

Several examples of different possible variations on the stapling device are shown and described below. These variations are not intended to be limiting but are merely given as illustrative examples.

Figure 9A:
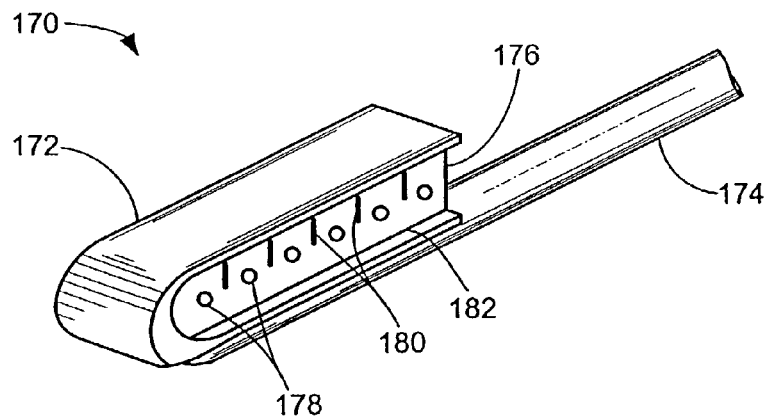
FIGS. 9A and 9B show isometric views of a variation on an endoscopic stapling device.
Figure 9B:
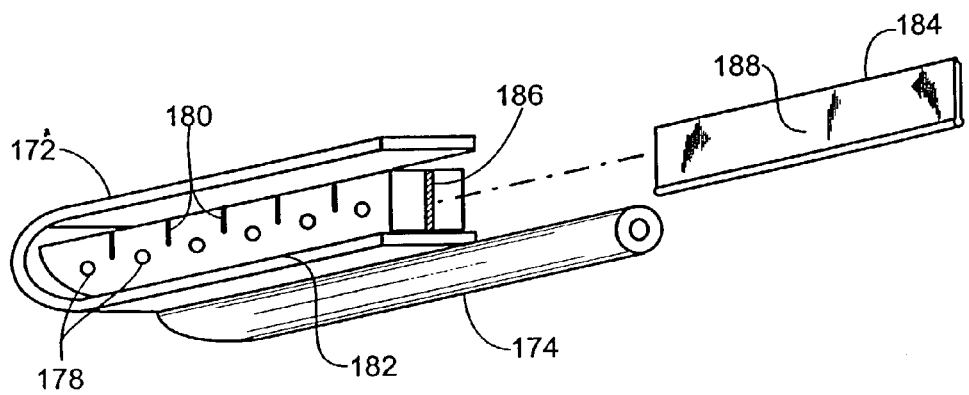

FIG. 9A shows a variation of an endoscopic stapling device in the isometric view of anvil stapling device 170. Stapling unit 172 is shown attached to the distal end of tube 174. Within stapling unit 172 is staple enclosure 176 where staples may be loaded and vacuum ports 178 which are seen in an alternating fashion with staple slots 180, through which the staples may be deployed. FIG. 9B shows a reverse isometric view of the device of FIG. 9A. As seen, stapling unit 172 may have septum 184 insertable into septum slot 186, which is preferably midway between the sides of staple enclosure 176 and which may separate the interior of staple enclosure 176 into two separate chambers. Septum 184 may serve several functions, one of which may be to allow selective activation of opposing sides of vacuum ports 178 of unit 172 as tissue is selectively adhered to the device. Other functions of septum 184 are discussed below.

In operation, stapling unit 172 may be inserted transesophageally into a stomach and a first portion of the interior lining may be adhered to a single side of staple enclosure 176 through a vacuum created within vacuum ports 178. The vacuum may be created in stapling unit 172 through tube 174 and activated from the proximal end of tube 174 from outside the patient's body. Once the first portion of the interior lining is adhered to one side of staple enclosure 176, the opposite set of vacuum ports 178 may be activated and unit 172 may be used to draw the first portion to an opposing second portion of the interior lining, which may then be adhered to the device such that the first portion and the second portion are preferably in apposition to each other. This action preferably forms the modified lumen 26 of FIGS. 8A and 8B. As the tissue is held to unit 172, septum 184 may be withdrawn from septum slot 186 by introduced forceps through, e.g., an endoscopic or through an integral actuator, to form a single chamber within staple enclosure 176. Removal of septum 184 may then bring the first and second portions of tissue into contact apposition. The side surfaces 188 of septum 184 may incorporate a cutting, abrading, scoring, heating, freezing, chemically damaging, or some other damaging surface to tissue. Such a surface 188 may damage the interior lining contacting each other upon removal of septum 184 as surface 188 slides past. This damage may encourage a more vigorous healing response and a more permanent fixation between the damaged tissue once stapled or affixed together.

After removal of septum 184, the staples loaded within staple enclosure 176 may be fired through staple slots 180 to affix the tissue. As the staples are fired, anvil 182 may be used as an anvil to secure the staples to the tissue, thereby resulting in the modified lumen 26 as shown in FIG. 8B. The length of stapling device 170 may be made according to the desired junction length and the size of the patient's stomach. This particular variation may be withdrawn from the area after the stapling procedure by first pushing the stapling device 170 past the resulting staple line.

Figure 10:
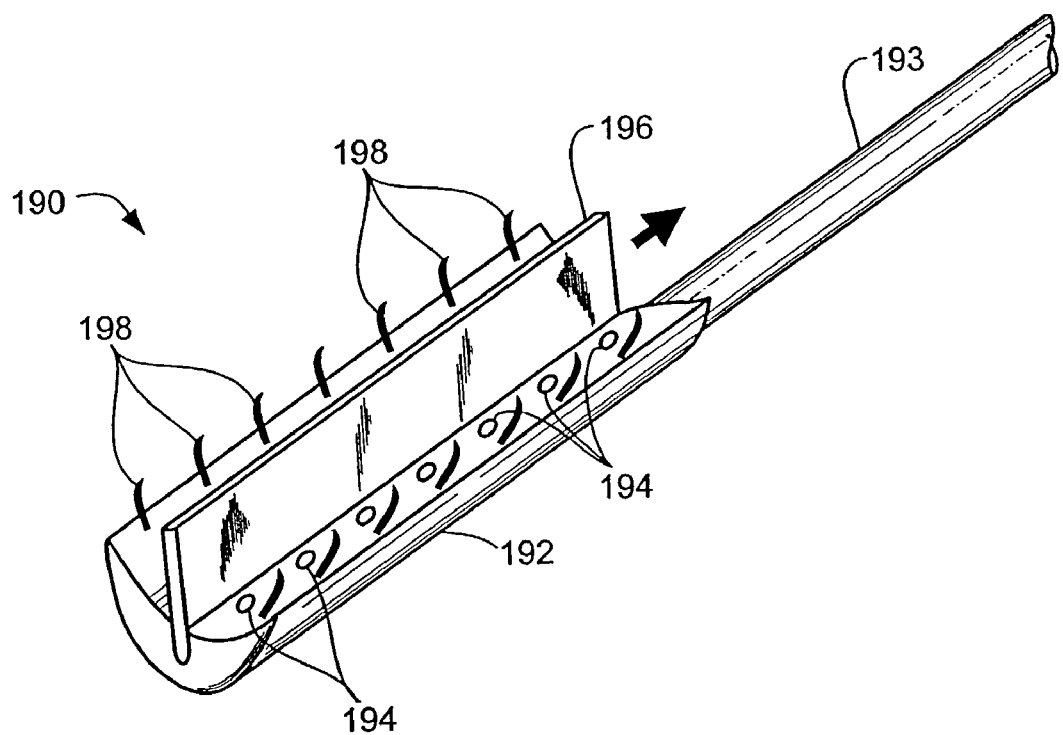
FIG. 10 shows an isometric view of a variation on a box stapling device.

FIG. 10 shows an isometric view of another variation in box stapling device 190. Stapling unit 192 is shown as being attached in fluid communication to vacuum tube 193. Stapling device 190 may be inserted and operated in the same manner as device 170 described above. Stapling unit 192 may have vacuum ports 194 activated selectively on either side of septum 196 as described above. The tips of staples 198 are shown partially deployed for illustration purposes, but are preferably not deployed until septum 196 is first retracted preferably in the direction as indicated. Septum 196 may also be configured to damage the contacting tissue upon septum 196 withdrawal in the same manner as described above. Stapling device 190 may be easily applied and removed after staples 198 have been deployed.

Figure 11A:
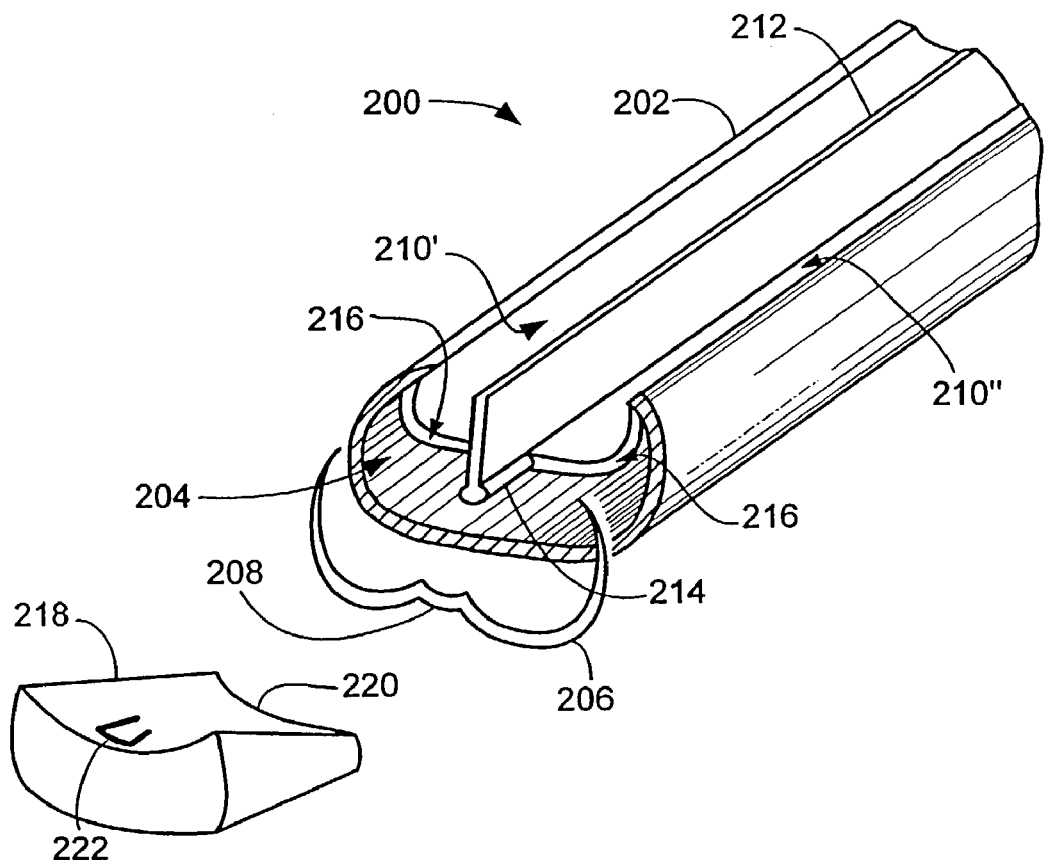
FIG. 11A shows an assembly view of another stapling device variation.
Figure 11B:
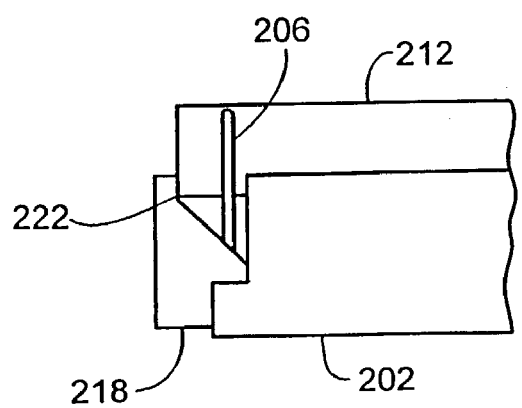
FIG. 11B shows a side view of the device of FIG. 11A.

FIG. 11A shows an assembly isometric view of another variation in stapling device 200. This variation 200 shows curved tube 202 which may have lumen 204 house staples 206 as well as act as a combination vacuum and staple slot 216. Tube 202 may be shaped in a variety of ways but is shown here as a C-shaped or U-shaped tube with first channel 210' and second channel 210", for adhering the two apposed portions of tissue, preferably separated by removable septum 212. With this variation 200, tissue may be adhered within the channels 210', 210" through vacuum/staple slot 216 and once positioned, staples 206 may be deployed while septum 212 is removed simultaneously by the use of curved wedge 218. In operation, curved wedge 218 may be drawn within lumen 204 from the tube 202 distal end to the proximal end by, e.g., a pull-wire attached to wedge 218. As wedge 218 is advanced proximally, wedge 218 would preferably force pivot 208 of staple 206 against contact edge 214 of septum 212. As wedge 218 is advanced further proximally, urging end 220 may then urge the curved ends of staple 206 to rotate about pivot 208 and deploy through slot 216. While staple 206 is deploying, notch 222, preferably located at a distal end of wedge 218, may engage contact edge 214 and begin to slide septum 212 simultaneously towards the proximal end of tube 202. FIG. 11B shows a side view of stapling device 200 of FIG. 11A. As seen, curved wedge 218 preferably contacts septum 212 via notch 222 and pushes while simultaneously urging staple 206 to deploy. The figures show a single staple 206 for illustrative purposes only and any plurality of staples 206 may be used in practice depending upon the desired results.

Figure 12A:
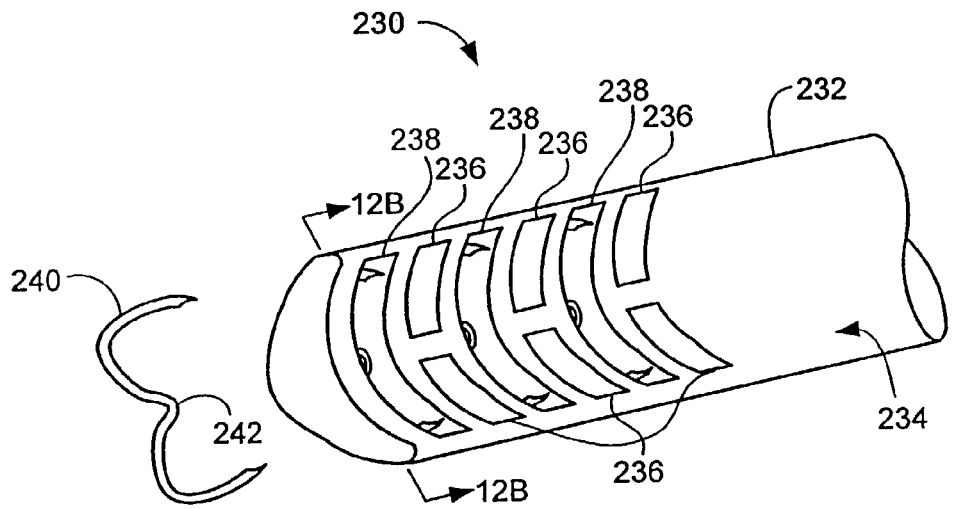
FIG. 12A shows an isometric view of a crescent shaped variation of a stapling device.
Figure 12B:
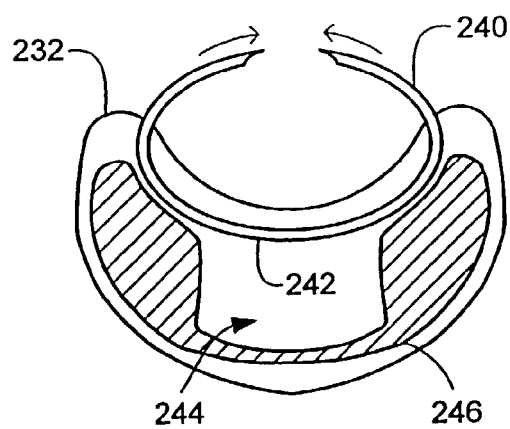
FIG. 12B shows an end view of the device of FIG. 12A showing a staple deploying.
Figure 12C:
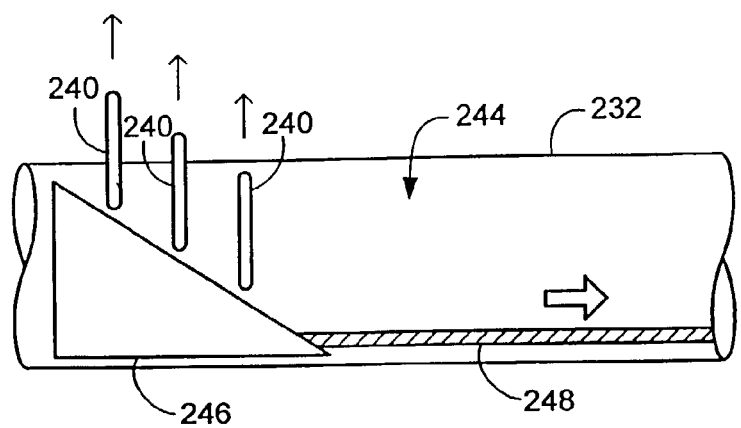
FIG. 12C shows an interior side view of the device of FIG. 12A with a translating wedge sequentially deploying staples.

FIG. 12A shows an isometric view of yet another variation in stapling device 230. This variation may omit a removable septum. Curved tube 232 is preferably curved in this variation in a crescent shape forming contact channel 234. Within contact channel 234, a number of vacuum ports 236 and staple slots 238 may be defined in an alternating pattern, as shown. A possible W-shaped staple 240 preferably having pivot 242 at the staple 240 midpoint is shown outside of tube 232 for illustrative purposes in a possible orientation for insertion within staple slots 238. FIG. 12B shows cross section 12B-12B from FIG. 12A. As seen, tube 232 defines lumen 244, which preferably runs the length of tube 232, and translating wedge 246 which is preferably slidingly disposed within lumen 244. As seen in FIGS. 12B and 12C, which is a side view of the interior of tube 232, wedge 246 may be translated by pull-wire 248. Pull-wire 248, which may be made of any high-strength material, e.g., stainless steel, nitinol, nylon, polymers, etc., may be manipulated by a physician from the proximal end of tube 232 from outside of the patient's body. Like the device 200 of FIGS. 11A and 11B, once vacuum ports 236 have acquired the interior tissue lining to be approximated, translating wedge 246 may be advanced proximally. Advancing wedge 246 may urge staples 240 to deploy through staple slots 238 sequentially as shown to hold the tissue and form the desired lumen.

An example of deployment for any of the stapling devices described above is shown in FIG. 13. As shown, stomach 250 with the wall partially cut out is seen with stapling device 252 inserted within. Stapling device 252 is shown merely as an example of insertion and could comprise any of the devices described herein. Device 252, which is preferably advanced trans-orally into stomach 250 and through esophagus 256, is preferably located at the distal end of delivery/vacuum tube 254. Once inserted, device 252 may be located by the assistance of the lesser curvature 258 of stomach 250. Also shown are vacuum/staple ports 260, which may be any of the configurations as described herein. In a preferable variation, stapling device 252 may be configured to produce a staple line or junction following the lesser curvature beginning from cardiac notch 264 down towards pylorus 262. Accordingly, device 252 may have the length and vacuum/staple ports 260 configured such that the distal end of device 252 points towards pylorus 262.

Figure 13:
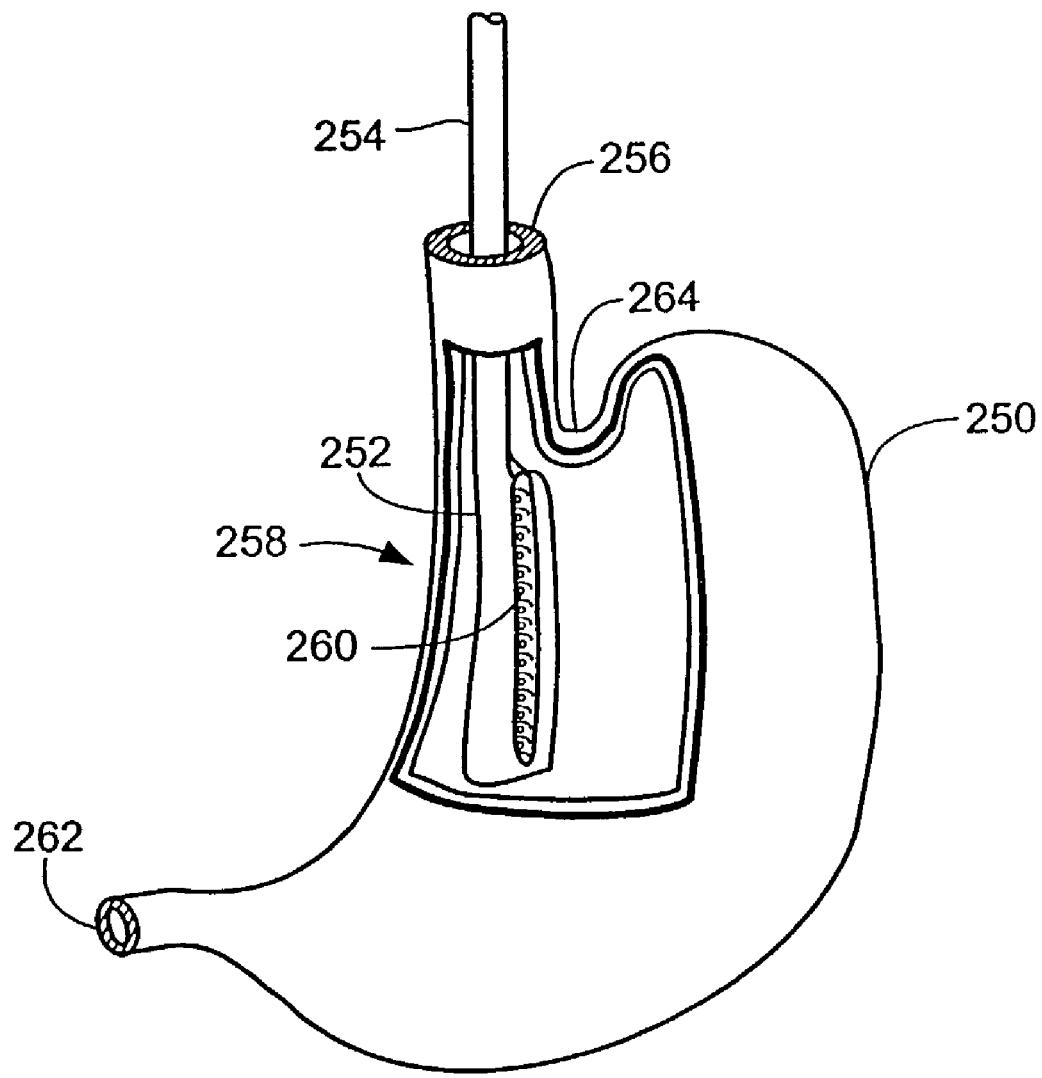
FIG. 13 shows an interior view of a stomach with an example of stapling device placement.
Figure 14:
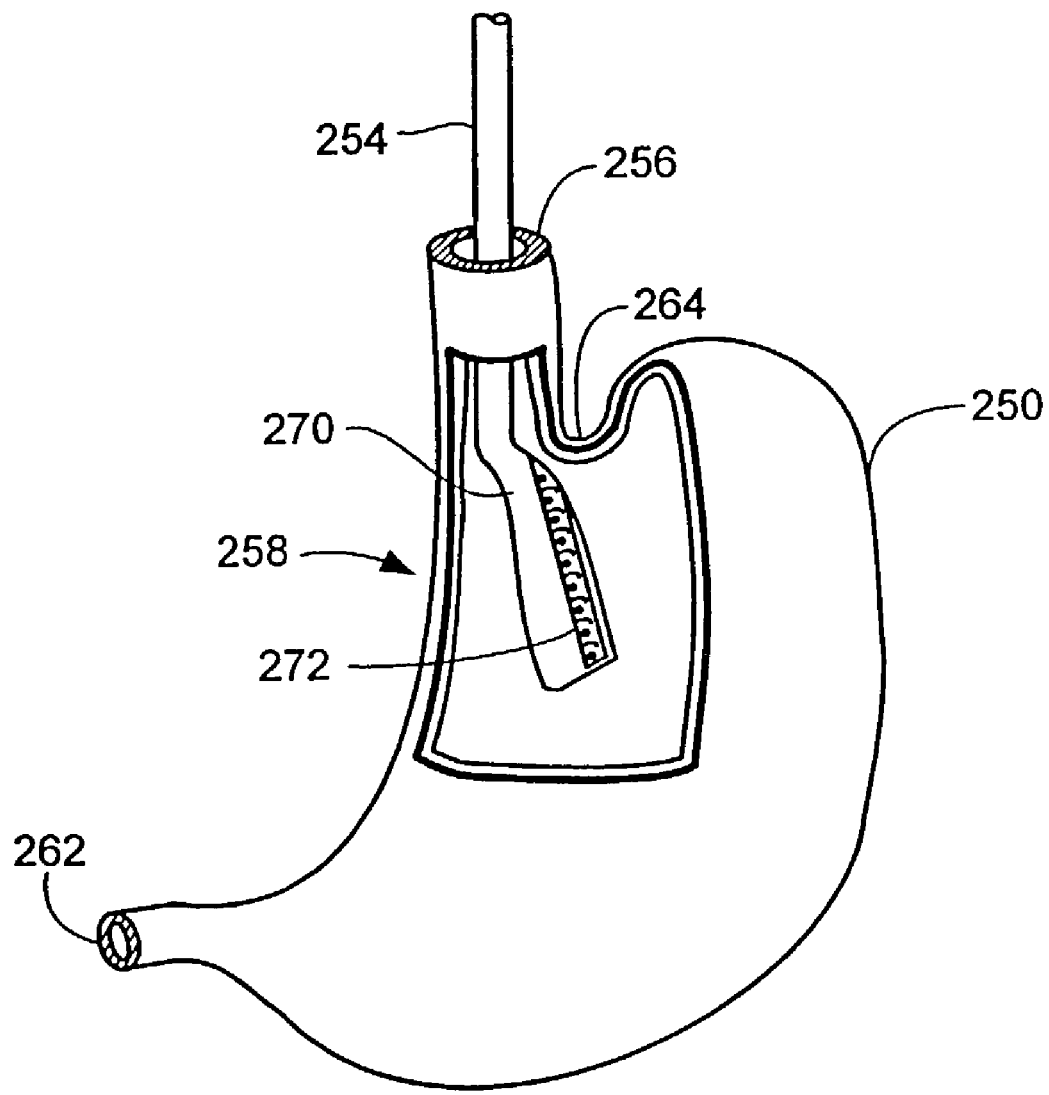
FIG. 14 shows an interior view of a stomach with an example of a modified stapling device which may be used for the treatment of GERD.

FIG. 14 shows stapling device 270 in a slightly different configuration for the treatment of other gastro-intestinal diseases such as gastroesophageal reflux disease (GERD), as discussed above. The stomach 250 of FIG. 13 is shown, but for the treatment of GERD, stapling device 270 may be slightly modified such that the device 270 and vacuum/staple ports 272 may be straight or flared away from, rather than towards, lesser curvature 258 and pylorus 262 as described above. As such, vacuum/staple ports 272 would preferably produce a staple line or junction beginning from cardiac notch 264 and then flares away from lesser curvature 258 and pylorus 262. Device 270 may be any of the devices described and operated herein, but for the flared modification. Likewise, any of the devices described herein may be used for the treatment of GERD by simply angling the device to produce a flared staple line. Alternatively, a simple non-flared staple line may also suffice for treating GERD. The staple line may act as a Heimlich valve which preferably closes down in response to pressure exerted from the greater or main lumen. Moreover, the smaller volume of the modified lumen in-line with esophagus 256 may provide a smaller volume of acid available for esophageal reflux.

Figure 15A:
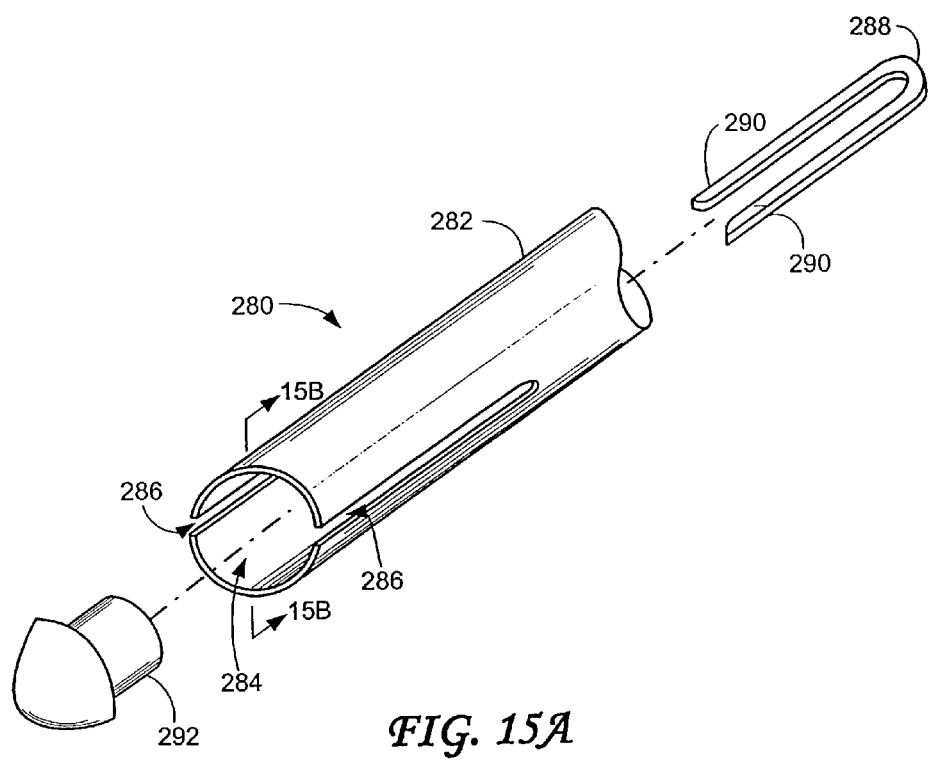
FIG. 15A shows an assembly view of a variation on an approximating device.

An isometric view of a single channel vacuum device variation is shown in FIG. 15A in approximating device 280. Tube 282 is preferably a tubular device which may be inserted into a stomach through the esophagus of a patient. A lumen 284 may run through tube 282 from a proximal end to the distal end of tube 282. At the distal end, two or more windows or slots 286 are preferably defined opposite of one another, as shown. The lengths and widths of slots 286 may vary and is preferably long enough to approximate the desired length of the boundary or junction line of the modified lumen; likewise, the width is preferably wide enough to accommodate at least two layers of the stomach interior lining. Approximating clip 288 is shown having at least two piercing ends 290 and may be loaded into tube lumen 284 from either the proximal end or distal end of tube 282 preferably prior to inserting the device 280 into the patient. Clip 288 is preferably made of a biocompatible material as described above. Biodegradable plug 292 may be placed into the distal end of tube 282 prior to insertion into the patient and is preferably made of a biocompatible biodegradable material, e.g., biodegradable polymers such as polylactide, polyglycolide, and their copolymers. Plug 292 may be alternatively made from a non-biodegradable material and may simply pass after the procedure. Plug 292 may aid in maintaining a vacuum seal through slots 286 during the approximation procedure, as described below.

Figure 15B:
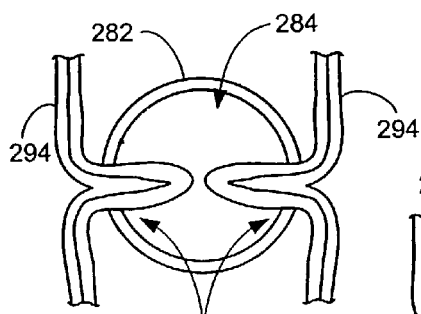
FIGS. 15B to 15D show the process of invaginating stomach interior lining and fastening using the device of FIG. 15A.
Figure 15C:
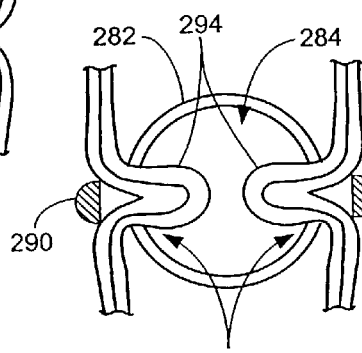
Figure 15D:
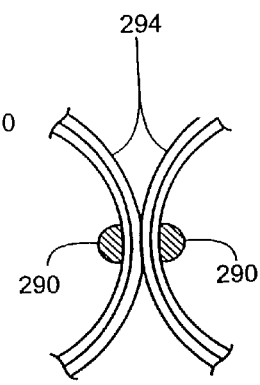

FIG. 15B shows an end view from section 15B-15B from FIG. 15A of tube 282 in operation. As shown, opposing portions of stomach interior lining 294 may be drawn into lumen 284 through opposing slots 286 by creating a vacuum within lumen 284. Approximating clip 288 may be urged distally through tube 282 such that each of ends 290 may be drawn through a corresponding slot 286 over and/or pierced through lining 294 within lumen 284. As lining 294 is approximated within lumen 284, biodegradable plug 292 may become invaginated within lining 294. Accordingly, as clip 288 and ends 290 are positioned over lining 294, tube 282 may be withdrawn from the area while clip 288 preferably slides through the distal end of tube 282 leaving the approximated interior lining 294 held in position by ends 290, as seen in FIG. 15D. Removal of tube 282 may urge plug 292 to slide off the distal end of tube 282 and remain within the newly formed lumen to become degraded over time or to pass through the patient's system.

FIG. 15E shows the device of FIG. 15A, but in this variation, clip 288 may be replaced by screw 289, which is preferably in the shape of a helix or coil having a tapering width or diameter. The first few turns or coils of screw 289 may have the same or similar diameter than the remaining tapering coils; this may enable piercing end 291 to engage interior 294 and may also allow screw 289 to be advanced at the desired orientation through the tissue. Screw 289 preferably maintains a parallel orientation with tube 282 during delivery into the tissue, i.e., a longitudinal axis defined by screw 289 is preferably parallel, or close to parallel, with the longitudinal axis defined by tube 282. Moreover, the outer diameter of the first few turns or coils are preferably the same diameter, or slightly less than, the inner diameter of tube 282. This may further enable screw 289 to be advanced through lumen 284 at the proper orientation prior to engaging interior 294.

Figure 15F:
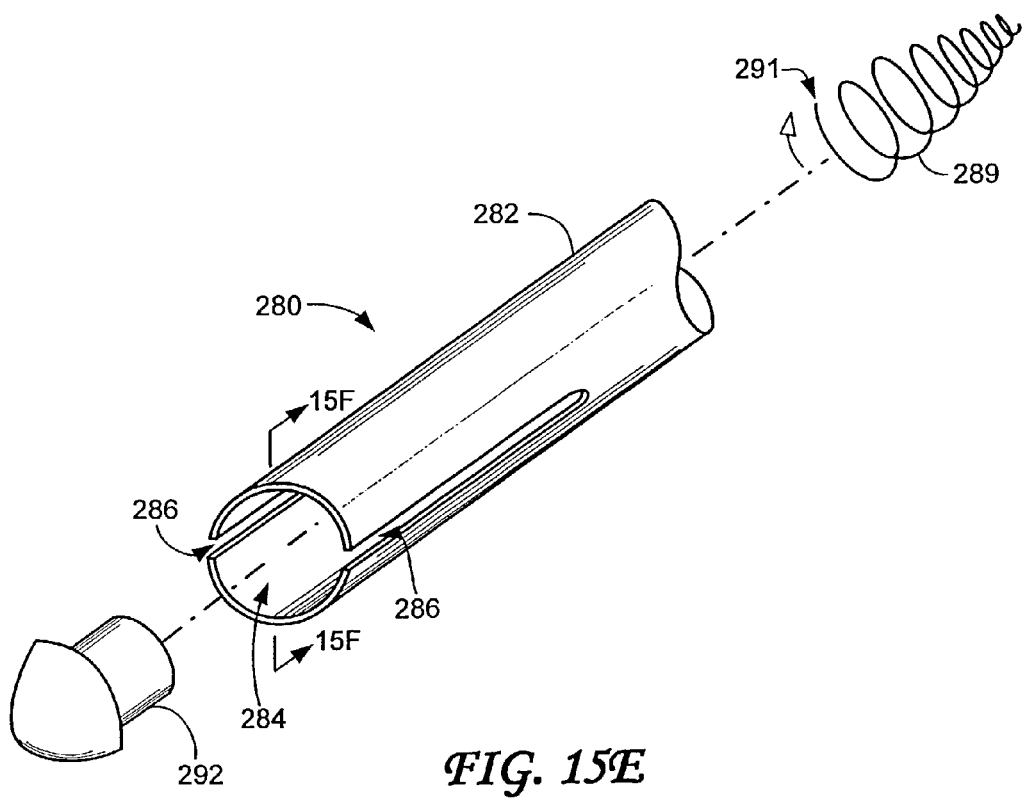
FIGS. 15F to 15H show the process of invaginating stomach interior lining and fastening using the device of FIG. 15E.
Figure 15F:
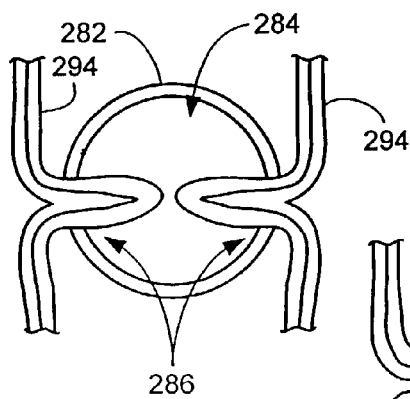
Figure 15G:
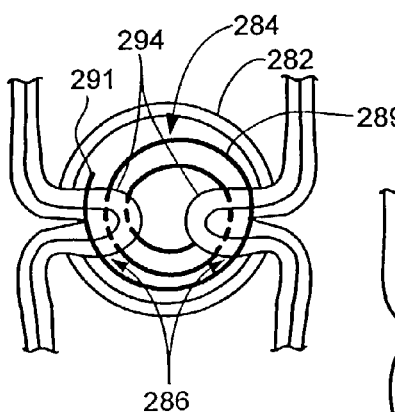
Figure 15H:
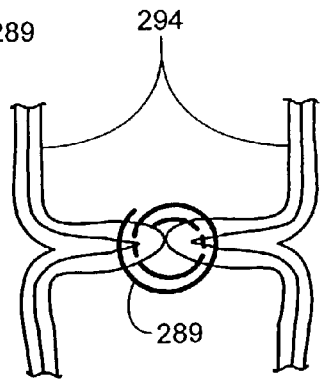

As described above for the device of FIGS. 15A to 15D, opposing portions of stomach interior lining 294 may be drawn into lumen 284 through opposing slots 286 by creating a vacuum within lumen 284, as shown in FIG. 15F. Screw 289 may then be urged through lumen 284 and rotated in the direction of the arrow shown until piercing end 291 engages the invaginated lining 294. Piercing end 291 preferably is sharp and needle-like to enable piercing through multiple layers of lining 294. As screw 289 is further rotated, it may be further advanced distally through the remaining portion of invaginated lining 294. The tapering diameter and decreasing width may also begin to further approximate the opposing edges of lining 294 towards one another, as shown in FIG. 15G. Finally, as seen in FIG. 15H, further advancement of screw 289 preferably draws the opposing surfaces into contact with one another. Tube 282 may then be removed, as described above. Although the fixation of one screw 289 is described, multiple screws 289 may be fastened one after another to form a continuous fixation line.

Screw 289 may be made of a bioabsorbable or biocompatible material, as described herein such as a polymer or superelastic alloy, and may be integrally formed with barbs or whisker-like filaments protruding along its length to help prevent screw 289 from backing out once it has been engaged within the lining 294. An example of a spiraling suturing needle or screw which may be used in this variation is shown and described in U.S. Pat. No. 5,330,503 to Yoon, which is incorporated herein by reference in its entirety. Another example of a helical fastener or screw and applicator which may be used in this or another variation is shown and described in U.S. Pat. No. 5,582,616 to Bolduc et al., which is also incorporated herein by reference in its entirety. Other examples of helical fasteners or screws and applicators are also shown in U.S. Pat. No. 5,810,882; U.S. Pat. No. 5,824,008; and U.S. Pat. No. 5,964,772; all to Bolduc et al., each of which is incorporated herein by reference in their entirety.

Gastric Reduction Tools and Methods Using Rotatable Devices

Aside from endoscopically applied stapling and clip devices, rotating and rotatable probes may also be used to form a modified smaller lumen within a main lumen. Such probes generally may be inserted into a stomach endoscopically and may engage a portion of the interior lining of the stomach and may then be rotated to roll the engaged portion of the stomach wall around the probe itself to bring the wall in apposition with another portion of the stomach wall. Such rotating probes may be used to create a blind-ended pouch of stomach within the main stomach lumen, or as with the other devices, may be used to create a smaller pouch exiting into the pylorus. Once the roll of stomach wall is brought into apposition, a row or a plurality of fasteners, e.g., staples, blind staples, clips, tags, adhesives, etc., may be used to maintain the stomach. The tubes themselves may be made of any variety of biocompatible materials which preferably have sufficient strength to undergo a torsional load, e.g., stainless steel, nickel, platinum, etc.

An example of a stomach modified by such a rotating probe or device is shown in FIG. 16A. Main pouch 300 is seen with modified pouch 302 formed along the lesser curvature of the stomach and delineated by junction 304. This example shows modified pouch 302 extending from esophagus 306 and terminating in pouch opening 308 proximally of pylorus 310. Pouch opening 308 may also be made to terminate at pylorus 310.

FIG. 16B shows a superior view from cross section 16B-16B from FIG. 16A of one variation on producing modified pouch 302 having modified lumen 314 from main pouch 300 having main lumen 312 where junction 304 may be formed by rotating the stomach upon itself. FIG. 16C shows an alternative superior view from cross section 16B-16B from FIG. 16A where modified pouch 302' having modified lumen 314' may be formed from main pouch 300' having main lumen 312'. In this particular variation, junction 304' may be formed by taking apposed sides of the interior stomach lining near the lesser curvature and approximating them to form modified lumen 314'.

Several examples of different possible variations on the rotating probe or device are shown and described below. These variations are not intended to be limiting but are merely given as illustrative examples.

FIG. 17A shows vacuum tube 320 which may have an elongate tubular body. Tube 320 may be inserted into a patient's stomach transesophageally via, e.g., an endoscope. Accordingly, distal end 322 is preferably rounded or gently tapered to be atraumatic to the patient. An opening or window 324 may be defined in the wall of tube 320 near distal end 322 and as seen in FIG. 17B, opening 324 is preferably in communication with lumen 326, which may run throughout tube 320. The geometry of opening 324 is preferably large enough to accommodate the invagination of tissue from the interior stomach lining by a vacuum created within lumen 326 and opening 324. The vacuum may be activated by the physician from a proximal end of tube 320 from outside of the patient. Once tissue is invaginated within window 324, a fastening member may be inserted and deployed to secure the interior stomach lining thereby reducing its overall volume, as described in further detail below. As shown in FIG. 17B, which is cross section 17B-17B from FIG. 17A, tube 320 preferably has a diameter and cross section which may approximate a final geometry of the newly created lumen within the stomach.

FIG. 18A shows an isometric view of another variation in counter-rotating tube 330. Counter-rotating tube 330 may have a gently tapered distal end 332 with an opening 334 defined in the tube wall near distal end 332. Preferably contained within tube 330 is an additional inner tube 336, which may be geometrically similar to tube 330 but with a diameter small enough to allow free rotation about the longitudinal axis preferably shared by both tubes 330 and 336. Inner tube 336 likewise may have inner opening 338, which may allow communication between lumen 340 and openings 334 and 338. As above, a vacuum may be activated from a proximal end of tube 330 to draw tissue from the interior stomach lining through lumen 340 and into openings 334 and 338 when they are aligned. As shown in FIG. 18B, which is cross section 18B-18B from FIG. 18A, once the tissue has become invaginated within openings 334, 338, inner tube 336 may be rotated to effectively pinch and firmly hold the tissue in place, as shown in FIG. 18B. The addition of the pinching action in addition to the vacuum may aid in holding the tissue, thereby aiding in the rotation of both tube 330 and inner tube 336 when forming the modified lumen. Both tubes 330 and 336 may be manipulated and rotated from a proximal end of the tubes from outside of the patient.

FIG. 19A shows an isometric view of another variation in barbed tube 350. Tube 350 may be similar to vacuum tube 320 described above. Distal end 352 is preferably tapered and opening 354 may be defined in the wall of tube 350 near distal end 352. Additionally, at least one and preferably several attachment points 356, e.g., tines, barbs, or hooks, may be defined along at least a single edge around opening 354. Attachment points 356 are preferably defined along the leading edge of opening 354 for rotation of tube 350. FIG. 19B, which is cross section 19B-19B from FIG. 19A, shows opening 354 preferably in communication with lumen 358 and a preferred orientation of attachment point 356.

FIG. 20A shows an isometric view of yet another variation in split tube 360. Split tube 360 may be formed of at least two splittable halves, e.g., first half 364 and second half 366, which may be joined together longitudinally along split 370. When first half 364 and second half 366 are joined together, split tube 360 preferably forms a tapered distal end 362. Split tube 360 may also define a lumen 372 which may run throughout the length of split tube 360. This variation may also comprise at least one and preferably several attachment points 368 on each of first half 364 and second half 366. As shown in the figure, first half 364 may have a row of attachment points 368 preferably aligned along a portion of split 370 and second half 366 may likewise have a row of attachment points 368 juxtaposed and preferably mirroring those located on first half 364. Attachment points 368 may be of any type described above and the number and positioning of attachment points 368 may depend upon the desired length of the resulting junction formed upon rolling the stomach. FIG. 20B, which is cross section 20B-20B from FIG. 20A, shows split 370 and an example of the juxtaposed relationship of attachment points 368.

Figure 21:
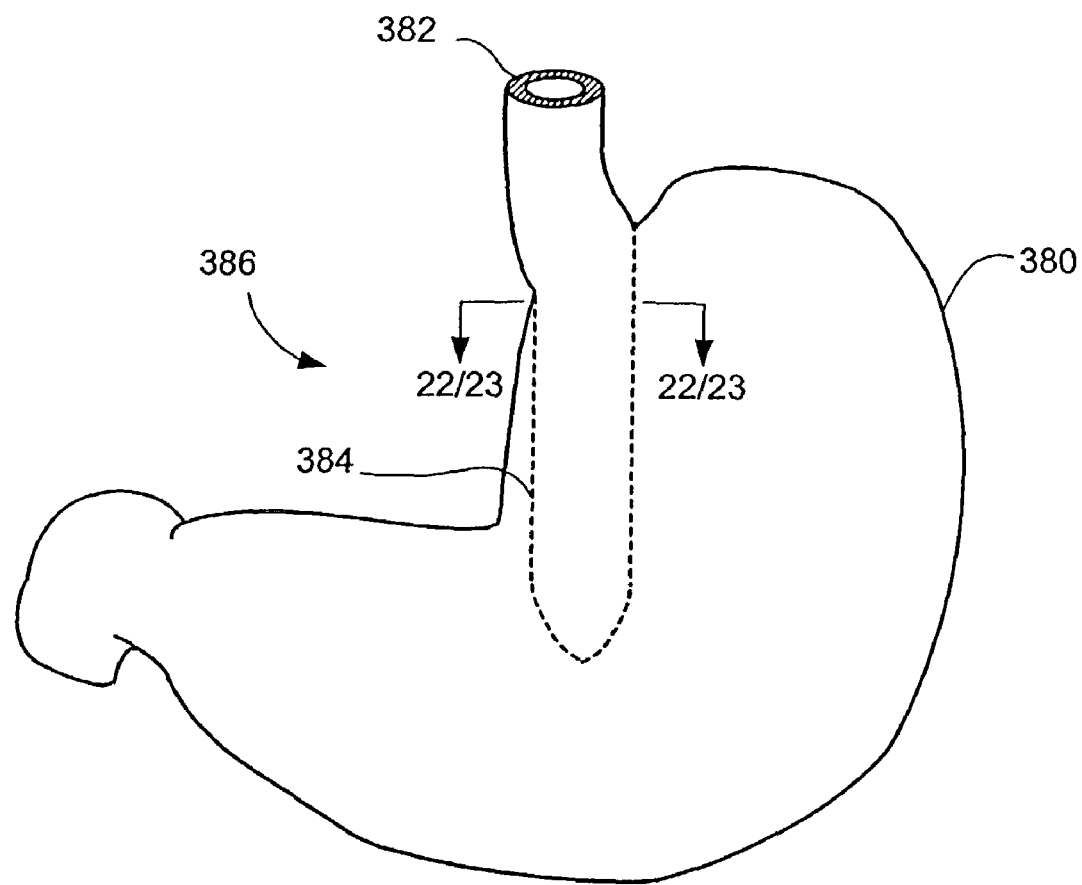
FIG. 21 shows an example of placement within a stomach of a rotatable device variation.

FIG. 21 shows an example of a rotatable probe device during insertion into stomach 380. As seen, tube 384 may be inserted into stomach 380 via esophagus 382, preferably endoscopically. Tube 384 may be any of the devices described above and is shown generally as an example of how such devices may be inserted into an organ, e.g., stomach 380. As tube 384 is inserted, it may engage a portion of the interior of stomach 380, preferably along lesser curvature 386. The engagement may be accomplished by any of the methods described herein, e.g., attachment points partially piercing the stomach lining, a vacuum adhering a portion of the lining, etc. Once engaged, tube 384 may then be rotated to roll the engaged portion of the stomach wall around the probe itself to bring the wall in apposition with another portion of the stomach wall.

Figure 22A:
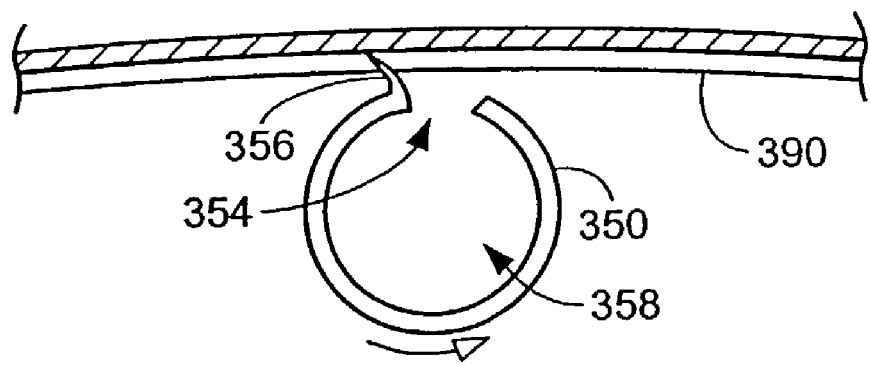
FIGS. 22A and 22B show the possible creation of a rotated lumen using the device of FIGS. 19A and 19B.
Figure 22B:
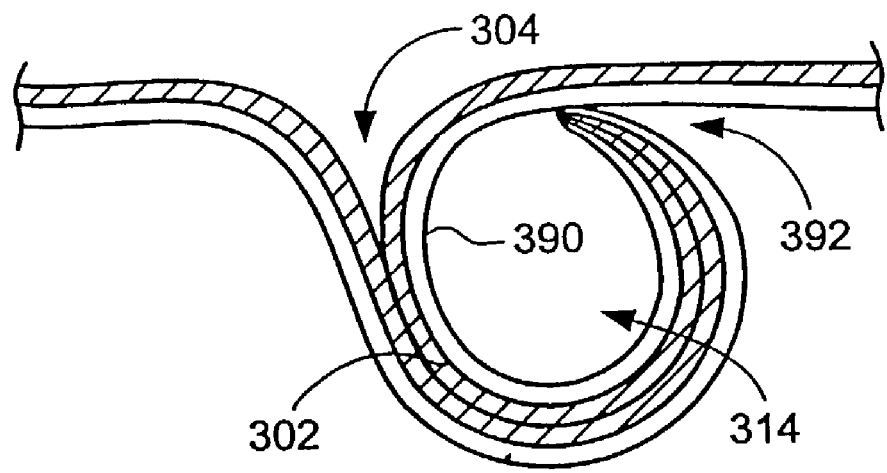

FIG. 22A shows a variation on partial cross section 22/23-22/23 from FIG. 21 with tube 350 from FIGS. 19A and 19B in a preferred operation. As shown, interior lining 390 may be adhered to tube 350 via a vacuum created in opening 354 through lumen 358 and/or via attachment points 356 which may partially pierce lining 390, as described above. The location for adhering tube 350 may also be determined or aided by the use of marking device 40, as described above. Once the desired location of interior lining 390 has been established, tube 350 may be rotated about its longitudinal axis, following the arrow as shown, by at least about 180° and preferably at least about 360°. Lining 390 is preferably rotated until the adhered portion contacts a second portion of lining 390 to result in the modified lumen 314 of FIG. 22B, also shown in FIG. 16B. Once modified lumen 314 has been formed, fasteners may be fired or deployed through opening 354 or via a separate endoscopic stapling device at location 392 to secure and maintain modified lumen 314. Fasteners may comprise any of the fasteners as described herein, e.g., staples. Once modified lumen 314 has been secured, tube 350 may then be removed. FIG. 16B shows newly created modified pouch 302 with modified lumen 314 and, as seen, interior lining 390 also forms the interior surface defining modified lumen 314.

FIGS. 23A to 23D show another variation on partial cross section 22/23-22/23 from FIG. 21 with split tube 360 from FIGS. 20A and 20B. Split tube 360 may be inserted into the stomach either as separate halves 364, 366 individually or as a whole tube which may then be split while in the stomach. Once separated, first half 364 and second half 366 may be engaged to interior lining 390 by attachment points 368 at a slight distance from one another. The separation distance may be determined by the desired resulting size of the lumen. Alternatively, the separation distance may be determined or aided by the use of marking device 40, as described above.

Figure 23A:
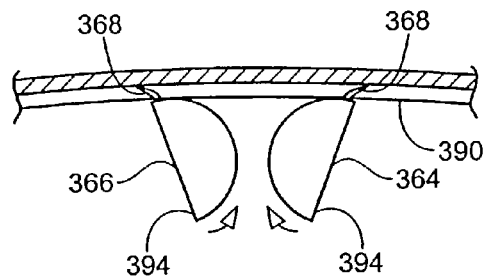
FIGS. 23A to 23D show the possible creation of a rotated lumen using the device of FIGS. 20A and 20B.
Figure 23B:
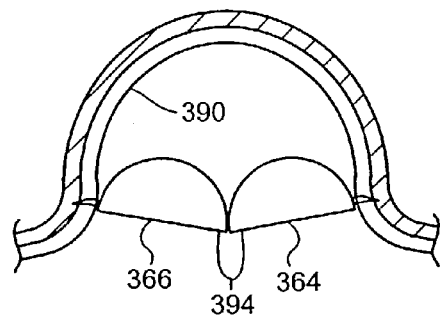
Figure 23C:
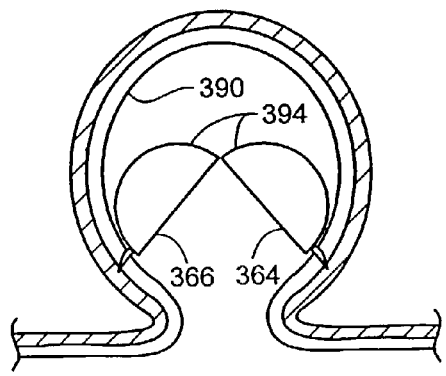
Figure 23D:
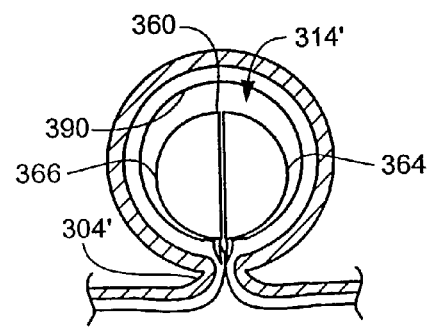

Once first half 364 and second half 366 have engaged interior lining 390, as shown in FIG. 23A, each of free ends 394 of halves 364, 366 may then be rotated in the direction of the arrow, as shown. Free ends 394 may be configured to simply contact each other or to interlock with each other and rotate about a hinge or pivot. As first half 364 and second half 366 continue to be rotated, FIGS. 23B and 23C show the progression of lumen formation as attachment points 368 draw around and towards one another. Finally in FIG. 23D, as split tube 360 is preferably formed again, modified lumen 314' may be formed, as also shown in FIG. 16C, to then be secured or maintained preferably by fasteners, e.g., staples, which may be deployed through junction 304'.

Figure 24A:
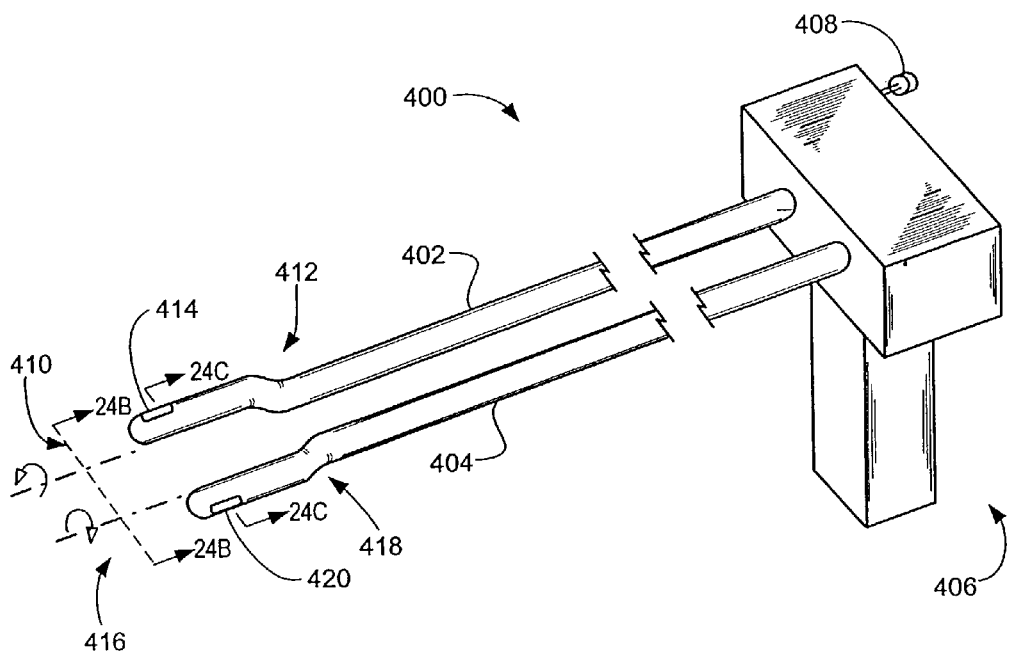
FIG. 24A shows an isometric view of a variation on a dual rotatable tube device.

A further variation on a rotating device is shown in the isometric view of dual tube device 400 shown in FIG. 24A. Dual tube device 400 may have at least two elongate members, first member 402 and second member 404, which may be rotatingly attached to controlling device 406 and may be parallel to each other. The members 402, 404 are preferably counter-rotating and may be rotated by a rotation control 408, which is preferably located on controlling device 406. First member 402 may have first distal end 410 offset slightly from the longitudinal axis of first member 402 by first bend 412. First opening 414 is also preferably defined in the wall of first member 402 proximally of first distal end 410. Second member 404 is preferably similar to first member 402 and may have second distal end 416 offset slightly from the longitudinal axis of second member 404 by second bend 418. Near second distal end 416, second opening 420 may be defined in the wall of second member 404.

Figure 24B:
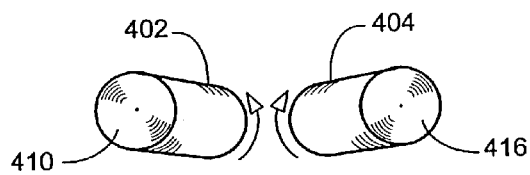
FIGS. 24B and 24C show an end view and cross section view, respectively, of the device of FIG. 24A.
Figure 24C:
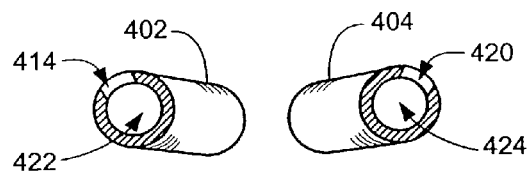

FIG. 24B shows end view 24B-24B from FIG. 24A. Distal ends 410, 416 are seen as preferably being parallel and mirror images of one another. Also, the preferable counter-rotating action may be seen by the directional arrows. FIG. 24C shows cross section 24C-24C from FIG. 24A. As shown, the relationship between first and second opening 414, 420, respectively, and first and second lumen 422, 424, respectively, may be seen in the figure. Lumens 422, 424 preferably run through the length of members 402, 404, respectively, and are in communication with openings 414, 420. A vacuum may be created in openings 414, 420 through lumens 422, 424, respectively, from the controlling device 406. In operation, members 402, 404 may be inserted trans-esophageally into a patient's stomach. A vacuum may then be created in first and second openings 414, 420 to engage a portion of the stomach interior lining. Once engaged, a modified pouch may be created from the interior lining in much the same manner as described for FIGS. 23A to 23D, except the individual counter-rotating members 402, 404 do not form a split tube. The operation of the vacuum application and counter-rotation may be controlled through controlling device 406 which is preferably located outside the patient's body.

Figure 25A:
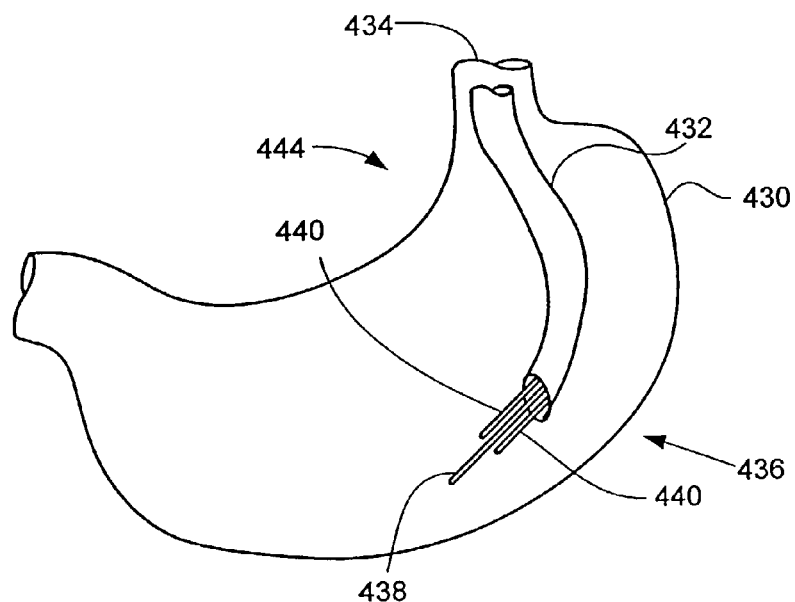
FIG. 25A shows a variation on an endoscopic vacuum device in a stomach.
Figure 25B:
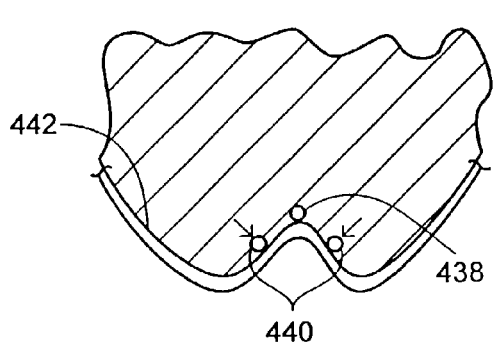
FIGS. 25B and 25C show an end view of a variation on lumen creation from the interior surface of the stomach using the device of FIG. 25A.
Figure 25C:
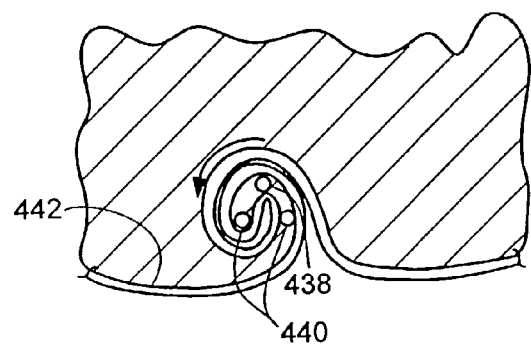

FIG. 25A shows yet another variation in vacuum device 432 shown inserted into stomach 430. Vacuum device 432 may be an endoscopic device inserted trans-esophageally into stomach 430 through esophagus 434. Device 432 may have vacuum member 438 and at least two grasping members 440, preferably disposed on either side of vacuum member 438. Once device 432 has been introduced into stomach 430, vacuum member 438 may be steered towards a desired area of interior lining 442, as seen in FIG. 25B which is a cross section view of device 432 attached to stomach interior lining 442. The desirable area of interior lining 442 may be located along greater curvature 436 or alternatively along lesser curvature 444, depending upon the desired results. In position, a vacuum may be activated in member 438 to draw a portion of interior lining 442 preferably between grasping members 440. As lining 442 is adhered to vacuum member 438, grasping members 440 may be used to pinch and grasp the drawn portion of lining 442. Then, device 432 may be rotated in the direction of the arrow indicated in FIG. 25C to result in the formation of a modified lumen. Afterwards, grasping members 440 may be locked in place, disengaged from device 432, and left as an implant. Alternatively, lining 442 may be fastened to maintain the created lumen by any of the methods described herein and grasping members 440, along with the rest of device 432, may be removed from stomach 430.

Gastric Reduction Tools and Methods Using Volume Reduction Devices

Aside from the use of rotating and rotatable probes, gastric volume reduction devices may also be used as part of the present invention. Such volume reduction devices generally may be inserted into a stomach trans-esophageally through the use of, e.g., an endoscope. The reduction device may be used to draw or engage a portion of the interior lining of the stomach; the drawn or engaged portion may then be eventually removed, either actively or through natural processes.

Several examples of different possible variations on the gastric volume reduction devices are shown and described below. These variations are not intended to be limiting but are merely given as illustrative examples.

Figure 26:
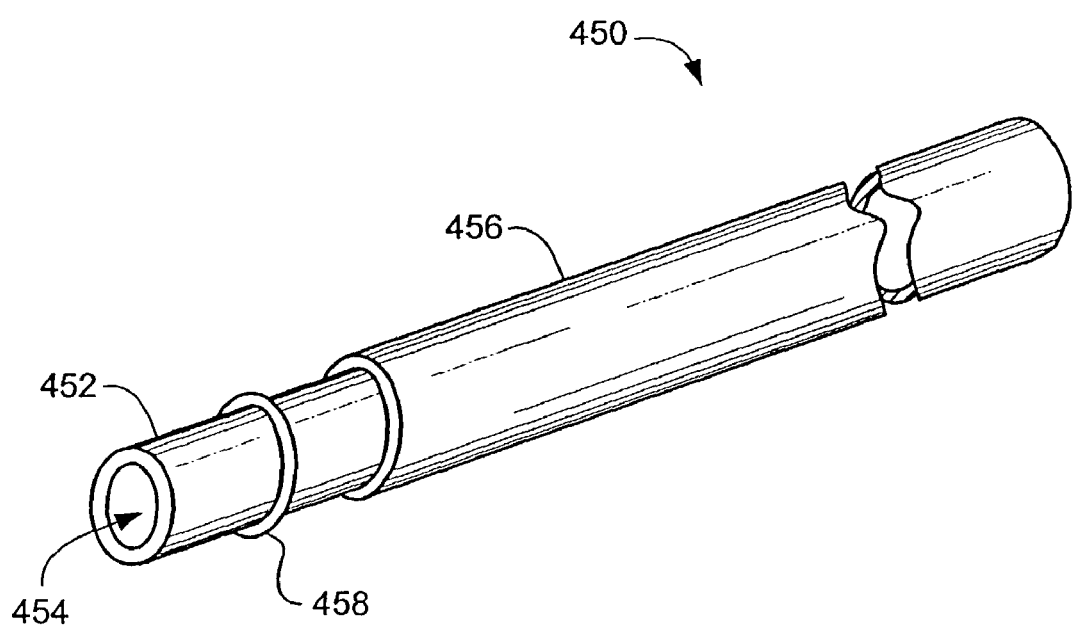
FIG. 26 shows an isometric view of a variation on a gastric volume reduction device.

FIG. 26 shows an isometric view of a variation on the gastric volume reduction device in concentric tube device 450. Device 450 may have inner tube 452 defining lumen 454, which preferably runs throughout inner tube 452. Pusher sleeve 456 may be disposed concentrically over inner tube 452 such that pusher sleeve 456 may be allowed to slide freely along inner tube 452. Pusher sleeve 456 is also preferably disposed over inner tube 452 such that the distal end of inner tube 452 is open to allow ring 458 to be rolled or stretched onto the distal end. Ring 458 is preferably made of an elastic type material which would allow ring 458 to elastically cinch onto inner tube 452.

Figure 27A:
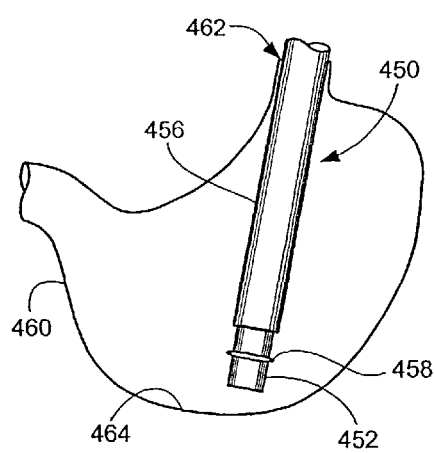
FIGS. 27A to 27D show the device of FIG. 26 inserted into a stomach to draw or cinch up lining tissue to reduce a volume of the stomach.

During use, FIG. 27A shows a view of concentric tube device 450 within stomach 460 preferably inserted through esophagus 462. The distal end of device 450, particularly inner tube 452, may be brought into position near a location of interior surface 464 where tissue may be desirably removed.

Figure 27B:
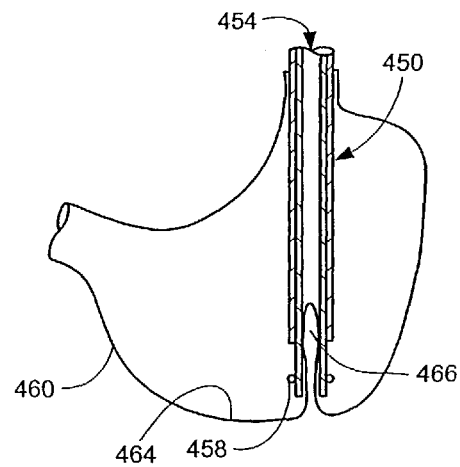
Figure 27C:
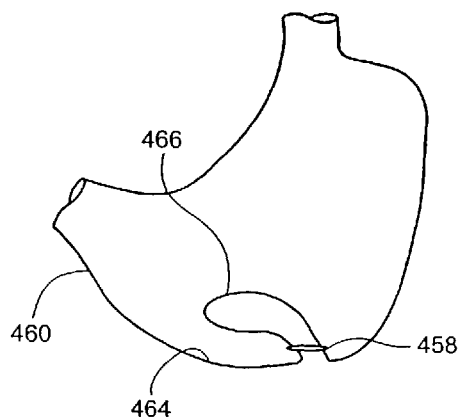
Figure 27D:
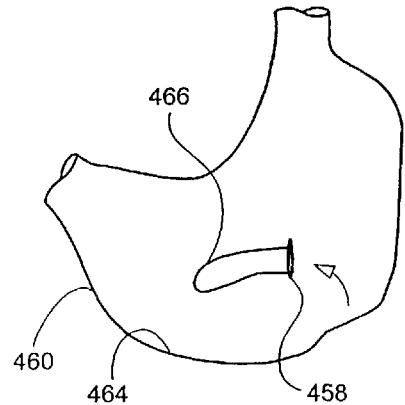

As shown in FIG. 27B, once device 450 is in place, a vacuum may be actuated within lumen 454. The vacuum may then draw a portion of withdrawn lining tissue 466 up into lumen 454, as seen in the cross section of device 450. While lining tissue 466 is held within lumen 454, pusher sleeve 456 may be pushed or urged distally along inner tube 452. As pusher sleeve 456 advances, it may also push or urge elastic ring 458 distally along inner tube 452 until ring 458 is pushed entirely off the distal end of inner tube 452 and onto a portion of lining tissue 466, as seen in FIG. 27C. Device 450 may then be removed from stomach 460 after ceasing the vacuum, thereby leaving lining tissue 466 with elastic ring 458. After time, as seen in FIG. 27D, pressure necrosis may cause lining tissue 466 and ring 458 to simply fall off from the rest of interior surface 464 to be passed normally through the rest of the patient's body. The action of drawing up and removing a portion of interior surface 464 may effectively reduce the overall volume of stomach 460, thereby reducing the available volume for the ingestion of foods. As such, this procedure may be repeated several times either sequentially or simultaneously until the overall volume of stomach 460 is reduced to a desirable volume depending upon the desired results.

Figure 28:
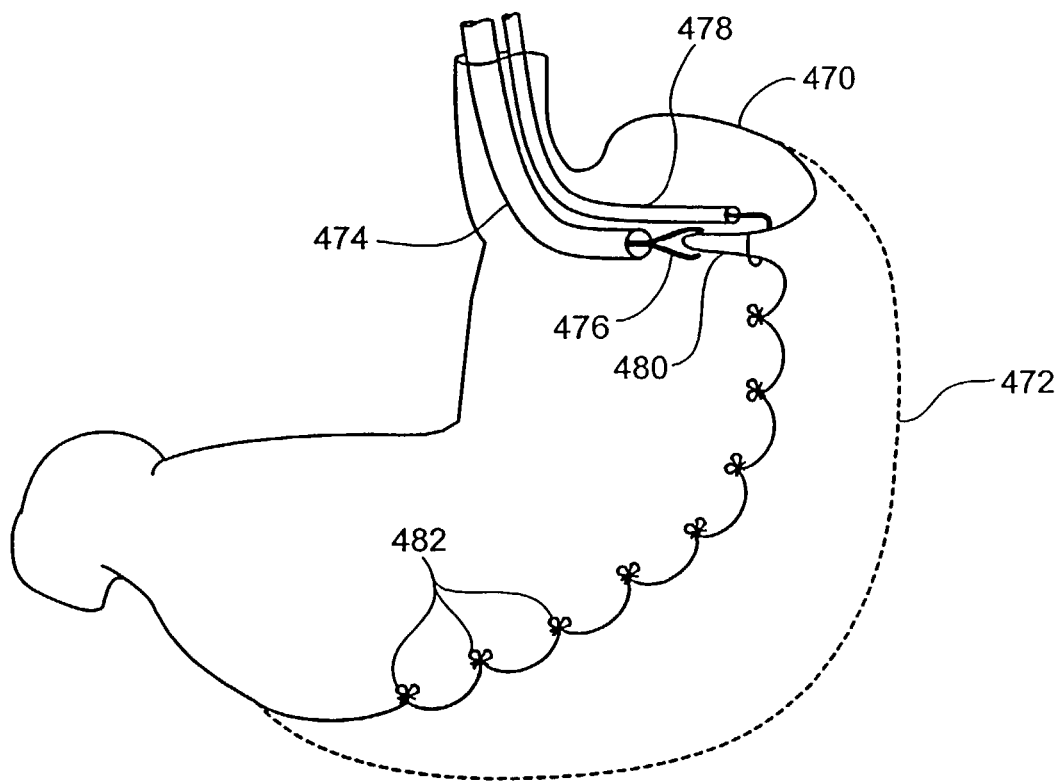
FIG. 28 shows another variation on a gastric volume reduction device utilizing a grasping device and a ligating device.

FIG. 28 shows another variation on the gastric volume reduction device. As shown, an endoscope 474 preferably having grasping device 476, e.g., biopsy forceps, may be inserted into stomach 472. A ligating apparatus, e.g., ring stapler, zip tie, etc., either as part of endoscope 474 or as a separately introduced ligation device 478, is preferably also introduced within stomach 472. Forceps 476 and ligation device 478 may be used in conjunction with one another by, e.g., having forceps 476 grasp withdrawn tissue 480 and then having ligation device 478 tie or ligate tissue 480. Forceps 476 may then be used to excise and remove withdrawn tissue 480 above ties 482 to reduce the overall stomach volume. An example of a jaw structure which may be utilized is shown and described in U.S. Pat. No. 5,749,893 to Vidal et al., which is incorporated herein by reference in its entirety. Alternatively, ligated withdrawn tissue 480 may be left attached to stomach 470 to be removed naturally by pressure necrosis. Several excisions may be performed in reducing stomach volume from, e.g., stomach 472 (as shown by the dashed lines) down to a final reduced stomach 470.

FIG. 29A shows yet another variation with tractive rollers 490. This device may have at least two rigid rollers 492, which are preferably elongated, connected to one another preferably at both ends by, e.g., elastic members 494. The connection of rollers 492 may create channel 496 therebetween through which tissue may be drawn. FIG. 29B shows rollers 492 with a portion of stomach interior surface 498 being drawn through channel 496 by a grasping device, e.g., forceps 500. Meanwhile, rollers 492 may be maintained within the stomach by, e.g., retaining forceps 502, which may be used to hold rollers 492 relative to interior surface 498. Elastic members 494 may pinch rollers 492 together, thereby creating a zone of pressure necrosis in withdrawn interior surface 498. Also, as interior surface 498 is drawn up through channel 496, rollers 492 may contain a ratcheting device within to prevent surface 498 from rolling out back through channel 496. Once the desired amount of surface 498 has been drawn, it may either be excised or simply left to be removed naturally by necrosis. FIG. 29C shows an alternative variation with ratcheted rollers 504. Ratcheted rollers 504 may be operated in the same manner as described for rollers 492 but they preferably have a tractive surface to enhance traction between the tissue and the rollers 504. Torquing device 506 may be used with ratcheted rollers 504 and may be introduced into the stomach endoscopically to mesh with one of rollers 504 for the purpose of causing it to rotate. Moreover, either rollers 492 or ratcheted rollers 504 may be used simply to gather stomach surface tissue to allow for fastening, e.g., suturing, stapling, etc.

Pyloroplasty Tools and Methods

Creating a smaller gastric pouch within the stomach may be accomplished by a variety of methods, as described above. To aid in the overall effect for the treatment of obesity, a pyloroplasty procedure may also be performed to enhance treatment. The pyloroplasty may be performed prior to (preferable), in conjunction with, or following the gastric reduction procedure. A pyloroplasty procedure typically results in the pyloric sphincter being rendered incompetent. However, in the case of treatments for GERD using the devices and methods described above, the pyloroplasty procedure as described herein may be omitted. Conventional pyloroplasty procedures may typically be performed surgically or through the use of standard peripheral angioplasty balloons, e.g., in the 7 mm range. However, in order to render a relatively healthy and normal pylorus permanently incompetent, a more aggressive procedure may be needed.

To accomplish this generally, a pyloroplasty device may be passed endoscopically through the esophagus, into the stomach, and preferably into position in or across the pylorus. Energy or a stimulus is then preferably applied to the pylorus to render it incompetent. Energy may be in the form of, e.g., heat, electrical, chemical, RF, etc., or a combination. Examples of chemical energy stimulus may comprise alcohol and sotrodecol. The stimulus may be in the form of, e.g., dilatation, cutting, ablation, viral, etc., or a combination. An example of a viral or chemical stimulus may be, e.g., a poison such as the botulinum toxin type A virus (Botox). An example of a method of use for Botox is described in U.S. Pat. No. 5,437,291 to Pasricha et al., which is incorporated herein by reference in its entirety. An incompetent pylorus may allow stomach contents to drain directly into the proximal duodenum with minimal resistance. Moreover, some of the mentioned pyloroplasty treatments may be selected or designed to last only for a specific time period, e.g., a week or several months, etc. For instance, the effects of simple dilatation or the injection of Botox may be designed to render the pylorus incompetent for only a few months, which may be a desirable time period for the patient to obtain the desired results of the procedure.

Several examples of different possible variations on pyloroplasty devices are shown and described below. These variations are not intended to be limiting but are merely given a's illustrative examples.

Figure 30:
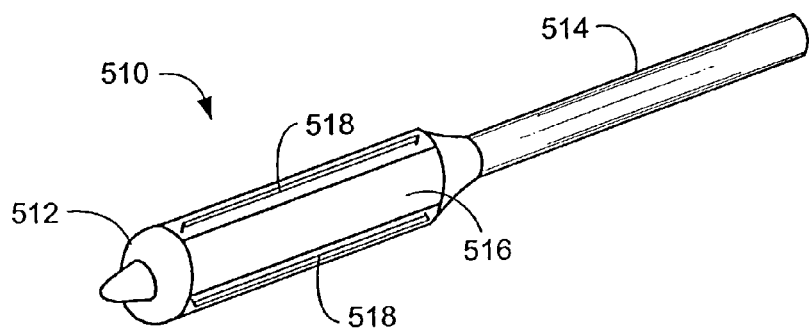
FIG. 30 shows an isometric view of a variation on a pyloroplasty device with an angioplasty balloon.

FIG. 30 shows an isometric view of one variation of a dilatation device in balloon device 510 which may have angioplasty balloon 512 located near or at the distal end of catheter 514. Angioplasty balloon 512 may be used alone to simply dilate the pylorus. Alternatively, exterior balloon surface 516 may have at least one and preferably several stimulating members 518 disposed about surface 516. Stimulating members 518 are shown in the figure as cutting blades or wires, but alternatively, they may include electrodes, cryogenic dispensing probes or members, chemical dispensing probes, etc. Moreover, balloon 512 may alternatively be a dilation wire basket similarly disposed with stimulating members 518.

Figure 31:
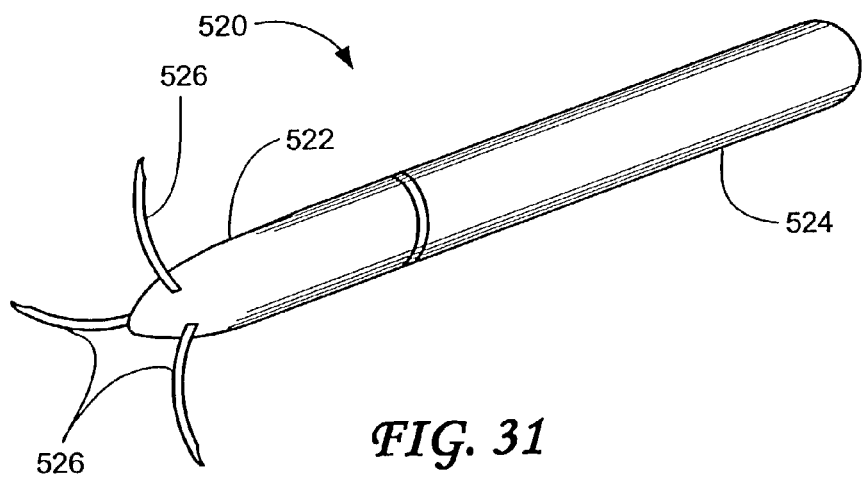
FIG. 31 shows an isometric view of another variation on a pyloroplasty device with extendable probes.

FIG. 31 shows an isometric view of another variation in probe device 520. Device 520 may have catheter or delivery member 524 with, e.g., probes 526, which may extend from distal end 522. Although three probes 526 are shown in the figure, at least one and up to several probes of varying thickness and lengths may be used. Probes 526 may be retractable so that during delivery through, e.g., the esophagus or stomach, probes 526 may be withdrawn within distal end 522 and then extended when treating the pylorus. Probes 526 may be electrically connected to a voltage or power source located outside the patient's body to deliver electrical, RF, or heat energy to the pylorus. Alternatively, they may be configured like a needle to deliver chemical or biological stimuli to render the pylorus incompetent. For example, probes 526 may be used to inject chemicals, e.g., alcohol, sotrodecol, or other ablative chemicals, or biological stimuli, e.g., Botox virus or some other incapacitating virus, into the pylorus. Such stimulants may be carried within distal end 522, delivery catheter 524, or they may also be delivered from the proximal end of catheter 524 and injected through to probes 526.

Figure 32A:
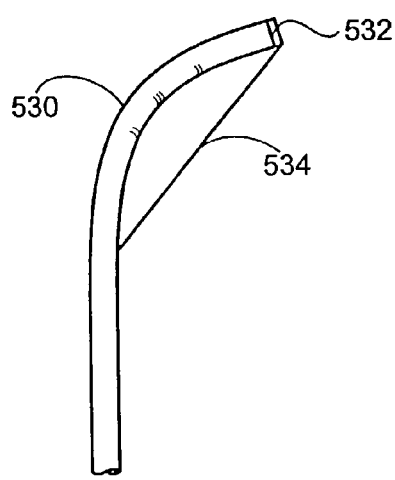
FIGS. 32A and 32B show variations on sphincterotome arms for use in a pyloroplasty procedure.
Figure 32B:
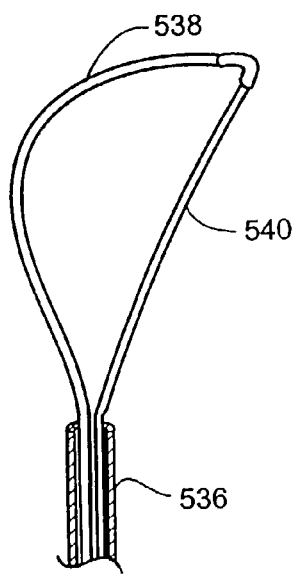

Other variations which may be used for the pyloroplasty procedure are shown in FIGS. 32A and 32B. FIG. 32A shows sphincterotome arm 530 having a distal end 532. Arm 530 may be bent as shown to allow cutting member 534 to be drawn between distal end 532 and a location proximal of distal end 532 along arm 530. Another variation is seen in FIG. 32B where delivery member 536 may have an arcuate support member 538 to support cutting member 540. The variations shown in FIGS. 32A and 32B may be delivered via a catheter or endoscope trans-esophageally and through the stomach to the pylorus where either cutting member 534, 540 may be used to cut or saw into the tissue in or around the pylorus to render it incompetent. These particular variations of sphincterotomes shown in FIGS. 32A and 32B may be manufactured by Medi-Globe Corporation, located in Tempe, Ariz.

Figure 33:
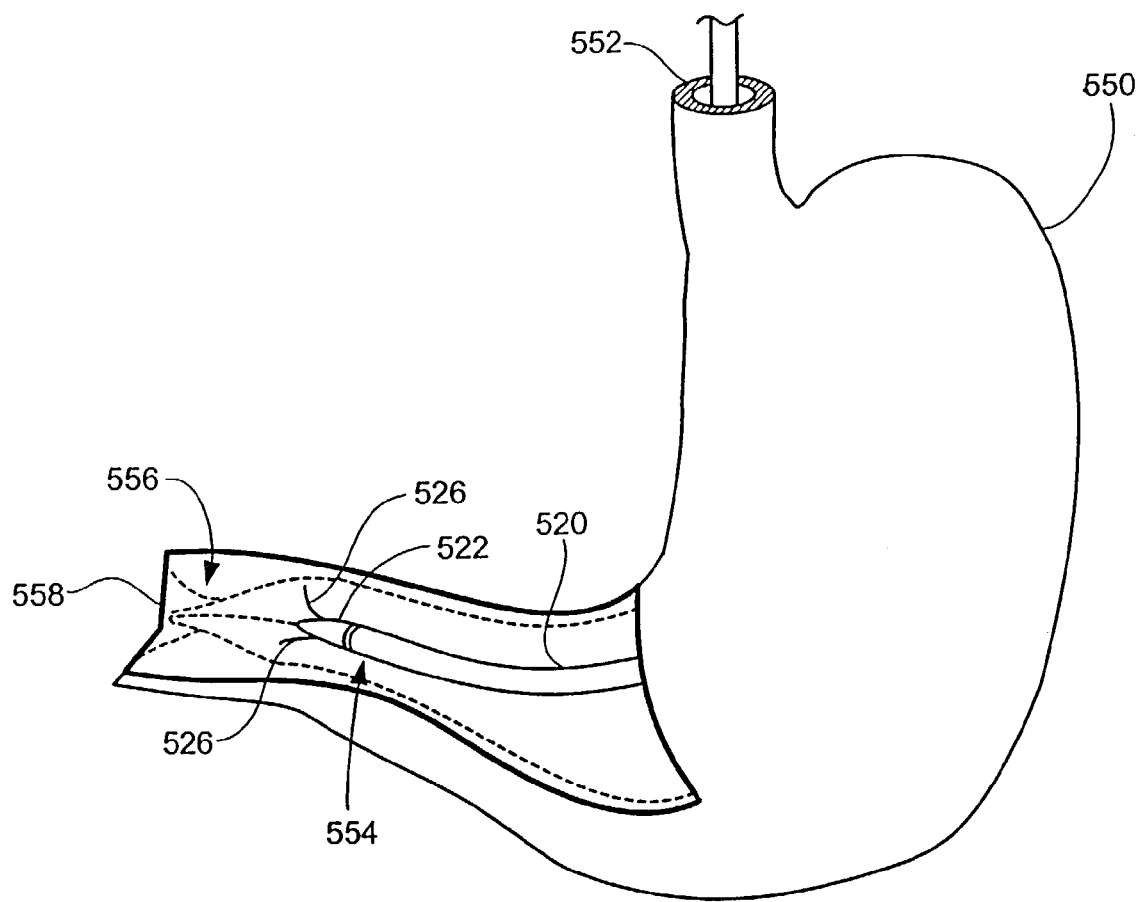
FIG. 33 shows a stomach with a distal portion of the wall of the lesser curvature removed to show a possible use for the device of FIG. 31.

FIG. 33 shows stomach 550 with a distal portion of the wall of the lesser curvature removed for clarity. Device 520 may be delivered through esophagus 552 to a location proximal of pylorus 558, e.g., first position 554. If probes 526 were retracted during delivery, they may then be extended, as shown. Distal end 522 of device 520 may be advanced to, e.g., second position 556, such that probes 526 may pierce pylorus 558 to deliver the stimulus.

Figure 34A:
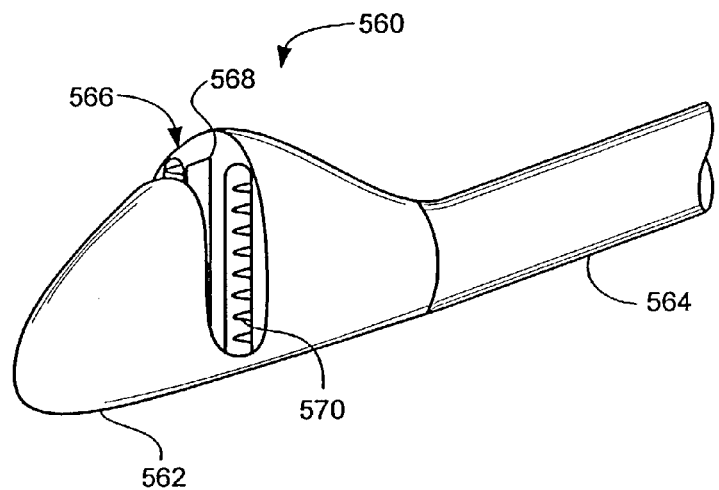
FIG. 34A shows an isometric view of another variation on a pyloroplasty device with a combination cutting and stapling notch.
Figure 34B:
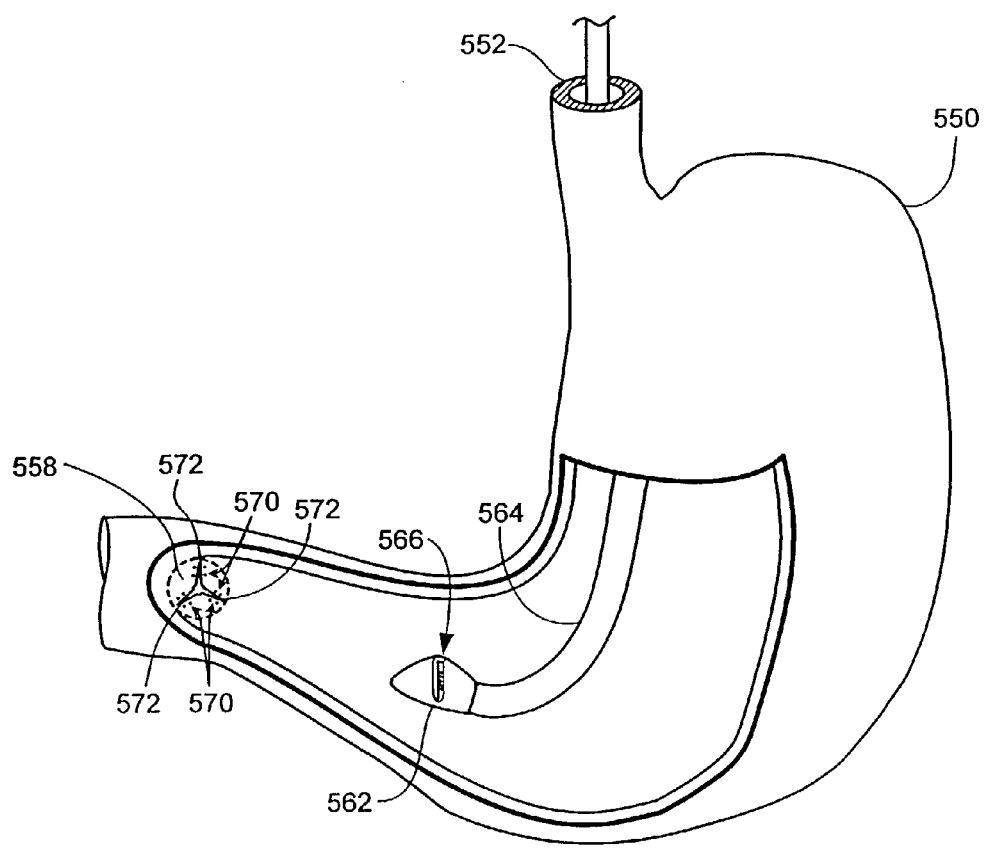
FIG. 34B shows the device of FIG. 34A in a possible use in a stomach.

FIG. 34A shows an isometric view of another variation with combination device 560. Device 560 may have housing 562 on the distal end of delivery catheter or endoscope 564. Housing 562 defines notch 566 which may be oriented perpendicularly relative to the longitudinal axis defined by endoscope 564. Notch 566 preferably has a geometry large enough to accommodate part of pylorus 558 and housing 562 may be tapered at its distal end to allow for easy insertion into the pylorus 558 during the procedure. Within notch 566 may be cutting blade 568 and on either side of blade 568 may be fasteners 570, e.g., individual anchors, staples, etc. In operation, FIG. 34B shows housing 562 and endoscope 564 delivered through esophagus 552. The wall of stomach 550 is partially cut away for clarity. Housing 562 may be inserted into pylorus 558, then notch 566 is preferably aligned such that part of the pyloral sphincter lies within notch 566. Alternatively, the pyloral tissue may also be drawn into notch 566 via a vacuum or grasping member. Once the pyloral tissue is within notch 566, cutting blade 568 may be actuated to traverse notch 566 and sever part of the tissue of pylorus 558. Fasteners 570 may then be deployed on either side of incision 572 to affix the incised tissue. The number of incisions 572 may vary depending upon the desired degree of pyloric disablement. Alternatively, an inflatable balloon may be attached on the back of notch 566 and inflated to push housing 562 into apposition with pylorus 558 and cause invagination of the tissue into notch 566.

Anastomosis Tools and Methods

In addition to the tools and methods described above for gastric reduction and pyloroplasty procedures, an additional anastomosis gastric bypass procedure may also be performed to further enhance treatment. The anastomosis procedure may be performed preferably prior to, in conjunction with, or following the gastric reduction and pyloroplasty (if performed at all) procedures. In the case of treatments for GERD using the devices and methods described above, the anastomosis procedure as described herein may be omitted. The procedure generally involves endoscopically or laparoscopically creating a side-to-side anastomosis preferably from within the stomach and bowel and within the digestive tract. This procedure may be similar to the Roux-en-Y gastric bypass (RYGB) procedure but with minimal trauma. This procedure may also effectively bypass food from the stomach, past a proximal portion of the bowel, and preferably directly into a lower portion of the bowel. This bypassed portion may be considered a malabsorption zone.

Figure 35:
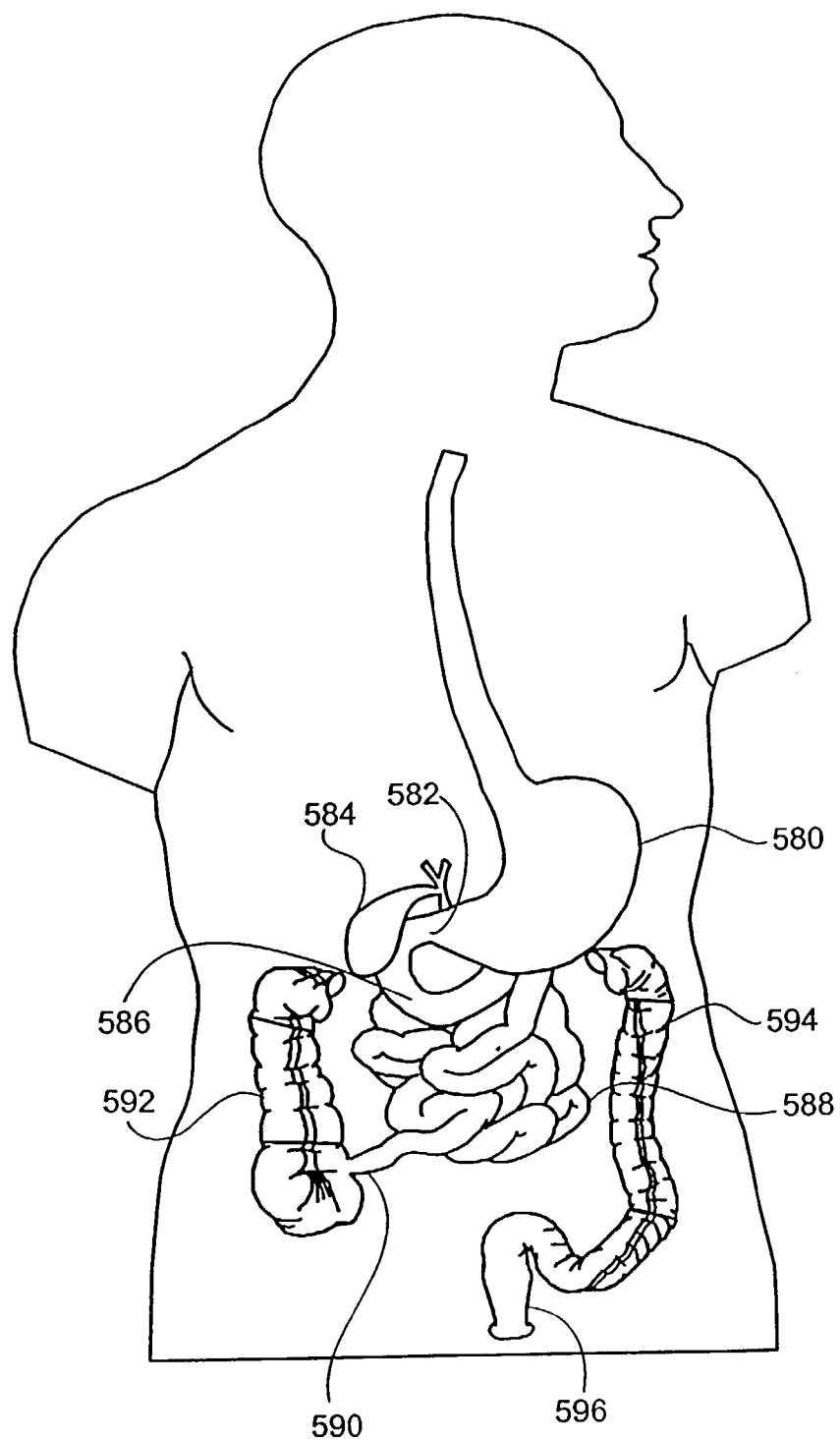
FIG. 35 shows a representative and normal gastro-intestinal system of a person.

A representative and normal gastro-intestinal system of a person is shown in FIG. 35 for comparison. Stomach 580 is shown with pyloric sphincter 582 near gallbladder 584 and attached to the proximal section of duodenum 586. The distal section of duodenum 586 is attached to the proximal section of jejunum 588, the distal section of which is further attached to the proximal section of ileum 590. Ileum 590 is then attached to ascending colon 592, which continues through to the transverse colon (which has been removed for clarity), and then to descending colon 594 and finally to rectum 596.

Figure 36:
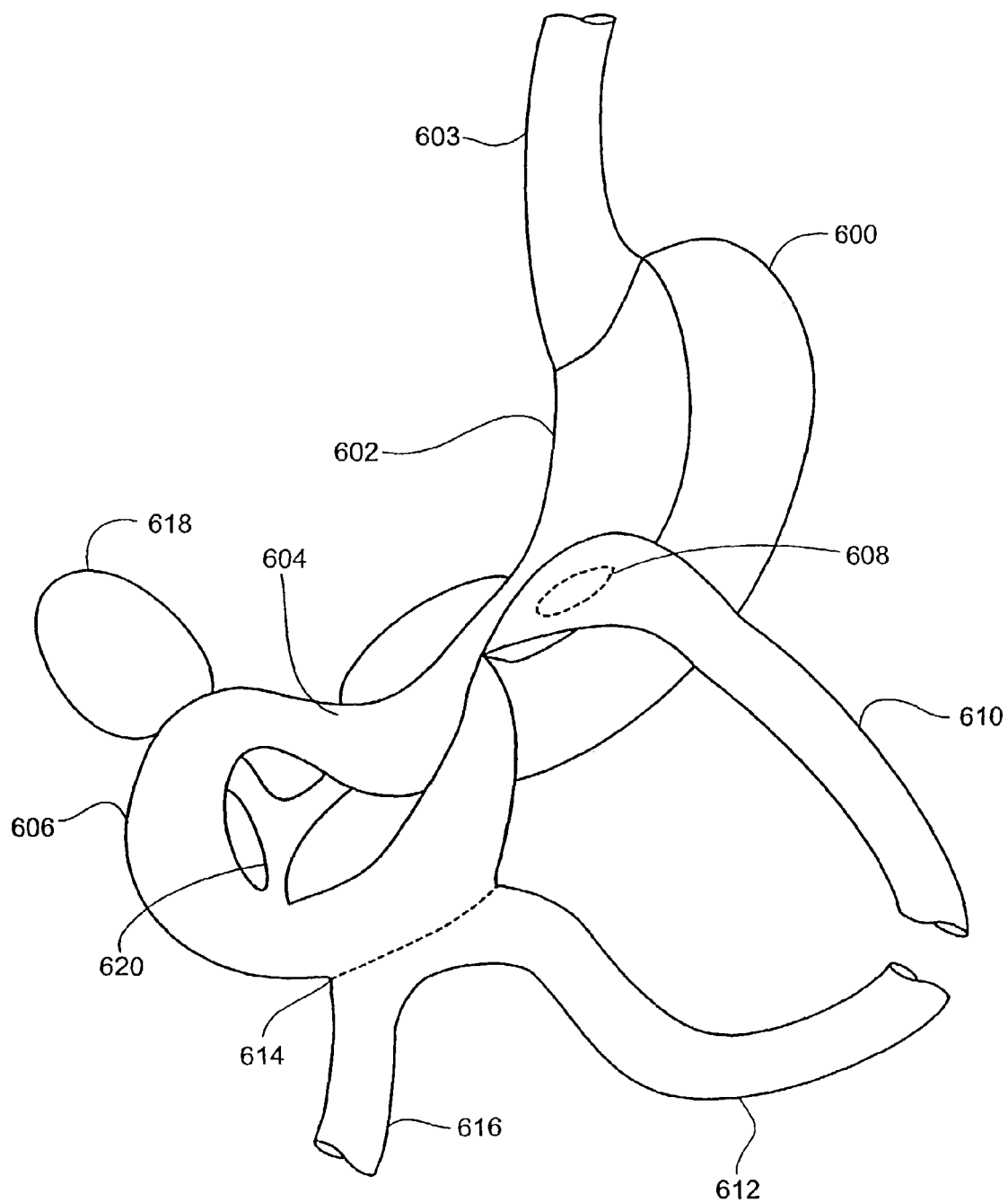
FIG. 36 shows an example of a gastro-intestinal system modified by a preferable anastomosis procedure.

A gastro-intestinal system which may be modified by a preferable anastomosis procedure is shown in FIG. 36. Stomach 600 is shown in this variation as having been modified by creating modified pouch 602, which may be created by any of the methods and tools as described above. Esophagus 603 is preferably connected to a proximal end of pouch 602. As described above, the distal end of pouch 602 may be connected directly to pylorus 604 or alternatively, may be a blind-ended pouch and pylorus 604 is connected to the proximal end of duodenum 606. A first anastomosis 608 may be created preferably between modified pouch 602 and a section of digestive tract either from the distal duodenum 606 or proximal jejunum 610. First anastomosis 608 may be located in a range from about 20 to 50 cm from pylorus 604. A second anastomosis 614 may be created preferably between a section of duodenum 606 and a section of ileum 612. The second anastomosis 614 may be located in a range from about 15 to 55 cm from pylorus 604 or about 150 to 200 cm down along the length of the small intestines from pylorus 604. This procedure may allow for drainage of secretions created by stomach 600 to pass through pylorus 604 and secretions of bile and chyme from the pancreas and gallbladder 618 to pass through biliary duct 620 partly through duodenum 606 and then through second anastomosis 614 and directly into distal ileum 616 and out of the body. The bypassed stomach 600, pylorus 604, and proximal duodenum 606 may act as a malabsorption zone because sugars and fats which might normally be mostly absorbed in this zone may now be directly passed into the distal duodenum 606 or proximal jejunum 610.

During the anastomosis procedure, both first and second anastomoses 608, 614, respectively, may be created first. Duodenum 606 may then be closed off between the two anastomoses 608, 614. Then, depending upon the length and size of the resulting modified stomach 602, pylorus 604 may be closed off or left open, depending upon the desired result and which of procedures and tools are implemented. Finally, modified pouch 602 may be created after the anastomoses procedures. Alternatively, modified pouch 602 may be created prior to the anastomoses procedures, again depending upon the desired result and which of procedures and tools are implemented. If modified pouch 602 were created first, then the anastomoses procedure may be reversed to essentially end with the same result.

Figure 37:
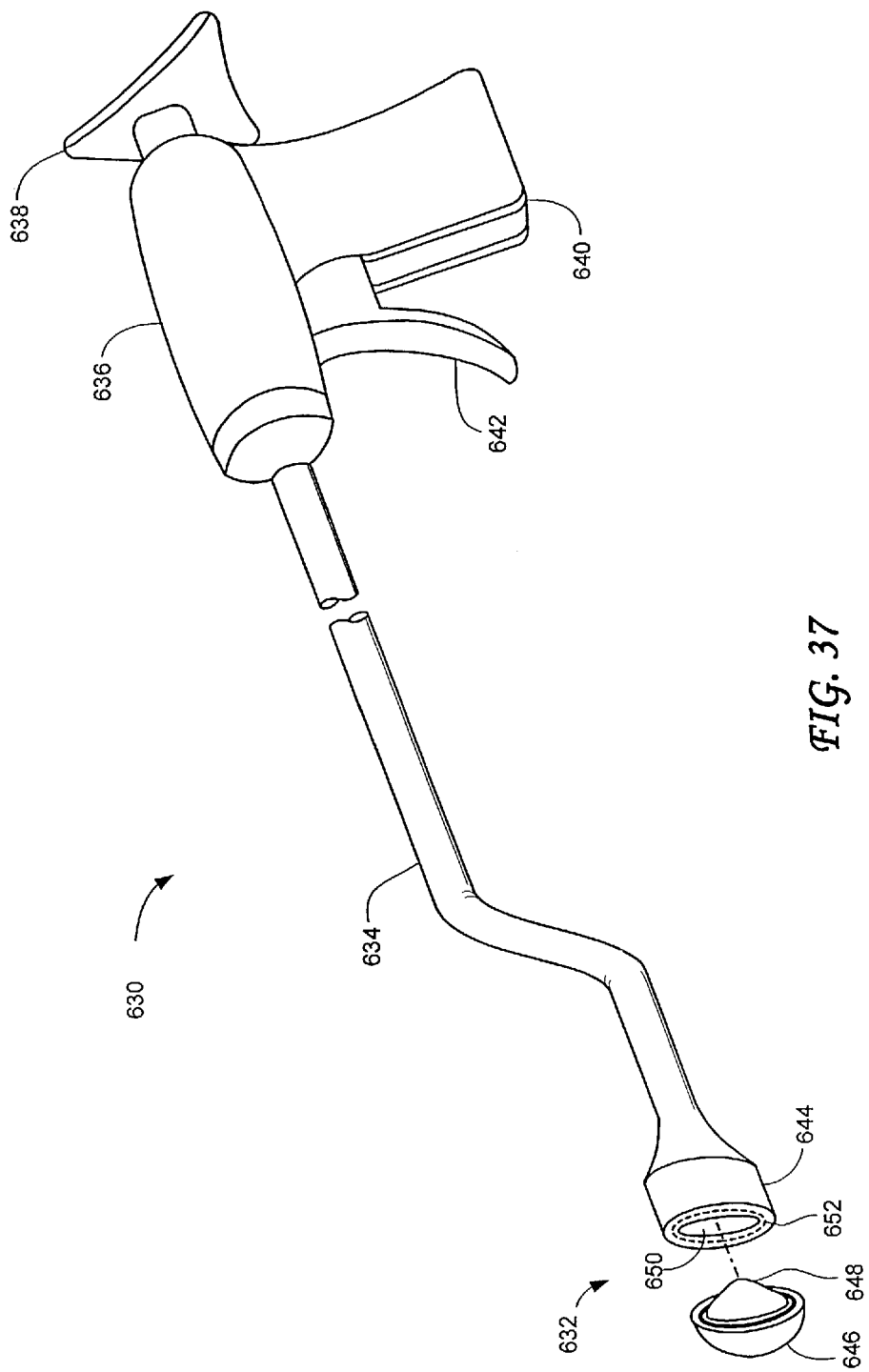
FIG. 37 shows an isometric view of a variation on an anastomosis deployment device.

A conventional RYGB procedure is generally performed through a 6-8 inch incision extending from the end of the breastbone to just above the navel. However, the procedure described above may be performed entirely endoscopically or laparoscopically. FIG. 37 shows an isometric view of an assembly which may be utilized to achieve part of the procedure. Deployment device 630 may have anastomosis assembly 632 preferably connected by steerable length 634 to manipulation handle 636. Assembly 632 may be steerable during insertion, preferably trans-esophageally and through the stomach, by steering grip 638 which may be located on manipulation handle 636. Control by a physician or surgeon of manipulation handle 636 may be facilitated by handle 640.

Anastomosis assembly 632 may have stapler housing 644 configured to fit intimately with distal element 646 preferably by a magnetic force, the use of which is described below. Distal element 646 is preferably tapered or rounded on one side and may have a coring anvil 648 on its opposing side. Coring anvil 648 may be tapered or rounded and may fit intimately into coring mate 650 which is preferably located near or at the center of stapler housing 644. Stapler housing 644 may also house several staples loaded within staple slots 652, which may be disposed circumferentially around coring mate 650 and may be actuated from the proximal end of length 634 by staple trigger 642.

Figure 38:
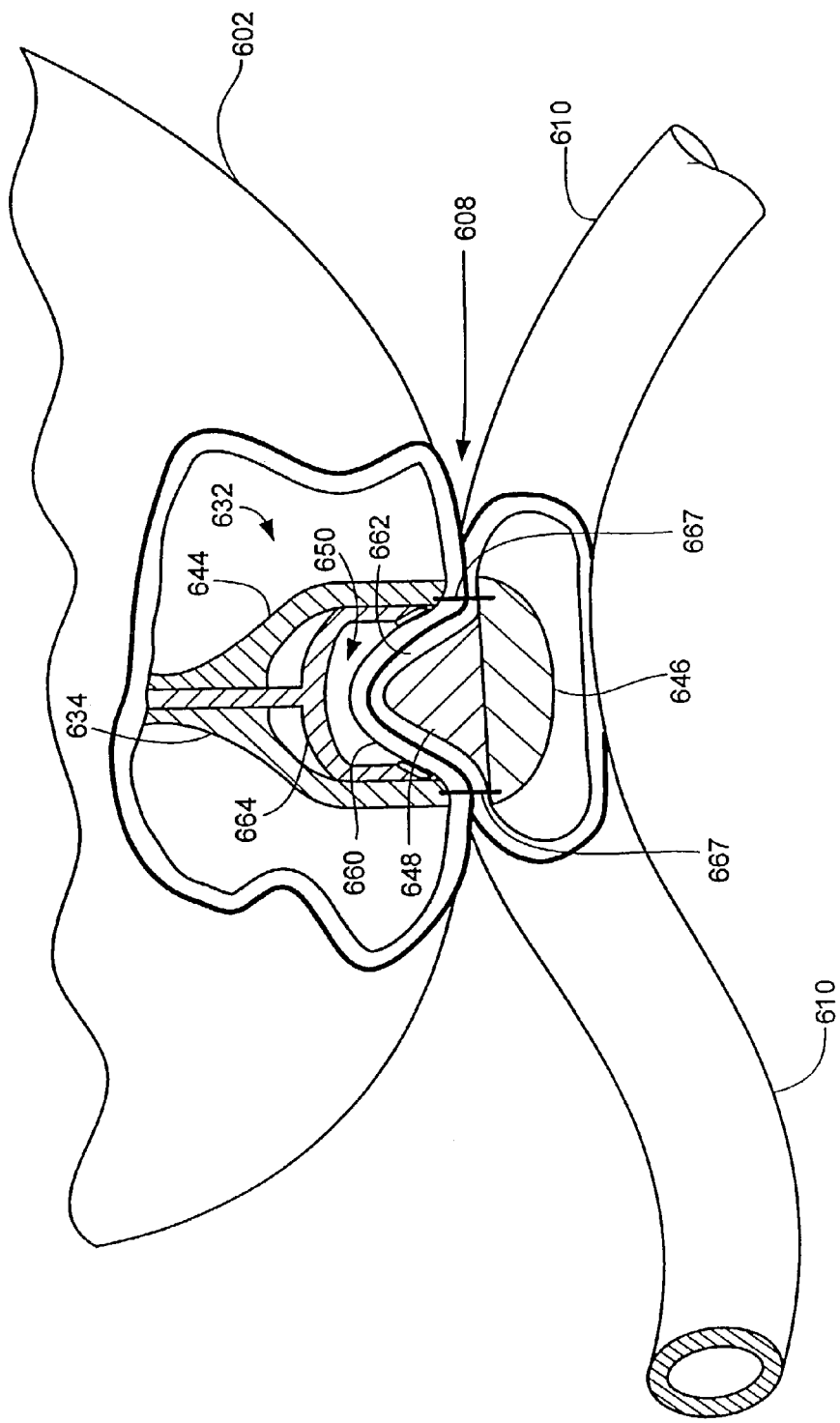
FIG. 38 shows a cross section view of an anastomosis assembly mating a portion of the stomach with a portion of the intestinal tract.

FIG. 38 shows a cross sectioned view of anastomosis assembly 632 mated with distal element 646 at first anastomosis 608 between modified pouch 602 and jejunum 610. Part of the walls of modified pouch 602 and jejunum 610 have been removed for clarity. In creating first anastomosis 608, distal element 646 may first be placed within the appropriate section of jejunum 610. This may be done by orally passing distal element 646 through the esophagus, stomach, and then through the duodenum. Distal element 646 is preferably magnetized, either by manufacturing distal element 646 from natural ferrous materials or artificially magnetizing it. Because of the magnetization, distal element 646 may be urged through the body and into place within the duodenum by, e.g., magnetic wands or magnetic pickups, which may be manipulated from outside the patient's body.

During or after placement of distal element 646, stapler housing 644, which may be attached to steerable length 634, may be introduced trans-esophageally into the stomach 602 and placed into position along stomach wall 660 at the desired site of first anastomosis 608. Once both stapler housing 644 and distal element 646 are in position, they may then be coupled together preferably by the magnetic force and attraction between the two. Moreover, the two may be brought into alignment either by alignment grooves (not shown) or by the mating of coring anvil 648 into coring mate 650. As the mating occurs, part of stomach wall 660 and intestinal wall 662 are preferably held or maintained between stapler housing 644 and distal element 646. To enhance the mating, fasteners may optionally be deployed from stapler housing 644 through staple slots 652 and preferably through both stomach wall 660 and intestinal wall 662 into distal element 646. FIG. 38 shows staples 667 deployed as fasteners, but they may comprise any type of mechanical fasteners as described above, as well as, e.g., grommet-type swages, snap lock fits, staples, screws, clips, and friction-fittings.

Once the fitting has been accomplished, the device may be left in apposition to maintain the position of stomach wall 660 and intestinal wall 662 for about one week. This may result in pressure necrosis of the tissue between stapler housing 644 and distal element 646 preferably causing the serosal layers of the gut to fuse, at which point the assembly may drop out and be passed, preferably leaving first anastomosis 608 behind. Alternatively, a coring device 664, which may be slidingly contained within stapler housing 644, may first be advanced through the center of stapler housing 644 and both stomach wall 660 and intestinal wall 662 to create first anastomosis 608. The remaining assembly may then be left to cause the pressure necrosis and fusing of tissue, as described. Another alternative may be to use stapler housing 644 and distal element 646 as a mechanism for a conventional end-to-end anastomosis (EEA) stapler. In this case, once they are aligned, a rod may be advanced through the center of the assembly to preferably lock distal element 646 to intestinal wall 662. The rod may be drawn back, preferably pulling a distal stapler segment into stapler housing 644. This action may cause staples to fire and a circumferential blade to cut out the center of the staple ring, thereby creating an anastomosis.

Figure 39:
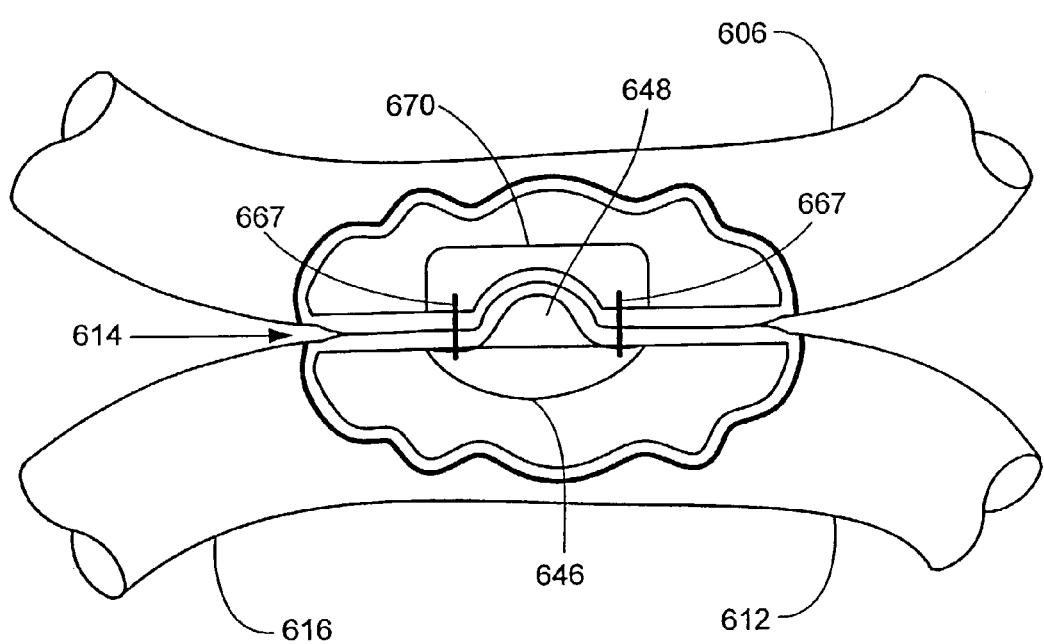
FIG. 39 shows a cross section view of another anastomosis assembly mating two different portions of the intestinal tract.

To create second anastomosis 614, a similar approach may be taken as for creating first anastomosis 608. An example of another magnetic anastomosis device which may also be used in this procedure is shown and described in U.S. Pat. No. 5,690,656 to Cope et al., which is incorporated herein by reference in its entirety. FIG. 39 shows a portion of duodenum 606 juxtaposed to a portion of ileum 612 and distal ileum 616 with part of the intestinal walls removed for clarity. In this variation, proximal element 670 may be used and is preferably a magnetized mating element for distal element 646. Distal element 646 may first be urged to the desired location preferably in ileum 612 by, e.g., magnetic wands or magnetic pickups, which may be manipulated from outside the patient's body, in the same manner as above. During or after placement of distal element 646, proximal element 670 may also be delivered or urged to the desired location in the same manner. Once both elements 646, 670 are in position, they are preferably mated together by a magnetic force. The mating may optionally be enhanced by fasteners, e.g., staples 667, to hold both elements 646, 670 in position. The intestinal wall inbetween may be cored, as described above, but it may also be simply left to undergo pressure necrosis between elements 646, 670 eventually causing the serosal layers of the gut to fuse, at which point elements 646, 670 may drop out and be passed, preferably leaving second anastomosis 614 behind.

The applications of the methods and tools discussed above are not limited to the treatment of obesity, but may include any number of further applications, e.g., GERD, which may involve manipulation of an organ interior. Modification of the above-described methods and tools for carrying out the invention, and variations of aspects of the invention that are obvious to those of skill in the art are intended to be within the scope of the claims.

We claim:

1. A method for organ volume reduction, comprising:
   positioning a device within an interior of an organ adjacent to at least one portion of tissue having at least two tissue layers to be drawn up;
   adhering the portion of tissue with the device from within the interior such that at least two tissue layers are drawn up;

approximating the portion of tissue from a first position to a second approximated position from within the interior;

fastening the portion of tissue from the first position to the second approximated position from within the interior, wherein the fastened portion of tissue includes the at least two tissue layers;

fastening the portion of tissue from within the interior with a pressure sufficient to cause the portion of tissue to self-maintain a fastened configuration; and wherein fastening the portion of tissue includes ligating the portion of tissue by urging an elastic ring over the portion of tissue including the at least two tissue layers while adhering the portion of tissue.

2. The method of claim 1, wherein adhering the portion of tissue with the device includes drawing a vacuum to approximate the portion of tissue from the first position to the second approximated position from within the interior.

3. A system for organ volume reduction, comprising:

a grasping device having a flexible shaft and manipulatable grasping members at a distal end of the flexible shaft, the grasping device adapted for insertion into an organ having at least two tissue layers defining an interior, and the grasping members adapted to draw up a portion of the at least two tissue layers of the interior of the organ; and a fastening device adapted to fasten the portion of interior with at least one discrete fastener such that the portion of interior is sustained at a pressure sufficient to cause the at least two tissue layers to self-maintain a fastened configuration.

4. The system of claim 3, wherein the grasping device is an endoscope.

5. The system of claim 3, wherein the grasping members are adapted to cinch the portion of the at least two tissue layers of the interior of the organ.

6. The system of claim 3, wherein the discrete fastener is a ring member.

7. The system of claim 3, wherein discrete fastener is a ring stapler.

8. The system of claim 3, wherein the discrete fastener is a zip tie.

9. A system for organ volume reduction, comprising:

a grasping device having a flexible shaft and forceps at a distal end of the flexible shaft, the grasping device adapted for insertion into an organ having at least two tissue layers defining an interior, and the forceps adapted to draw up and remove a portion of the at least two tissue layers of the interior of the organ; and a fastening device adapted to fasten the portion of interior with at least one discrete fastener such that the portion of interior is sustained at a pressure sufficient to cause the at least two tissue layers to self-maintain a fastened configuration.

10. The system of claim 9, wherein the grasping device is an endoscope.

11. The system of claim 9, wherein the discrete fastener is a ring member.

12. The system of claim 9, wherein the discrete fastener is a ring stapler.

13. The system of claim 9, wherein the discrete fastener is a zip tie.

* * * * *

UNITED STATES PATENT AND TRADEMARK OFFICE
CERTIFICATE OF CORRECTION

PATENT NO. : 7,503,922 B2  Page 1 of 1
APPLICATION NO. : 10/402061
DATED : March 17, 2009
INVENTOR(S) : Mark E. Deem et al.

It is certified that error appears in the above-identified patent and that said Letters Patent is hereby corrected as shown below:

Title Page, Other Publications, delete "60/234,260" and insert --60/234,360--.

Title Page, (57) Abstract, in the sixth sentence, delete "a traumatic" and insert --atraumatic--.

Drawing Sheet 7 of 37, on Fig. 6E, delete "134" and insert --134'--.

Column 15, line 38, delete "a traumatic" and insert --atraumatic--.

Column 20, line 50, delete "a's" and insert --as--.

Signed and Sealed this

Fourteenth Day of July, 2009

JOHN DOLL
*Acting Director of the United States Patent and Trademark Office*